US009840732B2

(12) United States Patent
Anderson et al.

(10) Patent No.: US 9,840,732 B2
(45) Date of Patent: Dec. 12, 2017

(54) SINGLE-PARTICLE ANALYSIS OF PARTICLE POPULATIONS

(71) Applicant: Fluidigm Corporation, South San Francisco, CA (US)

(72) Inventors: Megan Anderson, Washington, DC (US); Peilin Chen, Richmond, CA (US); Brian Fowler, San Mateo, CA (US); Fiona Kaper, Solano Beach, CA (US); Ronald Lebofsky, Etobicoke (CA); Andrew May, San Francisco, CA (US)

(73) Assignee: FLUIDIGM CORPORATION, South San Francisco, CA (US)

( * ) Notice: Subject to any disclaimer, the term of this patent is extended or adjusted under 35 U.S.C. 154(b) by 131 days.

(21) Appl. No.: 13/899,397

(22) Filed: May 21, 2013

(65) Prior Publication Data

US 2013/0323732 A1 Dec. 5, 2013

Related U.S. Application Data

(60) Provisional application No. 61/649,845, filed on May 21, 2012.

(51) Int. Cl.
| | |
|---|---|
| C12Q 1/68 | (2006.01) |
| C12P 19/34 | (2006.01) |
| C12M 1/34 | (2006.01) |
| C12M 3/00 | (2006.01) |
| C07H 21/02 | (2006.01) |
| C07H 21/04 | (2006.01) |
| C07H 21/00 | (2006.01) |
| B01D 15/08 | (2006.01) |

(52) U.S. Cl.
CPC ........... *C12Q 1/6813* (2013.01); *B01D 15/08* (2013.01); *C12Q 1/6806* (2013.01)

(58) Field of Classification Search
USPC .......... 435/6.1, 6.11, 6.12, 91.1, 91.2, 91.51, 435/183, 94, 501, 287.1, 287.2; 536/23.1, 536/24.3, 24.33, 25.3
See application file for complete search history.

(56) References Cited

U.S. PATENT DOCUMENTS

| | | |
|---|---|---|
| 4,508,625 A | 4/1985 | Graham |
| 4,683,202 A | 7/1987 | Mullis |
| 4,822,733 A | 4/1989 | Morrison |
| 5,066,584 A | 11/1991 | Gyllensten et al. |
| 5,272,081 A | 12/1993 | Weinreb et al. |
| 5,300,779 A | 4/1994 | Hillman et al. |
| 5,556,773 A | 9/1996 | Yourno |
| 5,622,821 A | 4/1997 | Selvin et al. |
| 5,639,615 A | 6/1997 | Selvin et al. |
| 5,641,628 A | 6/1997 | Bianchi |
| 5,656,433 A | 8/1997 | Selvin et al. |
| 5,723,591 A | 3/1998 | Livak et al. |
| 5,750,339 A | 5/1998 | Smith |
| 5,840,502 A | 11/1998 | Van Vlasselaer |
| 5,879,883 A | 3/1999 | Benson et al. |
| 5,932,415 A | 8/1999 | Schubert et al. |
| 5,945,283 A | 8/1999 | Kwok et al. |
| 6,013,435 A | 1/2000 | Nubaum |
| 6,045,993 A | 4/2000 | Mahony et al. |
| 6,100,029 A | 8/2000 | Lapidus et al. |
| 6,143,496 A | 11/2000 | Brown et al. |
| 6,154,707 A | 11/2000 | Livak et al. |
| 6,159,685 A | 12/2000 | Pinkel et al. |
| 6,214,558 B1 | 4/2001 | Shuber et al. |
| 6,225,094 B1 | 5/2001 | Ludwig et al. |
| 6,251,639 B1 | 6/2001 | Kurn |
| 6,258,540 B1 | 7/2001 | Lo et al. |
| 6,300,077 B1 | 10/2001 | Shuber et al. |
| 6,368,871 B1 | 4/2002 | Christel et al. |
| 6,387,652 B1 | 5/2002 | Haugland et al. |
| 6,391,559 B1 | 5/2002 | Brown et al. |
| 6,408,878 B2 | 6/2002 | Unger et al. |
| 6,432,630 B1 | 8/2002 | Blankenstein |

(Continued)

FOREIGN PATENT DOCUMENTS

| | | |
|---|---|---|
| CN | 101067156 A | 11/2007 |
| CN | 101750476 A | 6/2010 |

(Continued)

OTHER PUBLICATIONS

Spurgeon et al., High Throughput Gene Expression Measurement with Real Time PCR in a Microfluidic Dynamic Array. PLoS One, 3, e1662, 2008.*
PCT Invitation to Pay Additional Fees and, Where Applicable, Protest Fee dated Oct. 10, 2013 issued in PCT/US2013/042086.
PCT International Search Report and Written Opinion dated Dec. 11, 2013 issued in PCT/US2013/042086.
PCT International Preliminary Report on Patentability and Written Opinion dated Dec. 4, 2014 issued in PCT/US2013/042086.
Hollants et al. (2012) "Microfluidic Amplification as a Tool for Massive Parallel Sequencing of the Familial Hypercholesterolemia Genes", Clinical Chemistry, 58(4): 717-724.
Kuang et al. (2004) "Simultaneously Monitoring Gene Expression Kinetics and Genetic Noise in Single Cells by Optical Well Arrays", *Analytical Chemistry*, 76( 21): 6282-6286.
Spurgeon et al. (2008) "High Throughput Gene Expression Measurement with Real Time PCR in a Microfluidic Dynamic Array", *PLoS One*, 3(2):e1662, pp. 1-7.
U.S. Appl. No. 61/605,016, filed Feb. 29, 2012, Fowler et al.
U.S. Appl. No. 14/092,728, filed Nov. 27, 2013, Schwartz et al.

(Continued)

*Primary Examiner* — Frank Lu
(74) *Attorney, Agent, or Firm* — Emily M. Haliday; Weaver Austin Villeneuve & Sampson LLP

(57) ABSTRACT

In certain embodiments, the invention provides methods and devices for assaying single particles in a population of particles, wherein at least two parameters are measured for each particle. One or more parameters can be measured while the particles are in the separate reaction volumes. Alternatively or in addition, one or more parameters can be measured in a later analytic step, e.g., where reactions are carried out in the separate reaction volumes and the reaction products are recovered and analyzed. In particular embodiments, one or more parameter measurements are carried out "in parallel," i.e., essentially simultaneously in the separate reaction volumes.

46 Claims, 22 Drawing Sheets

(56) References Cited

U.S. PATENT DOCUMENTS

| | | |
|---|---|---|
| 6,440,706 B1 | 8/2002 | Vogelstein et al. |
| 6,503,722 B1 | 1/2003 | Valkirs |
| 6,511,967 B1 | 1/2003 | Weissleder et al. |
| 6,605,451 B1 | 8/2003 | Marmaro et al. |
| 6,618,679 B2 | 9/2003 | Loehrlein et al. |
| 6,632,642 B1 | 10/2003 | Motoyama et al. |
| 6,706,471 B1 | 3/2004 | Brow et al. |
| 6,723,505 B1 | 4/2004 | Karlsen |
| 6,753,147 B2 | 6/2004 | Vogelstein et al. |
| 6,783,928 B2 | 8/2004 | Hvichia et al. |
| 6,824,981 B2 | 11/2004 | Chait et al. |
| 6,927,028 B2 | 8/2005 | Dennis et al. |
| 6,960,437 B2 | 11/2005 | Enzelberger et al. |
| 7,097,980 B2 | 8/2006 | Barany et al. |
| 7,153,658 B2 | 12/2006 | Andersen et al. |
| 7,312,034 B2 | 12/2007 | Virgos et al. |
| 7,442,506 B2 | 10/2008 | Dhallan |
| 7,476,363 B2 | 1/2009 | Unger et al. |
| 7,851,148 B2 | 12/2010 | Han |
| 7,887,753 B2 | 2/2011 | Quake et al. |
| 8,318,434 B2 | 11/2012 | Cuppens |
| 8,450,063 B2 | 5/2013 | Dube et al. |
| 8,628,923 B2 | 1/2014 | Hamilton et al. |
| 8,691,509 B2 | 4/2014 | May et al. |
| 8,697,363 B2 | 4/2014 | Mir et al. |
| 9,074,204 B2 | 7/2015 | Anderson et al. |
| 9,249,459 B2 | 2/2016 | Hamilton et al. |
| 9,304,065 B2 | 4/2016 | Fowler et al. |
| 9,364,829 B2 | 6/2016 | Heid et al. |
| 2001/0046681 A1 | 11/2001 | Senapathy |
| 2002/0064779 A1 | 5/2002 | Landegren et al. |
| 2002/0160361 A1 | 10/2002 | Loehrlein et al. |
| 2002/0160404 A1 | 10/2002 | Dietmaier et al. |
| 2002/0166760 A1 | 11/2002 | Prentiss et al. |
| 2003/0017591 A1 | 1/2003 | Kurn |
| 2003/0022207 A1 | 1/2003 | Balasubramanian et al. |
| 2003/0033091 A1 | 2/2003 | Opalsky et al. |
| 2003/0119004 A1 | 6/2003 | Wenz et al. |
| 2003/0138829 A1 | 7/2003 | Unger et al. |
| 2003/0180715 A1 | 9/2003 | Kemp et al. |
| 2003/0204331 A1 | 10/2003 | Whitney et al. |
| 2003/0228613 A1 | 12/2003 | Bornarth et al. |
| 2004/0005582 A1 | 1/2004 | Shipwash |
| 2004/0005594 A1 | 1/2004 | Holliger et al. |
| 2004/0037470 A1 | 2/2004 | Simske |
| 2004/0048360 A1 | 3/2004 | Wada |
| 2004/0053352 A1 | 3/2004 | Ouyang |
| 2004/0072278 A1 | 4/2004 | Chou et al. |
| 2004/0081993 A1 | 4/2004 | Cantor et al. |
| 2004/0086892 A1 | 5/2004 | Crothers et al. |
| 2004/0091879 A1 | 5/2004 | Nolan et al. |
| 2004/0096892 A1 | 5/2004 | Wang et al. |
| 2004/0110153 A1 | 6/2004 | Dong et al. |
| 2004/0110166 A1 | 6/2004 | Macevicz |
| 2004/0110191 A1 | 6/2004 | Winkler et al. |
| 2004/0137470 A1 | 7/2004 | Dhallan |
| 2004/0142463 A1 | 7/2004 | Walker |
| 2004/0144651 A1 | 7/2004 | Huang |
| 2004/0185495 A1 | 9/2004 | Schueler et al. |
| 2004/0203037 A1 | 10/2004 | Lo et al. |
| 2004/0209299 A1 | 10/2004 | Pinter et al. |
| 2004/0229349 A1 | 11/2004 | Daridon |
| 2005/0019792 A1 | 1/2005 | McBride et al. |
| 2005/0049793 A1 | 3/2005 | Paterlini-Brechot |
| 2005/0064488 A1 | 3/2005 | Huh et al. |
| 2005/0072946 A1 | 4/2005 | Studer et al. |
| 2005/0095634 A1 | 5/2005 | Baker et al. |
| 2005/0129581 A1 | 6/2005 | McBride et al. |
| 2005/0145496 A1 | 7/2005 | Goodsaid et al. |
| 2005/0158754 A1 | 7/2005 | Puffenberger et al. |
| 2005/0164241 A1 | 7/2005 | Hahn et al. |
| 2005/0170373 A1 | 8/2005 | Monforte |
| 2005/0221341 A1 | 10/2005 | Shimkets |
| 2005/0221373 A1 | 10/2005 | Enzelberger et al. |
| 2005/0250111 A1 | 11/2005 | Xie |
| 2005/0252773 A1 | 11/2005 | McBride et al. |
| 2005/0260640 A1 | 11/2005 | Andersen et al. |
| 2005/0287611 A1 | 12/2005 | Nugent, IV et al. |
| 2006/0000772 A1 | 1/2006 | Sano |
| 2006/0040297 A1 | 2/2006 | Leamon et al. |
| 2006/0046258 A1 | 3/2006 | Lapidus et al. |
| 2006/0051265 A1 | 3/2006 | Mohamed |
| 2006/0051775 A1 | 3/2006 | Bianchi |
| 2006/0053503 A1 | 3/2006 | Culiat et al. |
| 2006/0073125 A1 | 4/2006 | Clarke et al. |
| 2006/0105380 A1 | 5/2006 | Slepnev |
| 2006/0121452 A1 | 6/2006 | Dhallan |
| 2006/0141518 A1 | 6/2006 | Lao et al. |
| 2006/0223178 A1 | 10/2006 | Barber |
| 2006/0252068 A1 | 11/2006 | Lo |
| 2006/0252071 A1 | 11/2006 | Lo |
| 2007/0020640 A1 | 1/2007 | McCloskey et al. |
| 2007/0059680 A1 | 3/2007 | Kapur |
| 2007/0059683 A1 | 3/2007 | Barber |
| 2007/0059716 A1 | 3/2007 | Balis |
| 2007/0059719 A1 | 3/2007 | Grisham |
| 2007/0059774 A1 | 3/2007 | Grisham |
| 2007/0059781 A1 | 3/2007 | Kapur |
| 2007/0072290 A1 | 3/2007 | Hvichia |
| 2007/0077570 A1 | 4/2007 | Lao et al. |
| 2007/0172873 A1 | 7/2007 | Brenner et al. |
| 2007/0202525 A1 | 8/2007 | Quake et al. |
| 2007/0207466 A1 | 9/2007 | Cantor |
| 2007/0219364 A1 | 9/2007 | Andersen et al. |
| 2007/0224613 A1 | 9/2007 | Strathmann |
| 2008/0020390 A1 | 1/2008 | Mitchell |
| 2008/0023399 A1 | 1/2008 | Inglis |
| 2008/0026390 A1 | 1/2008 | Stoughton |
| 2008/0038733 A1 | 2/2008 | Bischoff |
| 2008/0050739 A1 | 2/2008 | Stoughton |
| 2008/0070792 A1 | 3/2008 | Stoughton |
| 2008/0071076 A1 | 3/2008 | Hahn |
| 2008/0090239 A1 | 4/2008 | Shoemaker |
| 2008/0096766 A1 | 4/2008 | Lee |
| 2008/0108063 A1 | 5/2008 | Lucero et al. |
| 2008/0131937 A1 | 6/2008 | Schroeder |
| 2008/0138809 A1 | 6/2008 | Kapur |
| 2008/0153090 A1 | 6/2008 | Lo |
| 2008/0182261 A1 | 7/2008 | Bianchi |
| 2008/0220422 A1 | 9/2008 | Shoemaker et al. |
| 2008/0223721 A1 | 9/2008 | Cohen et al. |
| 2009/0029377 A1 | 1/2009 | Lo et al. |
| 2009/0053719 A1 | 2/2009 | Lo et al. |
| 2009/0069194 A1 | 3/2009 | Ramakrishnan et al. |
| 2009/0087847 A1 | 4/2009 | Lo et al. |
| 2009/0163366 A1 | 6/2009 | Nickerson et al. |
| 2009/0170113 A1 | 7/2009 | Quake et al. |
| 2009/0170114 A1 | 7/2009 | Quake et al. |
| 2009/0170713 A1 | 7/2009 | van Eijk et al. |
| 2009/0233802 A1 | 9/2009 | Bignell et al. |
| 2009/0239308 A1 | 9/2009 | Dube et al. |
| 2009/0257920 A1 | 10/2009 | Facer et al. |
| 2009/0317798 A1* | 12/2009 | Heid ............ B01L 3/5027 435/6.12 |
| 2010/0069250 A1 | 3/2010 | White, III et al. |
| 2010/0120038 A1 | 5/2010 | Mir et al. |
| 2010/0120077 A1 | 5/2010 | Daridon |
| 2010/0143908 A1 | 6/2010 | Gillevet |
| 2010/0178655 A1 | 7/2010 | Hamilton et al. |
| 2010/0203538 A1 | 8/2010 | Dube et al. |
| 2010/0273219 A1 | 10/2010 | May et al. |
| 2010/0285537 A1 | 11/2010 | Zimmermann |
| 2011/0053806 A1 | 3/2011 | Amin |
| 2011/0129841 A1 | 6/2011 | Heid et al. |
| 2011/0143949 A1 | 6/2011 | Heid et al. |
| 2011/0143955 A1 | 6/2011 | Weiner et al. |
| 2011/0207134 A1 | 8/2011 | Faham et al. |
| 2011/0257039 A1 | 10/2011 | Wang et al. |
| 2013/0005585 A1 | 1/2013 | Anderson et al. |
| 2013/0296196 A1 | 11/2013 | Fowler et al. |
| 2013/0302807 A1 | 11/2013 | Fowler et al. |
| 2013/0302883 A1 | 11/2013 | Fowler et al. |
| 2013/0302884 A1 | 11/2013 | Fowler et al. |
| 2014/0087973 A1 | 3/2014 | Amin |

(56) References Cited

U.S. PATENT DOCUMENTS

| | | |
|---|---|---|
| 2014/0154679 A1 | 6/2014 | Dube et al. |
| 2014/0186827 A1 | 7/2014 | Jones et al. |
| 2014/0193812 A1 | 7/2014 | Hamilton et al. |
| 2014/0227691 A1 | 8/2014 | May et al. |
| 2014/0272952 A1 | 9/2014 | May et al. |
| 2014/0296090 A1 | 10/2014 | Mir et al. |
| 2016/0208322 A1 | 7/2016 | Anderson et al. |
| 2016/0340728 A1 | 11/2016 | Hamilton et al. |

FOREIGN PATENT DOCUMENTS

| | | |
|---|---|---|
| EP | 0197196 A1 | 10/1986 |
| EP | 2201143 B1 | 11/2012 |
| JP | 2005538727 A | 12/2005 |
| JP | 2008539711 A | 11/2008 |
| JP | 2009529670 A | 8/2009 |
| JP | 2010535511 A | 11/2010 |
| WO | WO 91/16452 | 10/1991 |
| WO | WO 97/22719 | 6/1997 |
| WO | WO 98/02528 | 1/1998 |
| WO | WO 98/39474 | 9/1998 |
| WO | WO 98/47003 | 10/1998 |
| WO | WO 01/01025 | 1/2001 |
| WO | WO 01/59161 A2 | 8/2001 |
| WO | WO 02/12896 | 2/2002 |
| WO | WO 02/36815 A2 | 5/2002 |
| WO | WO 02/40874 A1 | 5/2002 |
| WO | WO 02/43615 | 6/2002 |
| WO | WO 02/002772 | 9/2002 |
| WO | WO 02/081729 A2 | 10/2002 |
| WO | WO 03/048295 | 6/2003 |
| WO | WO 03/085379 A2 | 10/2003 |
| WO | WO 04/000721 A2 | 12/2003 |
| WO | WO 2004/029221 A2 | 4/2004 |
| WO | WO 2004/029221 A3 | 4/2004 |
| WO | WO 2004/040001 A2 | 5/2004 |
| WO | WO 2004/051218 A2 | 6/2004 |
| WO | WO 2004/081183 A2 | 9/2004 |
| WO | WO 2004/088310 | 10/2004 |
| WO | WO 2004/089810 A2 | 10/2004 |
| WO | WO 2004/113877 | 12/2004 |
| WO | WO 2005/003394 A2 | 1/2005 |
| WO | WO 2005/023091 A2 | 3/2005 |
| WO | WO 2005/023091 A3 | 3/2005 |
| WO | WO 2005/030822 | 4/2005 |
| WO | WO 2005/064020 A1 | 7/2005 |
| WO | WO 2005/084191 | 9/2005 |
| WO | WO 2005/107938 A2 | 11/2005 |
| WO | WO 2006/023919 A2 | 3/2006 |
| WO | WO 2006/128010 A2 | 11/2006 |
| WO | WO 2007/024798 A2 | 3/2007 |
| WO | WO 2007/033385 A2 | 3/2007 |
| WO | WO 2007/044091 A2 | 4/2007 |
| WO | WO 2007/104816 A2 | 9/2007 |
| WO | WO 2008/015396 A2 | 2/2008 |
| WO | WO 2009/013492 | 1/2009 |
| WO | WO 2009/013496 | 1/2009 |
| WO | WO 2009/019455 | 2/2009 |
| WO | WO 2009/021215 | 2/2009 |
| WO | WO 2010/027870 A2 | 3/2010 |
| WO | WO 2010/083250 A2 | 7/2010 |
| WO | WO 2010/115154 A1 | 10/2010 |
| WO | WO 2011/088226 A2 | 7/2011 |
| WO | WO 2011/142836 A9 | 11/2011 |
| WO | WO 2011/143659 A2 | 11/2011 |
| WO | WO 2012/162267 A2 | 11/2012 |
| WO | WO 2013/130714 A1 | 9/2013 |
| WO | WO 2013/177206 A2 | 11/2013 |

OTHER PUBLICATIONS

U.S. Appl. No. 14/180,262, filed Feb. 13, 2014, May et al.
U.S. Appl. No. 14/184,499, filed Feb. 19, 2014, Mir et al.
U.S. Appl. No. 14/977,414, filed Dec. 21, 2015, Hamilton et al.
US Office Action dated May 3, 2012 issued in U.S. Appl. No. 12/548,132.
US Final Office Action dated Feb. 12, 2013 issued in U.S. Appl. No. 12/548,132.
US Notice of Allowance dated Nov. 18, 2013 issued in U.S. Appl. No. 12/548,132.
US Office Action dated Feb. 2, 2016 issued in U.S. Appl. No. 14/184,499.
US Final Office Action dated Aug. 15, 2016 issued in U.S. Appl. No. 14/184,499.
US Office Action dated Jun. 28, 2012 issued in U.S. Appl. No. 12/753,703.
US Final Office Action dated Mar. 25, 2013 issued in U.S. Appl. No. 12/753,703.
US Office Action dated Jul. 10, 2013 issued in U.S. Appl. No. 12/753,703.
US Notice of Allowance dated Nov. 14, 2013 issued in U.S. Appl. No. 12/753,703.
US Office Action [Preinterview First Office Action] dated Jul. 15, 2015 issued in U.S. Appl. No. 14/180,262.
US Office Action [First Action Interview Office Action Summary] dated Nov. 10, 2015 issued in U.S. Appl. No. 14/180,262.
US Final Office Action dated Apr. 8, 2016 issued in U.S. Appl. No. 14/180,262.
US Office Action dated Feb. 28, 2014 issued in U.S. Appl. No. 13/476,911.
US Final Office Action dated Sep. 17, 2014 issued in U.S. Appl. No. 13/476,911.
US Notice of Allowance dated Mar. 6, 2015 issued in U.S. Appl. No. 13/476,911.
U.S. Appl. No. 60/764,420, filed by Quake Feb. 2, 2006, 38 pages.
US Office Action dated Sep. 27, 2010 issued in U.S. Appl. No. 11/916,025.
US Final Office Action dated May 13, 2011 issued in U.S. Appl. No. 11/916,025.
US Office Action dated Aug. 17, 2012 issued in U.S. Appl. No. 11/916,025.
US Final Office Action dated Apr. 26, 2013 issued in U.S. Appl. No. 11/916,025.
US Office Action dated May 2, 2014 issued in U.S. Appl. No. 11/916,025.
US Office Action dated Mar. 14, 2013 issued in U.S. Appl. No. 12/945,483.
US Final Office Action dated Dec. 4, 2013 issued in U.S. Appl. No. 12/945,483.
US Office Action dated Jul. 17, 2014 issued in U.S. Appl. No. 12/945,483.
US Final Office Action dated Feb. 26, 2015 issued in U.S. Appl. No. 12/945,483.
US Notice of Allowance dated Feb. 10, 2016 issued in U.S. Appl. No. 12/945,483.
US Notice of Allowance [Supplemental Notice of Allowability] dated Feb. 22, 2016 issued in U.S. Appl. No. 12/945,483.
US Office Action dated Feb. 24, 2015 issued in U.S. Appl. No. 12/945,506.
US Final Office Action dated Nov. 10, 2015 issued in U.S. Appl. No. 12/945,506.
US Office Action dated Apr. 13, 2012 issued in U.S. Appl. No. 12/687,018.
US Final Office Action dated Mar. 1, 2013 issued in U.S. Appl. No. 12/687,018.
US Notice of Allowance dated Sep. 9, 2013 issued in U.S. Appl. No. 12/687,018.
US Office Action dated Oct. 21, 2014 issued in U.S. Appl. No. 14/102,331.
US Notice of Allowance dated Apr. 13, 2015 issued in U.S. Appl. No. 14/102,331.
US Notice of Allowance dated Oct. 1, 2015 issued in U.S. Appl. No. 14/102,331.
US Office Action, U.S. Appl. No. 11/701,686, dated Jan. 28, 2009, 24 pages.
Applicant's Response to US Office Action, U.S. Appl. No. 11/701,686, dated Jun. 17, 2009, 25 pages.

(56) References Cited

OTHER PUBLICATIONS

US Final Office Action, U.S. Appl. No. 11/701,686, dated Sep. 11, 2009, 40 pages.
PCT International Search Report and Written Opinion dated May 10, 2010 issued in PCT/US2009/055083 (WO/2010/027870).
PCT International Preliminary Examination Report dated Mar. 10, 2011 issued in PCT/US2009/055083 (WO/2010/027870).
Canadian Office Action dated Jul. 8, 2015 issued in CA 2,734,868.
Chinese First Office Action dated Nov. 1, 2012 issued in CN200980142505.9.
Chinese Second Office Action dated Sep. 17, 2013 issued in CN200980142505.9.
Chinese Third Office Action dated Apr. 9, 2014 issued in CN200980142505.9.
Chinese Decision of Rejection dated Oct. 21, 2014 issued in CN200980142505.9.
Chinese Notification of Reexamination dated Jul. 28, 2016 issued in CN200980142505.9.
European Extended Search Report dated Oct. 15, 2012 issued in EP09812052.0.
PCT International Search Report and Written Opinion dated Aug. 30, 2010 issued in PCT/US2010/029854 (WO/2010/115154).
PCT International Preliminary Examination Report dated Oct. 13, 2011 issued in PCT/US2010/029854 (WO/2010/115154).
Australian Office Action dated May 23, 2014 issued in AU2010232439.
Canadian Office Action dated Feb. 26, 2016 issued in CA 2,757,560.
Chinese Office Action dated Mar. 4, 2013 issued in CN201080021508.X.
Chinese Office Action dated Jan. 13, 2014 issued in CN201080021508.X.
Chinese First Office Action dated Mar. 2, 2015 issued in CN201410138786.3.
Chinese Second Office Action dated Dec. 22, 2015 issued in CN201410138786.3.
Chinese First Office Action dated Jun. 15, 2015 issued in CN201410139163.8.
Chinese Second Office Action dated Apr. 22, 2016 issued in CN201410139163.8.
Eurasian Office Action dated Nov. 27, 2013 issued in EA201171206.
Eurasian Office Action dated Jul. 18, 2014 issued in EA201171206.
European Extended Search Report dated Jul. 19, 2012 issued in EP 10 759 511.8.
European Office Action dated Mar. 15, 2013 issued in EP 10 759 511.8.
European Extended Search Report dated Sep. 16, 2014 issued in EP 14 158 911.9.
European Office Action dated May 6, 2016 issued in EP 14 158 911.9.
Israel Office Action dated Mar. 3, 2014 issued in IL215462—translation only.
Israel Office Action [Notification of Technical Defects Prior to Allowance of Application] dated Feb. 11, 2015 issued in IL215462.
Japanese Office Action dated Aug. 25, 2014 issued in JP2012-503757.
Japanese Final Rejection dated Jul. 17, 2015 issued in JP2012-503757.
Japanese Final Rejection dated Mar. 18, 2016 issued in JP2012-503757.
Singapore Written Opinion dated Oct. 31, 2013 issued in SG201107142-0.
PCT International Search Report and Written Opinion dated Dec. 7, 2012 issued in PCT/US2012/038894 (WO/2012/162267).
PCT International Preliminary Report on Patentability dated Apr. 8, 2014 issued in PCT/US2012/038894 (WO/2012/162267).
Chinese Office Action [English description & Chinese Office Action] dated May 6, 2015 issued in CN 201280033406.9.
Chinese Office Action [partial English Description] dated Mar. 24, 2016 issued in CN 201280033406.9.
European Extended Search Report dated May 20, 2015 issued in EP 12 789 957.3.
PCT International Search Report and Written Opinion dated Sep. 16, 2010 issued in PCT/US2010/020942 [WO 2010/083250].
PCT International Preliminary Report on Patentability and Written Opinion dated Jul. 19, 2011 issued in PCT/US2010/020942 [WO 2010/083250].
Chinese Office Action dated Feb. 26, 2013 issued in 201080011426.7.
Chinese Second Office Action dated Nov. 15, 2013 issued in 201080011426.7.
Chinese Third Office Action dated May 13, 2014 issued in 201080011426.7.
Chinese Fourth Office Action dated Dec. 2, 2014 issued in 201080011426.7.
Chinese Decision of Reexamination [no translation] dated Sep. 2, 2016 issued in 201080011426.7.
Eurasian Office Action dated Mar. 29, 2013 issued in 201170933.
European Supplementary Search Report on Patentability and Written Opinion dated Apr. 26, 2012 issued in EP 10 73 2056.6.
European Office Action dated Apr. 7, 2014 issued in EP 10 732 056.6.
Israel Office Action dated Nov. 14, 2013 issued in IL 214034.
Israel Office Action dated Feb. 1, 2015 issued in IL 214034.
Singapore Search Report and Written Opinion mailed May 23, 2013 [report dated Feb. 26, 2013] issued in SG 201205203-1.
Singapore Search Report and Second Written Opinion mailed Jan. 16, 2014 [report dated Dec. 13, 2013] issued in SG 201205203-1.
Singapore Search Report and Third Written Opinion mailed Nov. 6, 2014 [report dated Aug. 1, 2014] issued in SG 201205203-1.
Singapore Search Report and Written Opinion mailed Jun. 8, 2015 [report dated Aug. 1, 2014] issued in SG 201205203-1.
PCT International Search Report and Written Opinion dated Sep. 24, 2007 issued in PCT/US2006/021416 [WO2007/044091].
PCT International Preliminary Report on Patentability dated Dec. 6, 2007 issued in PCT/US2006/021416 [WO2007/044091].
European Supplemental Search Report and Written Opinion dated Aug. 28, 2009 issued in EP 06 83 6075.
European Office Action dated Dec. 23, 2009 issued in EP 06 83 6075.
European Office Action dated May 14, 2012 issued in EP 06 83 6075.
European Oral Proceedings dated May 17, 2013 issued in EP 06 83 6075.
European Supplemental Search Report dated Jun. 14, 2012 issued in EP11196269.
European Extended Search Report dated Jan. 30, 2014 issued in EP 13 18 1405.
European Office Action dated Oct. 16, 2015 issued in EP 13 181 405.5.
PCT International Search Report and Written Opinion dated Sep. 18, 2008 issued in PCT/US2007/003209 (WO 2007/092474 A3) [8 pages].
Chinese First Office Action [Description in English] dated Oct. 21, 2015 issued in CN 201380038636.9.
Chinese Second Office Action [Description in English] dated Aug. 5, 2016 issued in CN 201380038636.9.
European Office Action dated Aug. 16, 2016 issued in EP 13 726 975.9.
Singapore Search Report and Written Opinion dated Jul. 20, 2015 issued in SG 11201407901P.
Singapore Examination Report dated Feb. 23, 2016 issued in SG 11201407901P.
Adams et al., (2004) "Increase of Circulating Endothelial Progenitor Cells in Patients With Coronary Artery Disease After Exercise-Induced Ischemia," *Arterioscler. Thromb. Vase. Bioi.*, pp. 1-8.
Adinolfi et al., (1997) "Rapid detection of aneuploidies by microsatellite and the quantitative fluorescent polymerase chain reaction," *Prenatal Diagnosis*, 17(13):1299-1311.
Ahn et al., (1996) "A Fully Integrated Micromachined Magnetic Particle Separator," *J. of Microelectromechanical Systems*, 5 (3): 151-158.

(56) References Cited

OTHER PUBLICATIONS

Akimitsu et al., (2003) "Enforced cytokinesis without complete nuclear division in embryonic cells depleting the activity of DNA topoisomerase llalpha," *Genes to Cells*, 8:393-402.
Allcock and Lampe, (1990) "The Scope of Polymer Chemistry," *Contemporary Polymer Chemistry, 2nd Ed., Prentice Hall*: Englewood Cliffs, NJ, pp. 1-20 (plus cover and copyright pages).
Amirlak and Couldwell, (2003) "Apoptosis in glioma cells: review and analysis of techniques used for study with focus on the laser scanning cytometer," *J. Neuro-Oncol.*, 63:129-145.
Anderson and Young, (1985) "Chapter 4: Quantitative Filter Hybridisation," *Nucleic Acid Hybridisation*, pp. 73-111.
Ao et al. (1998) "Preimplantation genetic diagnosis of inherited cancer:Familial adenomatous *Polyposis coli*" *Journal of Assisted Reproduction and Genetics* 15(3): 140-144.
Awais et al., (2004) "A Genetically Encoded Fluorescent Indicator Capable of Discriminating Estrogen Agonists from Antagonists in Living Cells," *Anal Chem.*, 76(8):2181-2186.
Balaji et al., (2004) "Live cell ultraviolet microscopy: a comparison between two- and three-photon excitation," *Microsc. Res. Tech.*, 63:67-71.
Balmer et al., (2003) "Elevated methyl-CpG-binding protein 2 expression is acquired during postnatal human brain development and is correlated with alternative polyadenylation," *J. Mol. Med.*, 81:61-68.
Baskin et al., (2003) "Thimerosal Induces DNA Breaks, Caspase-3 Activation, Membrane Damage, and Cell Death in Cultured Human Neurons and Fibroblasts," *Toxicol. Sci.*, 74:361-368.
Beitsch, P.D. et al., (2000) "Detection of Carcinoma Cells in the Blood of Breast Cancer Patients", *Am. J. Surg.*, 180:446-449.
Beliakoff et al., (2003) "Hormone-Refractory Breast Cancer Remains Sensitive to the Antitumor Activity of Heat Shock Protein 90 Inhibitors," *Clin. Cancer Res.*, 9:4961-4971.
Bennett et al., (2005) "Toward the $1000 human genome," *Pharmacogenomics*, 6(4):373-82.
Berger et al., (2001) "Design of a microfabricated magnetic cell separator," *Electrophoresis*, 22:3883-92.
Berlman, I. B., (1971) "Handbook of Fluorescence Spectra of Aromatic Molecules," *2nd Ed., Academic Press*: New York, NY, Chapters 1 and 3, pp. 1-38, 47-66 (plus cover and copyright pages).
Bertram et al., (Jan. 1, 1995) "Detection of DNA in Single Cells Using an Automated Cell Deposition Unit and PCR", *Biotechniques, Informa Healthcare*, US, 19(4):616, 618-620.
Binladen et al. (Feb. 2007) "The use of coded PCR Primers enables High-Throughput Sequencing of multiple homolog amplification products by 454 parallel sequencing," *Plos One*, 2(2):e197, 11 pages [Published online Feb. 14, 2007].
Blake et al., (1999) "Assessment of multiplex fluorescent PCR for screening single cells for trisomy 21 and single gene defects," *Mol. Human Reproduction*, 5(12):1166-1175.
Blazek et al. (2013) "Proximity Ligation Assay for High-content Profiling of Cell Signaling Pathways on a Microfluidic Chip," *Mol. Cell. Proteomics*, 12(12):3898-3907.
Bocsi et al., (2004) "Scanning fluorescent microscopy analysis is applicable for absolute and relative cell frequency determinations," *Cytometry*, 61A:1-8.
Bode et al., (2006) "Mutations in the tyrosine kinase domain of the *EGFR* gene are rare in synovial sarcoma," *Modern Pathology*, 19:541-7.
Bollmann et al., (2003) "Determination of features indicating progression in atypical squamous cells with undetermined significance," *Cancer*, 99:113-117.
Bollmann et al., (2003) "Human papillomavirus typing and DNA ploidy determination of squamous intraepithelial lesions in liquid-based cytologic samples," *Cancer*, 99:57-62.
Braslavsky et al., (2003) "Sequence information can be obtained from single DNA molecules," *PNAS*, 100(7):3960-3964.
Braunschweig et al., (2004) "X-chromosome inactivation ratios affect wild-type MeCP2 expression within mosaic Rett syndrome and *Mecp2l+* mouse brain," *Hum. Mol. Genet.*, 13(12):1275-1286.
Brower, (2003) "Evidence of Efficacy: Researchers Investigating Markers for Angiogenesis Inhibitors," *J. Natl. Cancer. Inst.*, 95(19):1425-1427.
Brownie et al. (1997) "The elimination of primer-dimer accumulation in PCR" *Nucleic Acids Research* 25(16):3235-3241.
$C_1$™ Single-Cell AutoPrep System (2012) *Fluidigm Corporation*, pp. 1-4.
Caggana, (2003) "Microfabricated devices for sparse cell isolation," CNF Project #905-00, *Cornell NanScale Facility*, 2 cover pages; pp. 38-39.
Caggana, (2004-05) "Microfabricated devices for sparse cell isolation," CNF Project #905-00, *Cornell Nanoscale Facility*, pp. 32-33.
Cai et al., (2003) "Toxicity of Acetaminophen, Salicylic Acid, and Caffeine for First-Passage Rat Renal Inner Medullary Collecting Duct Cells," *J. Pharmacology Exp. Ther.*, 306(1):35-42.
Chan et al., (2004) "DNA Mapping Using Microfluidic Stretching and Single-Molecule Detection of Fluorescent Site-Specific Tags," *Genome Res.*, 14:1137-1146.
Chao et al., (2008) "Microfluidic single-cell analysis of intracellular compounds," *J. R. Soc. Interface*, Suppl 2, 5:S139-S150.
Cheng et al., (2003) "Immunocytochemical analysis of prostate stem cell antigen as adjunct marker for detection of urothelial transitional cell carcinoma in voided urine specimens," *The Journal of Urolology*, 169:2094-2100.
Chigaev et al., (2004) "Conformational regulation of $\alpha_4 \beta_1$-integrin affinity by reducing agents. 'Inside-out' signaling is independent of and additive to reduction-regulated integrin activation," *J. Biol. Chem.*,279(31):32435-32443.
Chiu et al., (2001) "Effects of blood-processing protocols on fetal and total DNA quantification in maternal plasma," *Clin. Chem.*, 47(9):1607-1613.
Choesmel et al., (2004) "Enrichment methods to detect bone marrow micrometastases in breast carcinoma patients: clinica relevance," *Breast Cancer Res.*, 6(5):R556-R569.
Chou et al. (1999) A microfabricated device for sizing and sorting DNA molecules, *Proc. Natl. Acad. Sci. USA*, 96:11-13.
Chou et al., (2000) "Integrated Elastomer Fluidic Lab-on-a-chip-Surface Patterning and DNA Diagnostics," in *Proceedings of the Solid State Actuator and Sensor Workshop*, Hilton Head, S.C., 4 pp.
Chung et al., (2003) "Tea and Cancer Prevention: Studies in Animals and Humans," *J. Nutr.*, 133:3268S-3274S.
Cirigliano et al., (2001) "Clinical application of multiplex quantitative fluorescent polymerase chain reaction (QF-PCR) for the rapid prenatal detection of common chromosome aneuploidies," *Mol. Human Reproduction*, 7(10):1001-1006.
Claytor et al., (2003) "The cleaved peptide of PAR1 is a more potent stimulant of platelet-endothelial cell adhesion than is thrombin," *J. Vasc. Surg.*, 37:440-445.
Crowder et al., (2005) "PML mediates IFN-$\alpha$-induced apoptosis in myeloma by regulating Trail induction," *Blood*, 105(3):1280-1287.
Cummins et al., (2003) "Persistent Localization of Activated Extracellular Signal-Regulated Kinases (ERK 1/2) is Epithelial Cell-Specific in an Inhalation Model of Asbestosis," *Am. J. Pathol.*, 162(3):713-720.
D'Amico et al., (2003) "The Role of *Ink4a/Arf* in ErbB2 Mammary Gland Tumorigenesis," *Cancer Res.*, 63:3395-3402.
Davis et al., (2003) "Antiangiogenic tumor therapy," *BioTechniques*, 34(4):1048-1063.
Davis et al., (2003) "Automated quantification of apoptosis after neoadjuvant chemotherapy for breast cancer: early assessment predicts clinical response," *Clin. Cancer Res.*, 9:955-960.
Davis et al., (2003) "Surrogate markers in antiangiogenesis clinical trials," *Brain Journal of Cancer*, 89:8-14.
Davis et al., (2004) "Quantitative Analysis of Biomarkers Defines an Optimal Biological Dose for Recombinant Human Endostatin in Primary Human Tumors," *Clin. Cancer Res.*, 10:33-42.
De Alba et al., (1999) "Prenatal diagnosis on fetal cells obtained from maternal peripheral blood: report of 66 cases," *Prenatal Diagnosis*, 19:934-940.
Denmeade et al., (2003) "Prostate-Specific Antigen Activated Thapsigargin Prodrug as Targeted Therapy for Prostate Cancer," *J Natl Cancer Inst.*, 95(13):990-1000.

(56) References Cited

OTHER PUBLICATIONS

Di Naro et al., (2000) "Prenatal diagnosis of β-thalassaemia using fetal erythroblasts enriched from maternal blood by a novel gradient," *Mol. Human Reproduction*, 6(6):571-574.
Di Pinto et al., (2005) "A Collagenase-Targeted Multiplex PCR Assay for Identification of *Vibrio alginolyticus, Vibrio cholerae*, and *Vibrio parahaemolyticus*," *J. Food Prot.*, 68(1):150-153.
Dieffenbach, C. W. and G. S. Dveksler, eds., (1995) "PCR Primer: A Laboratory Manual," *Cold Spring Harbor Laboratory Press*: Plainview, NY, pp. 131-155, 193-202, 235-248, 287-409, 507-536 (plus cover and copyright pages).
Diehl and Diaz Jr., (2007) "Digital quantification of mutant DNA in cancer patients," *Curr. Opin. Oncol.* 19:36-42.
Dietmaier et al. (1999) "Multiple mutation analyses in single tumor cells with improved whole genome amplification" *American Journal of Pathology* 154(1): 83-95.
Dirks et al., (2003) "Visualizing RNA molecules inside the nucleus of living cells," *Methods*, 29:51-57.
Dmitrieva et al., (2003) "High NaCl causes Mre11 to leave the nucleus, disrupting DNA damage signaling and repair," *Am. J. Physiol. Renal. Physiol.*, 285:F266-274.
Dmitrieva et al., (2004) "Cells adapted to high NaCl have many DNA breaks and impaired DNA repair both in cell culture and in vivo," *PNAS*, 101(8):2317-2322.
Doyle et al., (2004) "Toll-like Receptors Induce a Phagocytic Gene Program through p38," *J. Exp. Med.*, 199(1):81-90.
Dressman et al., (2003) "Transforming single DNA molecules into fluorescent magnetic particles for detection and enumeration of genetic variations," *PNAS*, 100(15): 8817-22.
Emanuel et al. (1993) "Amplification of specific gene products from human serum," *GATA* 10(6):144-146.
Fan et al. (2001) "Single cell degenerate oligonucleotide primer-PCR and comparative genomic hybridization with modified control reference," *J. of Zhejiang University (Science)* 2(3):318-321.
Fan et al., (2008) "Noninvasive diagnosis of fetal aneuploidy by shotgun sequencing DNA from maternal blood," *PNAS*, 105(42):16266-16271.
Findlay et al. (2001) "Using MF-PCR to diagnose multiple defects from single cells: implications for PGD" *Mol. Cell. Endocrinology* 183:S5-S12.
Fortunel et al., (2003) "Long-term expansion of human functional epidermal precursor cells: promotion of extensive amplification by low TGF-β1 concentrations," *J. Cell Sci.*, 116(19):4043-4052.
Foster et al., (2004) "Laser scanning cytometry for the detection of neoplasia in urologic cytology specimens," *Cancer*, 102:115-123.
Fredriksson et al., (2002) "Protein detection using proximity-dependent DNA ligation assays," *Nat. Biotech.*, 20:473-477.
Furuta et al., (2003) "Phosphorylation of Histone H2AX and Activation of Mre11, Rad50, and Nbs1 in Response to Replication-dependent DNA Double-strand Breaks Induced by Mammalian DNA Topoisomerase I Cleavage Complexes," *J. Biol. Chem.*, 278(22):20303-20312.
Furuya et al., (2004) "A Novel Technology Allowing Immunohistochemical Staining of a Tissue Section with 50 Different Antibodies in a Single Experiment," *J. Histochem. Cytochem.*, 52(2):205-210.
Gardiner et al., (2002) "Spatial and temporal analysis of Rac activation during live neutrophil chemotaxis," *Curr. Biol.*, 12:2029-2034.
Gerstner et al., (2003) "Analysis of ploidy in hypopharyngeal cancer by laser scanning cytometry on fine needle aspirate biopsies," *Anal. Cell. Pathol.*, 25:51-62.
Gerstner et al., (2003) "Slide-based cytometry for predicting malignancy in solid salivary gland tumors by fine needle aspirate biopsies," *Cytometry*, 53B:20-25.
Gerstner et al., (2004) "Eosinophilia in nasal polyposis: its objective quantification and clinical relevance," *Clin. Exp. Allergy*, 34:65-70.
Gerstner et al., (2004) "Quantitative histology by multicolor slide-based cytometry," *Cytometry*, 59A:210-219.

Gibson et al. (1996) "A Novel Method for Real Time Quantitative RT-PCR," *Genome Research* 6(10):995-1001.
Gill et al. (2008) "Nucleic Acid Isothermal Amplification Technologiesa Review," *Nucleosides, Nucleotides, and Nucleic Acids* 27:224-243.
Gillevet et al. (May 2010) "Quantitative Assessment of the Human Gut Microbiome using Multitag Pyrosequencing" *Chem Biodivers.* 7(5):1065-1075 [NIH Public Access, Author Manuscript doi:10.1002/cbdv.200900322 14 pages].
Gniadecki and Rossen, (2003) "Expression ofT-cell activation marker CD134 (0X40) in lymphomatoid papulosis," *Br. J. Dermatol.*, 148:885-891.
Gniadecki, and Bang, (2003) "Flotillas of Lipid Rafts in Transit Amplifying Cell-Like Keratinocytes," *J. Invest. Dermatol.*, 121:522-528.
Greene et al., (2004) "Secretory Leucoprotease Inhibitor Impairs Toll-Like Receptor 2- and 4-Mediated Responses in Monocytic Cells," *Infect. Immun.*, 72(6):3684-3687.
Griffin et al., (2003) "Neutrophil elastase up-regulates human β-defensin-2 expression in human bronchial epithelial cells," *FEBS Lett.*, 546:233-236.
Griffiths, J., (1976) "Colour and Constitution of Organic Molecules," *Academic Press*: London, UK, 1976, Chapters 3 and 9; pp. 55-80, 240-270 (plus cover and copyright pages).
Gross, H.-J. et al., (1995) "Model study detecting breast cancer cells in peripheral blood mononuclear cells at frequencies as low as $10^{-7}$," *PNAS USA*, 92:537-541.
Guatelli et al., (1990) "Isothermal, in vitro amplification of nucleic acids by a multienzyme reaction modeled after retrorvial replication," *Proc. NatL. Acad. Sci. USA*, 87:1874-1878.
Guetta et al. (2004) "Analysis of fetal blood cells in the maternal circulation: challenges, ongoing efforts, and potential solutions," *Stem Cells and Development*, 13:93-99.
Gui and Zheng, (2003) "Epidermal Growth Factor Induction of Phenotype-dependent Cell Cycle Arrest in Vascular Smooth Muscle Cells is through the Mitogen-activated Protein Kinase Pathway," *J. Biol. Chem.*, 278(52):53017-53025.
Gullberg et al., (2004) "Cytokine detection by antibody-based proximity ligation," *Proc. Natl. Acad. Sci. USA*, 101(22):8420-8424.
Guo et al. (2003) "Methodology for using a universal primer to label amplified DNA segments for molecular analysis," *Biotechnology Letters*, 25:2079-2083.
Hahn and Holzgreve, (2002) "Prenatal diagnosis using fetal cells and cell-free fetal DNA in maternal blood: what is currently feasible?," *Clin. Obstetrics and Gynecology*, 45(3):649-56.
Hahn et al., (2000) "Current applications of single-cell PCR," *CMLS, Cell. Mol. Life Sci.*, 57:96-105.
Haider et al., (2003) "Dual Functionality of Cyclooxygenase-2 as a Regulator of Tumor Necrosis Factor-Mediated $G_1$ Shortening and Nitric Oxide-Mediated Inhibition of Vascular Smooth Muscle Cell Proliferation," *Circulation*, 108:1015-1021.
Haider et al., (2003) "In vitro model of "wound healing" analyzed by laser scanning cytometry: Accelerated healing of epithelial cell monolayers in the presence of hyaluronate," *Cytometry*, 53A:1-8.
Hardenbol et al., (2003) "Multiplexed genotyping with sequence-tagged molecular inversion probes," *Nature Biotechnology*, 21(6):673-678.
Hardenbol et al., (2005) "Highly multiplexed molecular inversion probe genotyping: Over 10,000 targeted SNPs genotyped in a single tube assay," *Genome Res.*, 15:269-275.
Haugland, R. P. and K. D. Larison, (1992-1994) eds., *Handbook of Fluorescent Probes and Research Chemicals, 5th Edition, Molecular Probes, Inc.*: Eugene, OR, pp. 1-71, 89-98, 230-234 (plus cover and copyright pages).
Hayden et al. (2008) "Multiplex-Ready PCR: A new method for multiplexed SSR and SNP genotyping" *BMC Genomics* 9(80):12 pages.
Hayden et al. (Feb. 18, 2008) "Multiplex-Ready PCR: A new method for multiplexed SSR and SNP Genotyping," *BMC Genomics*, 9(80):22 pages.

(56) References Cited

OTHER PUBLICATIONS

Heinmöller et al. (2002) "Toward efficient analysis of mutations in single cells from ethanol-fixed, paraffin-embedded, and immunohistochemically stained tissues," *Laboratory Investigation*, 82(4):443-453.

Heitmann et al., (2003) "Solution structure of the matrix attachment region-binding domain of chicken MeCP2," *Eur. J. Biochem.*, 270:3263-3270.

Hennerbichler et al., (2003) "Fetal nucleated red blood cells in peripheral blood of pregnant women: detection and determination of location on a slide using laser-scanning cytometry," *Prenat. Diagn.*, 23:710-715.

Heymach et al., (2004) "Phase II study of the antiangiogenic agent SU5416 in patients with advanced soft tissue sarcomas," *Clin. Cancer Res.*, 10:5732-5740.

Hirabayashi et al., (2004) "The Wnt/β-catenin pathway directs neuronal differentiation of cortical neural precursor cells," *Development*, 131:2791-2801.

Hoffmann et al. (2007) "DNA bar coding and pyrosequencing to identify rare HIV drug resistance mutations," *Nucleic Acids Research*, 35(13):e91, 8pp [Published online Jun. 18, 2007].

Hong et al., (2004) "A nanoliter-scale nucleic acid processor with parallel architecture," *Nature Biotechnology*, 22(4):435-439.

Hong et al., (2006) "Molecular biology on a microfluidic chip," *J. Physics: Condensed Matter*, 18:S691-701.

Hromadnikova et al., (2002) "Quantitative analysis of DNA levels in maternal plasma in normal and Down syndrome pregnancies," *BMC Pregnancy and Childbirth*, 2(4):1-5.

Huang et al., (2003) "DNA Damage Induced by DNA Topoisomerase 1- and Topoisomerase II-Inhibitors Detected by Histone H2AXphosphorylation in Relation to the Cell Cycle Phase and Apoptosis," *Cell Cycle*, 2(6):614-619.

Huang et al., (2004) "Assessment of histone H2AX phosphorylation induced by DNA topoisomerase I and II inhibitors topotecan and mitoxantrone and by the DNA cross-linking agent cisplatin," *Cytometry*, 58A:99-110.

Huang et al., (2004) "Histone H2AX Phosphorylation Induced by Selective Photolysis of BrdU-Labeled DNA with UV Light:Relation to Cell Cycle Phase," *Cytometry*, 62A:1-7.

Huletsky et al., (2004) "New real-time PCR assay for rapid detection of methicillin-resistant *Staphylococcus aureus* directly from specimens containing a mixture of staphylococci," *J. Clin. Microbiol.*, 42(5): 1875-1884.

Isaka et al., (2003) "Chromosomal Variations Within Aneuploid Cancer Lines," *J. Histochem. Cytochem.*, 51(10):1343-1353.

Johnson et al., (2005) "Aluminum-Maltolate Induces Apoptosis and Necrosis in Neuro-2a Cells: Potential Role for p53 Signaling," *Toxicol. Sci.*, 83(2):329-339.

Kamat et al., (2004) "The proteasome inhibitor bortezomib synergizes with gemcitabine to block the growth of human 253JB-V bladder tumors in vivo," *Mol. Cancer Ther.*, 3(3):279-290.

Kang et al., (2003) "Analysis of tyrosine phosphorylation in resident peritoneal cells during diet restriction by laser scanning cytometry," *Shock*, 19(3):238-244.

Kang et al., (2003) "Brief refeeding rapidly reverses dietary restriction-induced nuclear factor-κB downregulation in peritoneal resident cells," *J. Parenteral Enteral Nutrition*, 27(3): 193-197.

Kaper et al. (Apr. 19, 2010) "Parallel preparation of targeted resequencing libraries from 480 genomic regions using multiplex PCR on the Access Array™ system," *AACR 2010 Abstract & presentation*, 3 pages.

Kawamura et al., (2003) "Centrosome hyperamplification and chromosomal instability in bladder cancer," *Eur. Urol.* 43:505-515.

Kawasaki et al., (2003) "11q23-24 loss is associated with chromosomal instability in endometrial cancer," *Int. J. Mol. Med.*, 12:727-731.

Kazakov et al., (1995) "Extraceullular DNA of pregnant women blood," *Tsitologiia*, 37(3):232-6 [Abstract Only in English].

Kimura et al., (2007) "The *DYRK1A* gene, encoded in chromosome 21 Down syndrome critical region, bridges between beta-amyloid production and tau phosphorylation in Alzheimer disease," *Human Molecular Genetics*, 16(1):15-23.

Kirkbright, G. F., (1972) "Fluorescent Indicators," *Indicators*, Pergamon Press: Oxford, UK, Chapter 9, pp. 685-708 (plus cover and copyright pages).

Kita-Matsuo et al. (2005) "Adaptor-tagged competitive polymerase chain reaction: amplification bias and quantified gene expression levels," *Analytical Biochemistry*, 339(1):15-28.

Klein et al., (1999) "Comparative genomic hybridization, loss of heterozygosity, and DNA sequence analysis of single cells," *Proc. Natl. Acad. Sci. USA*, 96:4494-9.

Klein et al., (2009) "Discovery and analysis of differentially expressed genes in single cells and cell populations," *Current Protocols in Molecular Biology, Greene Publishing and Wiley-Interscience*, New York; Chapter 25:25.0.1-25B.8.18, 196pp.

Klein, (2005) "Single cell amplification methods for the study of cancer and cellular ageing," *Mech. Ageing and Dev.*, 126:147-151.

Kobie et al., (2003) "Transforming Growth Factor β Inhibits the Antigen-Presenting Functions and Antitumor Activity of Dendritic Cell Vaccines," *Cancer Res.*, 63:1860-1864.

Kolek et al., (2003) "Antiproliferative and apoptotic effect of TGF-$β_1$ in bovine mammary epithelial BME-UV1 cells," *Camp. Biochem. Physiol.* Part C, 134:417-430.

Kolek et al., (2003) "Co-localization of apoptosis-regulating proteins in mouse mammary epitheliail-HC11 cells exposed to TGF-$β_1$," *Eur. J. Cell Biol.*, 82:303-312.

Koup et al., (1991) "Limiting dilution analysis of cytotoxic T lymphocytes to human immunodeficiency virus *gag* antigens in infected persons: in vitro quantitation of effector cell populations with p17 and p24 specificities" *J. Exp. Med.*, 174(6):1593-1600.

Kranc et al., (2003) "Transcriptional Coactivator Cited2 Induces Bmi1 and Me118 and Controls Fibroblast Proliferation via *Ink4a/ARF*," *Mol. Cell. Biol.*, 23(21):7658-7666.

Kriaucionis and Bird, (2003) "DNA methylation and Rett syndrome," *Hum. Mol. Genet.*, 12(2):R221-R227.

Krivacic et al., (2004) "A rare-cell detector for cancer," *PNAS*, 101 (29): 10501-4.

Kulkarni et al., (2004) "Micropatterning of endothelial cells by guided stimulation with angiogenic factors," *Biosens. Bioelectron.*, 19:1401-1407.

Kurimoto et al., (2006) "An improved single-cell cDNA amplification method for efficient high-density oligonucleotide microarray analysis," *Nucleic Acids Research*, 34(5):e42, 17pp.

Kwoh et al., (1989) "Transcription-based amplification system and detection of amplified human immunodeficiency virus type 1 with a bead-based sandwich hybridization format," *Proc. Natl. Acad. Sci. USA*, 86:1173-1177.

Laboratory Talk (2012) "Isolation and processing of individual cells" 1 page.

Lamas et al., (2003) "Quantitative Fluorescence Imaging Approach for the Study of Polyploidization in Hepatocytes," *J. Histochem. Cytochem.*, 51(3):319-330.

Landegren et al. (1988) "A Ligase-Mediated Gene Detection Technique," *Science*, 241:1077-1080.

Landegren et al., (2004) "Molecular tools for a molecular medicine: analyzing genes, transcripts and proteins using padlock and proximity probes," *J. Mol. Recognit.*, 17:194-977.

Landegren et al., (2003) "Padlock and proximity probes for in situ and array-based analyses: tools for the post-genomic era," *Comparative and Functional Genomics*, 4:525-530.

Leary, J. F. et al., (1999) "Detection and Isolation of Single Tumor Cells Containing Mutated DNA Sequences", *SPIE*, 3603:93-101.

Leuchowius, K-J et al. (2011) "In Situ Proximity Ligation Assay for Microscopy and Flow Cytometry," *Curr. Prot. Cytometry*, Supplement 56, 9:9.36.1-9.36.15.

Life Technologies (Feb. 10, 2011) "Ion Torrent Amplicon Sequencing," 6 Pages.

Lim et al., (Jul. 2003) "Detection of *Helicobacter pylori* in gastric mucosa of patients with gastroduodenal disease by PCR-restriction analysis using the RNA polymerase gene (*rpoB*)," *J. Clin. Micro.*, 41(7):3387-3391.

(56) References Cited

OTHER PUBLICATIONS

Lima and Kueltz, (2004) "Laser scanning cytometry and tissue microarray analysis of salinity effects on killifish chloride cells," *J. Exp. Biol.*, 207:1729-1739.
Lin et al.(Mar. 1996) "Multiplex genotype determination at a large number of gene loci," *PNAS USA*, 93:2582-2587.
Lin et al., (2004) "Evaluation of adipocyte apoptosis by laser scanning cytotnetry," *Int. J. Obesity*, 28:1535-140.
Lo et al., (1989) "Prenatal sex determination by DNA amplification from maternal peripheral blood," *The Lancet*, 2(8676):1363-1365.
Lo et al., (1990) "Detection of single-copy fetal DNA sequence from maternal blood," *The Lancet*, 335:1463-1464.
Lo et al., (1994) "Detection of fetal RhD sequence from peripheral blood of sensitized RhD-negative pregnant women," *British J. of Haematology*, 87:658-660.
Lo et al., (1997) "Presence of fetal DNA in maternal plasma and serum," *The Lancet*, 350:485-487.
Lo et al., (1998) "Quantitative analysis of fetal DNA in maternal plasma and serum: implications for noninvasive prenatal diagnosis," *Am. J. Hum. Genet.* 62:768-775.
Lo, (2000) "Fetal DNA in maternal plasma," *Annals New York Academy of Sciences*, 906:141-147.
Lo et al., (2007) "Digital PCR for the molecular detection of fetal chromosomal aneuploidy," *PNAS*, 104(32): 13116-121.
Lo et al., (2007) "Plasma placental RNA allelic ratio permits noninvasive prenatal chromosomal aneuploidy detection," *Nature Medicine*, 13(2):218-23.
Lo and Chiu, (2007) "Prenatal diagnosis: progress through plasma nucleic acids," *Genetics*, 8:71-77.
Lo, (2009) "Noninvasive prenatal detection of fetal chromosomal aneuploidies by maternal plasma nucleic acid analysis: a review of the current state of the art," *BJOG*, 116:152-7.
Lovmar et al. (2003) "Quantitative evaluation by minisequencing and microarrays reveals accurate multiplexed SNP genotyping of whole genome amplified DNA," *Nucleic Acids Research*, 31(21):(E129)1-9.
Lovmar et al. (2005) "Silhouette scores for assessment of SNP genotype clusters," *BMC Genomics*, 6(1):(35)1-6.
Lun et al., (2008) "Microfluidics digital PCR reveals a higher than expected fraction of fetal DNA in maternal plasma," *Clin. Chem.*, 54(10):1664-1672.
Ma et al., (2003) "E2FBP1/DRIL 1 , an AT-Rich Interaction Domain-Family Transcription Factor, is Regulated by p53," *Mol. Cancer Res.*, 1:438-44.
Maher et al., (Jul. 2003) "Evaluation of Culture Methods and a DNA Probe-Based PCR Assay for Detection of *Campylobacter* Species in Clinical Specimens of Feces," *J. Clin. Micro.*, 41(7):2980-2986.
Makrigiorgos et al. (2002) "A PCR-based amplification method retaining the quantitative difference between two complex genomes," *Nature Biotechnology*, 20: 936-39 (Published online: Aug. 5, 2002, doi:1 0.1 038/nbt724).
Maloney et al., (1999) "Microchimerism of maternal origin persists into adult life," *J. Clin. Invest.*, 104(1):41-47.
Marcus et al., (2006) "Microfluidic single-cell mRNA isolation and analysis," *Anal. Chem.*, 78(9):3084-3089.
Marcus et al., (2006) "Microfluidic single-cell mRNA isolation and analysis," and Supporting information for: Microfluidic single cell mRNA isolation and analysis, *Anal. Chem.*, 78(9):3084-3089 (14 pages).
Marcus et al., (2006) "Parallel picoliter RT-PCR assays using microfluidics," *Anal. Chem.*, 78(3):956-958.
Marcus,(2006) "Single Cell Gene Expression Analysis Using Microfluidics," dissertation, [available at http://thesis.library.caltech.edu/2755/, deposited Jul. 12, 2006]; also entitled "Single mammalian cell gene expression analysis using microfluidics," 179pp.
Margulies et al., (2005) "Genome sequencing in microfabricated high-density picolitre reactors," *Nature*, 437:376-380.
Marras et al., (2003) "Genotyping SNPs with molecular beacons," *Methods in Molecular Biol.*, 212:111-128.

Martin et al., (1992) "A method for using serum or plasma as a source of DNA for HLA typing," *Human Immunology*, 33:108-113.
Martin-Fernandez et al., (2004) "Adenovirus type-5 entry and disassembly followed in living cells by FRET, fluorescence anisotropy, and Flim," *Biophys. J.*, 87:1316-1327.
Maruvada et al., (2004) "Cell cycle-dependent expression of thyroid hormone receptor-β is a mechanism for variable hormone sensitivity," *Mol. Biol. Cell*, 15:1895-1903.
Masiuk et al., (2004) "Simultaneous measurement of nucleolin and estrogen receptor in breast cancer cells by laser scanning cytometry," *Anticancer Res.*, 24:963-966.
Mazur et al., (2003) "Induction of apoptosis in bone marrow cells after treatment of mice with WR-2721 and gamma-rays: relationship to the cell cycle," *Cell Bio. Toxicol.*, 19:13-27.
Medina et al., (2003) "LAV694, a new antiproliferative agent showing improved skin tolerability vs. clinical standards for the treatment of actinic keratosis," *Biochem. Pharmacol.*, 66:1885-1895.
Megyeri et al., (2004) "Laser Scanning Cytometry for selection of green fluorescent protein transgenic mice using small number of blood cells," *J. Biochem. Biophys. Methods*, 61:183-187.
Miyaji et al., (Jan. 1, 1998) "A novel single cell PCR assay: detection of human T lymphotropic virus type 1 DNA in lymphocytes of patients with adult T cell leukemia," Bio-Technical Methods Section (BTS), *Leukemia*, 12:1645-1650 [Retrieved from the Internet on Jan. 20, 2014: URL:http://www.nature.com/leu/journal/v12/n10/pdf/2401154a.pdf].
Miyaji-Yamaguchi et al., (2003) "Involvement of Nucleocytoplasmic Shuttling of Yeast Nap1 in Mitotic Progression," *Mol. Cell. Biol.*, 23(18):6672-668484.
Mocellin et al., (2003) "Use of laser scanning cytometry to study tumor microenvironment," *Histolology Histopathology*, 18:609-615.
Mohamed et al., (2007) "Biochip for separating fetal cells from maternal circulation," *J. of Chromatography*, 1162:187-192.
Mohamed, H. et al., (2006) "A Micromachiens Sparse-Cell Isolation Device: Application in Prenatal Diagnostics," *Nanotech*, 3:641-644.
Mongillo et al, (2004) "Fluorescence resonance energy transfer-based analysis of cAMP dynamics in live neonatal rat cardiac myocytes reveals distinct functions of compartmentalized phosphodiesterases," *Circ. Res.*, 95:1-8.
Moos et al., (2004) "Curcumin impairs tumor suppressor p53 function in colon cancer cells," *Carcinogenesis*, 25(9): 1611-1617.
Morales et al., (2003) "Role for the BRCA1 C-terminal Repeats (BRCT) Protein 53BP1 in Maintaining Genomic Stability," *J. Biol. Chem.* 278(17):14971-14977.
Moshinsky et al., (2003) "A Widely Applicable, High-Throughput TR-FRET Assay for the Measurement of Kinase Autophosphoiylation: VEGFR-2 as a Prototype," *J. of Biomolecular Screening*, pp. 447-452.
Nagrath et al., (2007) "Isolation of rare circulating tumour cells in cancer patients by microchip technology," *Nature*, 450:1235-1241.
Nawrocki et al., (2004) "The proteasome inhibitor bortezomib enhances the activity of docetaxel in ordiotopic human pancreatic tumor xenografts," *Mol. Cancer Ther.*, 3(1):59-70.
Neilan et al. (1997) "A universal procedure for primer labelling of amplicons," *Nucleic Acids Research*, 25(14):2938-2939.
Nelson et al., (2001) "Genotyping fetal DNA by non-invasive means: extraction from maternal plasma," *Vox Sanguinis*, 80:112-116.
Neri et al., (2000) "Transferring Automation for Large-scale Development and Production of Invader™ SNP Assays," *Advances in Nucleic Acid and Protein Analysis*, 3926:117-125.
Ng et al., (2003) "The concentration of circulating corticotropin-releasing hormone mRNA in maternal plasma is increased in preeclampsia," *Clin. Chem.*, 49(5):727-731.
Nilsson et al., (1994) "Padlock probes: circularizing oligonucleotides for localized DNA detection," *Science*, 265:2085-2088.
Nilsson et al., (2006) "Analyzing genes using closing and replicating circles," *Trends in Biotechnol.*, 24(2):83-88.
Nohe and Petersen, (2004) "Analyzing for Co-Localization of Proteins at a Cell Membrane," *Curr. Pharm. Biotechnol.*, 5(2):213-220.

(56) References Cited

OTHER PUBLICATIONS

Oleinik and Krupenko, (2003) "Ectopic Expression of 10-Formyltetrahydrofolate Dehydrogenase in A549 Cells Induces $G_1$ Cell Cycle Arrest and Apoptosis," *Mol. Cancer Res* ., 1:577-88.
Oosterwijk et al., (1998) "Prenatal diagnosis of trisomy 13 on fetal cells obtained from maternal blood after minor enrichment," *Prenatal Diagnosis*, 18:1082-5.
Oswald et al., (2004) "Comparison of Flow Cytometry and Laser Scanning Cytometry for the Analysis of CD34+ Hematopoietic Stem Cells," *Cytometry, Part A*, 57A:100-107.
Oswald et al., (2004) "Mesenchymal Stem Cells Can Be Differentiated Into Endothelial Cells In Vitro," *Stem Cells*, 22:377-384.
Ottesen et al., (2006) "Microfluidic Digital PCR Enables Multigene Analysis of Individual Environment Bacteria," *Science*, 314:1464-1467.
Owen, (1978) "High gradient magnetic separation of erythrocytes," *Biophys. J.*, 22:171-178.
Parameswaran et al. (2007) "A pyrosequencing-tailored nucleotide barcode design unveils opportunities for large-scale sample multiplexing," *Nucleic Acids Research*, 35(19):e130, 31 pages [Published online Oct. 11, 2007].
Pertl and Bianchi, (2001) "Fetal DNA in maternal plasma: emerging clinical applications," *Obstet. Gynecol.*, 98:483-90.
Pesce, A.J. et al., (1971) "Fluorescence Spectroscopy: an Introduction for Biology and Medicine," *Marcel Dekker Inc*.: New York, NY, 1971, Chapters 1-7, 254 pp.
Pfau et al., (2004) "Environmental oxygen tension affects phenotype in cultured bone marrow-derived macrophages," *Am. J. Physiol. Lung Cell Mol. Physiol.*, 286:L354-L362.
Piatek et al., (1998) "Molecular beacon sequence analysis for detecting drug resistance in Mycobacterium tuberculosis," *Nat. Biotechnol.*, 16:359-363.
Picot J. et al., (2012) "Flow cytometry: retrospective, fundamentals and recent instrumentation", *Cytotechnol.* 64:109-130.
Pina-Vaz et al., (2004) "Novel Method Using a Laser Scanning Cytometer for Detection of Mycobacteria in Clinical Samples," *J. Clin. Microbial.*, 42(2):906-908.
Poon and Lo, (2001) "Circulating fetal DNA in maternal plasma," *Clinica Chimica Acta*, 313:151-155.
Pozarowski et al., (2003) "Cell Cycle Effects and Caspase-Dependent and Independent Death of HL-60 and Jurkat Cells Treated with the Inhibitor of NF-κB Parthenolide," *Cell Cycle*, 2:377-383.
Pozarowski et al., (2004) "Simple, Semiautomatic Assay of Cytostatic and Cytotoxic Effects of Antitumor Drugs by Laser Scanning Cytometry: Effects of the Bis-Intercalator WP631 on Growth and Cell Cycle of T-24 Cells," *Cytometry, Part A*, 57A:113-119.
Prieto et al., (2002) "Isolation of fetal nucleated red blood cells from maternal blood in normal and aneuploid pregnancies," *Clin. Chern. Lab. Med.*, 40(7):667-72.
Pullen et al., (2003) "The flame retardants tetrabromobisphenol A and tetrabromobisphenol A-bisallylether suppress the induction of interleukin-2 receptor a chain (CD25) in murine splenocytes," *Toxicology*, 184:11-22.
Purwosunu et al., (2006) "Clinical Potential for Noninvasive Prenatal Diagnosis through Detection of Fetal Cells in Maternal Blood," *Taiwanese J. Obstet. Gynecol.*, 45(1): 10-20.
Rahil et al., (2002) "Rapid detection of common autosomal aneuploidies by quantitative fluorescent PCR on uncultured amniocytes," *European J. of Human Genetics*, 10:462-466.
Reed et al., (Feb. 1, 2004) "Mutation of hCDC4 Leads to Cell Cycle Deregulation of Cyclin E in Cancer," *Cancer Res.*, 64:795-800.
Rettig et al., (Sep. 1, 2005) "Large-scale single-cell trapping and imaging using microwell arrays," *Analytical Chemistry, American Chemical Society*, US, 77(17):5628-5634.
Rickert et al., (2004) "Multiplexed Real-Time PCR Using Univeral Reporters," *Clin. Chem.*, 50(9):1680-1683 (9 pages).
Rickman et al., (2005) "Prenatal diagnosis by array-CGH," *European J. Med. Genetics*, 48:232-240.

Rieber et al. (2004) "Tumor apoptosis induced by ruthenium(11)-ketoconazole is enhanced in nonsusceptible carcinoma by monoclonal antibody to EGF receptor," *Int. J. Cancer*, 112:376-384.
Roth et al., (2003) "Effects of epithelial growth factor receptor (EGFR) kinase inhibitors on genetically reconstituted mouse mammary glands," *Exp. Toxic. Pathol.*, 55:237-245.
Saitou et al., (Jan. 1, 2008) "Single-cell cDNA high-density oligonucleotide microarray analysis: detection of individual cell types and properties in complex biological processes", *Reproductive Biomedicine Online, Reproductive Healthcare Ltd*. GB, 16(1):26-40.
Sakhnini and Khuzaie, (2001) "Magnetic behavior of human erythrocytes at different hemoglobin states," *Eur. Biophys. J.*, 30:467-470.
Samaco et al., (2004) "Multiple pathways regulate MeCP2 expression in normal brain development and exhibit defects in autism-spectrum disorders," *Hum. Mol. Genet.*, 13(6):629-39.
Sambrook et al., (1989) Molecular Cloning: *A Laboratory Manual*, 2nd Ed., pp. 9.50-9.51; 11.46-11.49; 11.55-11.57; 15.55.
Samura et al., (2000) "Female fetal cells in maternal blood: use of DNA polymorphisms to prove origin," *Hum. Genet.*, 107:28-32.
Samura et al., (2001) "Diagnosis of Trisomy 21 in Fetal Nucleated Erythrocytes from Maternal Blood by Use of Short Tandem Repeat Sequences," *Clin. Chem.*, 47(9): 1622-1626.
Santangelo et al., (2004) "Dual FRET molecular beacons for mRNA detection in living cells," *Nucleic Acids Res.*, 32(6)e57:1-9.
Sawasaki et al. (2002) "A cell-free protein synthesis system for high-throughput proteomics," *PNAS*, 99(23):14652-14657.
Schümann et al., (2003) "Parenchymal, But Not Leukocyte, TNF Receptor 2 Mediates T Cell-Dependent Hepatitis in Mice," *J. lmmunol.*, 170:2129-2137.
Schwartz et al., (2003) "Oral cytology assessment by flow cytometry of DNA adducts, aneuploidy, proliferation and apoptosis shows differences between smokers and non-smokers," *Oral Oneal.*, 39:842-854.
Schwartz et al., (2004) "Inhibition of experimental tobacco carcinogen induced head and neck carcinogenesis," *Oral Oneal.*, 40:611-623.
Sellner et al. (2004) "MLPA and MAPH: New Techniques for Detection of Gene Deletion," *Human Mutation*, 23(5):413-419.
"Separation of RNA & DNA by Gel Filtration Chromotagraphy," (1987) EDVO-Kit#204, *Edvotek*, 22 pages.
Shackney et al., (2004) "Intracellular Patterns of Her-2/neu, ras, and Ploidy Abnormalities in Primary Human Breast Cancers Predict Postoperative Clinical Disease-Free Survival," *Clin. Cancer Res.*, 10:3042-3052.
Shackney et al., (2004) "A Suitable Method for Identifying Cell Aggregates in Laser Scanning Cytometry Listmode Data for Analyzing Disaggregated Cell Suspensions Obtained from Human Cancers," *Cytometry, Part B*, 59B:10-23.
Shakhman et al., (2003) "Induction by β-bungarotoxin of apoptosis in cultured hippocainpal neurons is mediated by $Ca^{2+}$-dependent formation of reactive oxygen species," *J. Neurochem.*, 87:598-608.
Shendure and Ji, (2008) "Next-generation DNA sequencing," *Nature Biotechnology*, 26(10):1135-1145.
Shendure et al., (2005) "Accurate Multiplex Polony Sequencing of an Evolved Bacterial Genome," *Science*, 309:1728-1732.
Sherlock et al., (1998) "Assessment of diagnostic quantitative fluorescent multiplex polymerase chain reaction assays performed on single cells," *Ann. Hum. Genet.*, 62:9-23.
Shibata et al., (2004) "Lovastatin inhibits tumor growth and lung metastasis in mouse mammary carcinoma model: a p53-independent mitochondrial-mediated apoptotic mechanism," *Carcinogenesis*, 25(10):1887-1898.
Simpson et al. (1994) "Isolating fetal cells in maternal circulation for prenatal diagnosis," *Prenatal Diagnosis*, 14(13):1229-1242.
Smith et al., (Jun. 10, 2003) "LFA-1-induced T cell migration on ICAM-1 involves regulation of MLCK-mediated attachment and Rock-dependent detachment," *J. Cell Sci.*, 116(15):3123-133.
Smolewska et al., (2003) "Apoptosis of peripheral blood lymphocytes in patients with juvenile idiopathic arthritis," *Ann. Rheum. Dis.*, 62:761-763.

(56) References Cited

OTHER PUBLICATIONS

Smolewski et al., (2003) "Caspase-Mediated Cell Death in Hematological Malignancies: Theoretical Considerations, Methods of Assessment, and Clinical Implications," *Leukemia & Lymphoma*, 44(7): 1089-1104.
Snabes et al. (1994) "Preimplantation Single-Cell Analysis of Multiple Genetic Loci by Whole-Genome Amplification," *Proceedings of the National Academy of Sciences of USA*, 91(13):6181-6185.
Södeberg, O. et al. (2008) "Characterizing proteins and their interactions in cells and tissues using the in situ proximity ligation assay," *Methods*, 45:227-232.
Solinas et al., (2001) "Duplex Scorpion primers in SNP analysis and FRET applications," *Nucleic Acids Research* 29(20):e96 1-9.
Sooknanan and Malek, (1995) "NASBA: a detection and amplification system uniquely suited for RNA," *Bio/Technology*, 13:563-364.
Sparkes et al., (Jul. 2008) "New Molecular Techniques for the Prenatal Detection of Chromosomal Aneuploidy," *J. Obstet. D Gynaecol. Can.*, 30(7):617-621.
Sporel, N. A. and F. C. Kafatos, (1987) "Identification of Genomic Sequences Corresponding to eDNA Clones," *Methods 8 in Enzymology: Guide to Molecular Cloning Techniques, Academic Press, Inc.*: Orlando, FL, 152:588-597 (plus cover and copyright pages).
Strife et al., (2003) "Direct Evidence That Bcr-Abl Tyrosine Kinase Activity Disrupts Normal Synergistic Interactions Between Kit Ligand and Cytokines in Primary Primitive Progenitor Cells," *Mol. Cancer Res.*, 1:176-185.
Stürzenbaum (1999) "Transfer RNA Reduces the Formation of Primer Artifacts During Quantitative PCR," *BioTechniques*, 27:50-52.
Sykes et al., (1992) "Quantitation of targets for PCR by use of limiting dilution," *BioTechniques*, 13(3):444-449.
Szodoray et al., (2003) "Programmed Cell Death in Rheumatoid Arthritis Peripheral Blood T-Cell Subpopulations Determined by Laser Scanning Cytometry," *Lab. Invest.*, 83(12):1839-1848.
Takemoto et al., (2004) "Cell Cycle-dependent Phosphorylation, Nuclear Localization, and Activation of Human Condensin," *J. Biol. Chem.*, 279(6):4551-4559.
Takita et al., (2003) "An Analysis of Changes in the Expression of Cyclins A and B1 by the Cell Array System During the Cell Cycle: Comparison Between Cell Synchronization Methods," *Cytometry, Part A* 55A:24-9.
Tamamori-Adachi et al., (2004) "Down-regulation of p27Kip1 promotes cell proliferation of rat neonatal cardiornyocytes induced by nuclear expression of cyclin Dl and CDK4: Evidence for impaired Skp2-dependent degradation of p27 in terminal differentiation," *J. Biol. Chern.*, 279(48):50429-50436.
Tamamori-Adachi et al., (2003) "Critical Role of Cyclin D1 Nuclear Import in Cardiomyocyte Proliferation," *Circ. Res.*, 92:e12-e19.
Tanaka et al., (2000) "Genome-wide expression profiling of mid-gestation placenta and embryo using a 15,000 mouse developmental cDNA microarray," *PNAS*, 97(16):9127-9132.
Teo et al. (2002) "Reliable and reproducible LightCycler qPCR for HIV-1 DNA 2-LTR circles," *Journal of Immunological Methods*, 270:109-118.
Thelwell et al., (2000) "Mode of action and application of scorpion primers to mutation detection," *Nucleic Acids Research*, 28(19):3752-3761.
Thompson, A.M. et al., (2014) "Microfluidics for single-cell genetic analysis," *Lab on a Chip*, 14:3135-3142.
Thorén et al., (2004) "Membrane binding and translocation of cell penetrating peptides," *Biochemistry*, 43:3471-3489.
Thorsen et al., (Oct. 18, 2002) "Microfluidic Large-Scale Integration," *Science*, 298:580-584.
Troeger et al., (1999) "Approximately half of the erythroblasts in maternal blood are of fetal origin," *Mol. Human Reporduction*, 5(12):1162-1165.
Tyagi and Kramer, (1996) "Molecular beacons: probes that fluoresce upon hybridization," *Nat. Biotechnology*, 14:303-308.

Tyagi et al., (1998) "Multicolor molecular beacons for allele discrimination," *Nature Biotechnology*, 16:49-53.
Uematsu et al. (2001) "Multiplex polymerase chain reaction (PCR) with color-tagged module-shuffling primers for comparing gene expression levels in various cells," *Nucleic Acids Research, Oxford University Press*, GB 29(16): E84(1-6).
Uitto et al., (2003) "Probing the fetal genome: progress in non-invasive prenatal diagnosis," *Trends in Mol. Medicine*, 9(8):339-343.
Unger et al., (2000) "Monolithic microfabricated valves and pumps by multilayer soft lithography," *Science*, 288:113-116.
Valet et al., (2004) "Cytomics-New Technologies: Towards a Human Cytome Project," *Cytometry, Part A*, 59A:167-171.
Vieyra et al., (2003) "Altered Subcellular Localization and Low Frequency of Mutations of ING1 in Human Brain Tumors," *Clin. Cancer Res.*, 9:5952-5961.
Villamarin et al., (2003) "A comparative analysis of the time-dependent antiproliferative effects of daunorubicin and WP631," *Eur. J. Biochem.*, 270:764-770.
Vogelstein and Kinzler, (1999) "Digital PCR," *Proc. Natl. Acad. Sci. USA*, 96:9236-9241.
Vona et al., (2002) "Enrichment, immunomorphological, and genetic characterization of fetal cells circulating in maternal blood," *Am. J. of Pathology*, 160(1):51-58.
Vrettou et al., (2004) "Real-time PCR for single-cell genotyping in sickle cell and thalassemia syndromes as a rapid, accurate, reliable, and widely applicable protocol for preimplantation genetic diagnosis," *Human Mutation*, 23:513-521.
Walker et al., (2003) "Phenotype versus Genotype in Gliomas Displaying Inter- or Intratumoral Histological Heterogeneity," *Clin. Cancer Res.*, 9:4841-4851.
Wang et al. (2003) "Genomic instability and endoreduplication triggered by *RAD17* deletion," *Genes & Dev.*, 17:965-970.
Wang et al., (2003) "Loss of 13q14-q21 and Gain of 5p14-pter in the Progression of Leiomyosarcoma," *Mod. Pathol.*, 16(8):778-785.
Wang et al., (2005) "Allele quantification using molecular inversion probes (MIP)," *Nucleic Acids Research*, 33(21):e183, 1-14.
Wang et al.,(Jan. 2005) "Microfluidic sorting of mammalian cells by optical force switching," *Nature Biotechnology*, 23(1):83-87.
Warren, (2008) "Single-Cell Gene-Expression Analysis by Quantitative RT-PCT," dissertation, [available at http://thesis.library.caltech.edu/2996/, deposited Aug. 7, 2007], 225 pages.
Wells et al. (1999) "Detailed chronlosomal and molecular genetic analysis of single cells by whole genome amplification and comparative genomic hybridisation," *Nucleic Acids Research*, 27(4):1214-1218.
Wheeler et al. (Jul. 15, 2003) "Microfluidic Device for Single-Cell Analysis" *Analytical Chemistry, American Chemical Society*, U.S., 75(14):3581-3586.
White et al. (2011) "High-throughput microfluidic single-cell RT-qPCR," *PNAS USA* 108:13999-14004 plus supplement (15 pages).
White et al., (2009) "Digital PCR provides sensitive and absolute calibration for high throughput sequencing," *BMC Genomics*, 10(116):1-12.
White, C. E. and R. J. Argauer, (1970) Fluorescence Analysis: A Practical Approach, Mercel Dekker, Inc.: New York, NY, Chapters, 1, 3 and 6, pp. 1-9, 30-53, and 102-115 (plus cover and copyright pages).
Williams et al., (2003) "Differential effects of the proteasome inhibitor bortezomib on apoptosis and angiogenesis in human prostate tumor xenografts," *Mol. Cancer Ther.*, 2:835-843.
Wilson et al., (2003) "Detection of *Legionella pneumophila* by real-time PCR for the *mip* gene" *J. Clin. Micro.*, 41(7):3327-3330.
Windbichler et al. (2006) "Isolation of specific RNA-binding proteins using the streptomycin-binding RNA aptamer," *Nature Protocols*, 1(2):638-641.
Wu and Wallace, (1989) "The Ligation Amplification Reaction (LAR)—Amplification of Specific DNA Sequences Using Sequential Rounds of Template-Dependent Ligation," *Genomics* 4:560-569.
Wu et al., (2003) "Telomere Dysfunction: A Potential Cancer Predisposition Factor," *J. Natl. Cancer Inst.*, 95(16):1211-1218.

(56) References Cited

OTHER PUBLICATIONS

Xing et al., (Sep. 15, 2004) "A Three-Dimensional Flow Control Concept for Single-Cell Experiments on a Microship. 1. Cell Selection, Cell Retention, Cell Culture, Cell Balancing, and Cell Scanning," *Analytical Chemistry, American Chemical Society*, U.S., 76(18):5273-5281.

Xiong et al., (2004) "A simple, rapid, high-fidelity and cost-effective PCR-based two-step DNA synthesis method for long gene sequences," *Nucleic Acids Research*, 32(12):e98, 1-10.

Yang et al., (2005) "Rapid Prenatal Diagnosis of Trisomy 21 by Real-time Quantitative Polymerase Chain Reaction with Amplification of Small Tandem Repeats and S100B in Chromosome 21," *Yonsei Medical J.*, 46(2):193-197.

Yellon et al., (2003) "The role of leukocyte traffic and activation in parturition," *Soc. Gynecol. Investig.*, 10:323-338.

Yu et al., (1997) "Objective aneuploidy detection for fetal and neonatal screening using comparative genomic hybridization (CGH)," *Cytometry*, 28:191-197.

Yuan et al., (2004) "The duration of nuclear extracellular signal-regulated kinase 1 and 2 signaling during cell cycle reentry distinguishes proliferation from apoptosis in response to asbestos," *Cancer Res.*, 64:6530-6536.

Zabaglo et al., (2003) "Cell Filtration-Laser Scanning Cytometry for the Characterisation of Circulating Breast Cancer Cells," *Cytometry, Part A*, 55A:102-108.

Zabaglo et al., (2003) "Measurement of Proliferation Marker Ki67 in Breast Tumour FNAs Using Laser Scanning Cytometry in Comparison to Conventional Immunocytochemistry," *Cytometry, Part B*, 56B:55-61.

Zaccolo, (2004) "Use of chimeric fluorescent proteins and fluorescence resonance energy transfer to monitor cellular responses," *Circ. Res.*, 94:866-873.

Zhang et al., (2004) "Detection of Mitochondrial Caspase Activity in Real Time In Situ in Live Cells," *Microsc. Microanal.*, 10:442-448.

Zhang et al., (2004) "High urea and NaCl carbonylate proteins in renal cells in culture and in vivo, and high urea causes 8-oxoguanine lesions in their DNA," *PNAS*, 101(25):9491-9496.

Zheng et al., (2004) "Calphostin-C Induction of Vascular Smooth Muscle Cell Apoptosis Proceeds through Phospholipase D and Microtubule Inhibition," *J. Biol. Chem.*, 279(8):7112-7118.

Zhu et al., (1994) "High-sensitivity capillary electrophoresis of double-stranded DNA fragments using monomeric and dimeric fluorescent intercalating dyes," *Anal. Chem.*, 66:1941-1948.

Zhu et al., (2003) "Single molecule profiling of alternative pre-mRNA splicing," *Science*, 301:836-838.

Zimmermann, (2004) "Molecular diagnosis in prenatal medicine," Ph.D. thesis, 1-160 [166pp].

Zorov et al., (2004) "Examining Intracellular Organelle Function Using Fluorescent Probes: From Animalcules to Quantum Dots," *Circ. Res.*, 95:239-252, Supplementary Material (7 pages).

U.S. Notice of Allowance dated Feb. 9, 2017 issued in U.S. Appl. No. 14/180,262.

U.S. Requirement for Restriction/Election dated Jan. 18, 2017 issued in U.S. Appl. No. 14/723,872.

Canadian Office Action dated Mar. 16, 2017 issued in CA 2,734,868.

Chinese Reexamination Decision [no translation] dated Nov. 10, 2016 issued in CN200980142505.9.

Chinese Fourth Office Action dated Dec. 28, 2016 issued in CN200980142505.9.

Australian Patent Examination Report No. 1 dated Nov. 22, 2016 issued in AU2015242980.

Chinese Third Office Action dated Sep. 13, 2016 issued in CN201410138786.3.

Chinese Third Office Action [description in English] dated Nov. 2, 2016 issued in CN201410139163.8.

European Summons to Attend Oral Proceedings dated Feb. 9, 2017 issued in EP 14 158 911.9.

Korean Office Action dated Aug. 17, 2016 issued in KR 10-2011-7025826.

Chinese Office Action [no Translation] dated Jan. 6, 2017 issued in CN 201280033406.9.

Chinese Fourth Office Action [no translation] dated Jan. 9, 2017 issued in 201080011426.7.

European Second Office Action dated Jan. 26, 2016 issued in EP 10 732 056.6.

European Summons to attend Oral Proceedings dated Nov. 30, 2016 issued in EP 13 181 405.5.

Japanese Office Action (Notification of Reasons of Refusal) dates Feb. 28, 2017 issued in JP 2015-514128.

Yoshimoto et al., (2011) "Development of automated single-cell isolation and analysis system," *The Society for Biotechnology*, 89(2): 72-78 [English Abstract].

\* cited by examiner

SINGLE-PARTICLE ANALYSIS OF PARTICLE POPULATIONS

CROSS-REFERENCE TO RELATED APPLICATIONS

This application claims the benefit of U.S. provisional application No. 61/649,845, filed May 21, 2012, which is hereby incorporated by reference in its entirety.

FIELD OF THE INVENTION

The invention relates to methods useful for analyzing multiple parameters, on a single-particle basis, in a population of particles.

BACKGROUND OF THE INVENTION

Methods for analyzing multiple parameters of individual particles in populations are of interest in a variety of contexts. In particular, the ability to analyze multiple nucleic acids, optionally in combination with one or more other parameters, on a single-cell basis within a cell population is of broad interest to commercial and academic laboratories. Various approaches to achieving this goal suffer from one or more of the following problems: the steps involved are tedious and labor-intensive, large numbers of cells may be required (e.g., on the order of 10,000 or more cells), which may not be available from the sources to be analyzed (such as tissue biopsies), and/or available techniques may be insufficiently reproducible to generate reliable results from the small amounts of target nucleic acids present in individual cells.

SUMMARY OF THE INVENTION

In various aspects, the invention(s) contemplated herein may include, but need not be limited to, any one or more of the following embodiments:

Embodiment 1: A method of assaying single particles in a plurality of particles, said method including: (a) capturing particles of said plurality in separate reaction volumes to produce a plurality of separate reaction volumes containing only one particle each; (b) assaying a plurality of parameters for each particle, wherein said assaying includes: performing a plurality of reactions on each particle in each separate reaction volume to produce a plurality of reaction products for each particle, wherein at least one reaction product includes a nucleotide sequence that is added to a target nucleic acid and that encodes the identity of the reaction volume that was the source of the reaction product; and analyzing the reaction products to obtain said results; and (c) associating results of the assay with each particle to produce a data set including a plurality of parameters for each particle in said plurality of particles that is in a separate reaction volume.

Embodiment 2: The method of embodiment 1, wherein at least one of the parameters is assayed in each separate reaction volume.

Embodiment 3: The method of any preceding embodiment, wherein the contents of the separate reaction volumes are recovered.

Embodiment 4: The method of any preceding embodiment, additionally including optimizing said capturing such that the expected fraction of separate reaction volumes with only one particle each is at least 35% of the total number of separate reaction volumes.

Embodiment 5: The method of any preceding embodiment, additionally including optimizing said capturing such that the expected fraction of separate reaction volumes with only one particle each is at least 50% of the total number of separate reaction volumes.

Embodiment 6: The method of any preceding embodiment, additionally including optimizing said capturing such that the expected fraction of separate reaction volumes with only one particle each is at least 65% of the total number of separate reaction volumes.

Embodiment 7: The method of any preceding embodiment, additionally including optimizing said capturing such that the expected fraction of separate reaction volumes with only one particle each is at least 85% of the total number of separate reaction volumes.

Embodiment 8: The method of any preceding embodiment, wherein the separate reaction volumes are present within individual compartments of a microfluidic device.

Embodiment 9: The method of any of embodiments 1-8, wherein the particles are captured in separate reaction volumes prior to adding one or more reagent(s) for performing said plurality of reactions.

Embodiment 10: The method of any preceding embodiment, wherein the particles are cells.

Embodiment 11: The method of any preceding embodiment, wherein the particles are selected from nucleic acids, proteins, carbohydrates, lipids, and combinations thereof.

Embodiment 12: The method of any preceding embodiment, wherein fewer than 40,000 particles are employed in the method.

Embodiment 13: The method of any preceding embodiment, wherein fewer than 10,000 particles are employed in the method.

Embodiment 14: The method of any preceding embodiment, wherein the number of particles distributed into separate reaction volumes is greater than 10, greater than 100, or greater than 1000.

Embodiment 15: The method of any of embodiments 1-3 or 8-14, wherein said capturing is performed by limiting dilution.

Embodiment 16: The method of embodiment 15, wherein limiting dilution includes: preparing a series of dilutions of particle suspension; distributing particles from each dilution into separate compartments of a microfluidic device; determining the number of particles in each compartment; and selecting the dilution that produces the highest number of compartments including only a single particle for use in capturing single particles in separate reaction volumes.

Embodiment 17: The method of embodiment 16, wherein the number of particles in each compartment is determined by brightfield microscopy or fluorescence microscopy.

Embodiment 18: The method of embodiment 16, wherein a stain, dye, or label is employed to detect the number of particles in each separate reaction volume.

Embodiment 19: The method of embodiment 18, wherein the particles are cells, and the stain, dye, or label is a membrane-permeant stain, dye, or label.

Embodiment 20: The method of embodiment 18, wherein the particles are cells, and a cell membrane-permeant nucleic acid dye is employed to detect the number of cells in each separate reaction volume.

Embodiment 21: The method of embodiment 18, wherein the particles are cells, and the stain, dye, or label is a cell-surface stain, dye, or label.

Embodiment 22: The method of embodiment 18, wherein the particles are cells, and a labeled antibody specific for a cell-surface marker is employed to detect the number of cells in each separate reaction volume.

Embodiment 23: The method of any preceding embodiment, wherein said capturing includes mechanical capture at a plurality of capture sites in a microfluidic device.

Embodiment 24: The method of embodiment 23, wherein each capture site includes: a capture feature sized to contain only one particle; and a drain feature, wherein when the capture feature is not occupied by a particle, the drain feature permits the flow of fluid through the capture site.

Embodiment 25: The method of embodiment 23, wherein the microfluidic device includes a focusing feature to focus particle flow to each capture site.

Embodiment 26: The method of any preceding embodiment, wherein the method includes affinity-based capture and employs a binding partner that binds a particle component.

Embodiment 27: The method of embodiment 26, wherein the binding partner is affixed to a discrete region of the microfluidic device, wherein each discrete region permits binding of only one particle.

Embodiment 28: The method of embodiment 26, wherein said affinity-based capture includes: capture of a support including the binding partner at a plurality of capture sites in a microfluidic device to produce immobilized supports at each capture site, wherein each immobilized support displays the binding partner in a manner that permits binding of only one particle to each immobilized support; and binding of particles to the binding partners on the immobilized supports.

Embodiment 29: The method of embodiment 28, wherein the support is captured by mechanical capture.

Embodiment 30: The method of embodiment 28, wherein each capture site includes: a capture feature sized to contain only one support; and a drain feature, wherein when the capture feature is not occupied by a support, the drain feature permits the flow of fluid through the capture site.

Embodiment 31: The method of embodiment 28, wherein the microfluidic device includes a focusing feature to focus support and/or particle flow to each capture site.

Embodiment 32: The method of any of embodiments 23-25 and 27-31, wherein each capture site is located within a separate compartment of the microfluidic device.

Embodiment 33: The method of embodiment 32, wherein said capturing includes passing a solution including the particles through the compartments of the microfluidic device, whereby 35% or more of the compartments comprise only a single particle.

Embodiment 34: The method of any of the preceding embodiments, wherein the separate reaction volumes are present within individual compartments of a microfluidic device, and the method includes determining the number of particles in each separate reaction volume; and disregarding results from any reaction volumes that contain no particles or contain more than a single particle.

Embodiment 35: The method of any of embodiments 3-34, wherein said recovering includes separately recovering reaction products from separate reaction volumes.

Embodiment 36: The method of any of embodiments 3-34, wherein said recovering includes pooling reaction products from a plurality of separate reaction volumes.

Embodiment 37: The method of any preceding embodiment, wherein at least one assay is selected from detection of a DNA sequence; detection of an RNA sequence; detection of a molecule selected from the group consisting of a protein, carbohydrate, lipid, and any combination thereof; detection of a small molecule; detection of an activity; detection of an ion concentration; detection of an ion potential; and detection of a red-ox potential.

Embodiment 38: The method of any preceding embodiment, wherein the reactions comprise one or more reactions selected from amplification of DNA, digestion of DNA with a nuclease, ligation of DNA, ligation of (an) adaptor sequence(s) onto a DNA molecule, transposase-mediated incorporation of a transposon into a DNA molecule, DNA sequencing, reverse transcription of RNA, amplification of RNA, and digestion of RNA with an RNase.

Embodiment 39: The method of any preceding embodiment, wherein the reactions comprise whole genome amplification and/or whole transcriptome amplification.

Embodiment 40: The method of any preceding embodiment, wherein the at least one reaction product is produced by a reaction including nucleic acid amplification using at least two amplification primers, wherein each amplification primer includes a barcode sequence, and the combination of barcode sequences encodes the identity of the reaction volume that was the source of the reaction product.

Embodiment 41: The method of embodiment 40, wherein the nucleic acid amplification uses a pair of inner primers and a pair of outer primers, wherein: the inner primers comprise: a forward, inner primer including a first nucleotide tag, a first barcode nucleotide sequence, and a target-specific portion; and a reverse, inner primer including a target-specific portion, a first barcode nucleotide sequence, and a second nucleotide tag; and the outer primers comprise: a forward, outer primer including a second barcode nucleotide sequence and a first nucleotide tag-specific portion; and a reverse, outer primer including a second nucleotide tag-specific portion and a second barcode nucleotide sequence; wherein the outer primers are in excess of the inner primers; and the nucleic acid amplification produces an amplicon including 5'-second barcode nucleotide sequence-first nucleotide tag sequence-first barcode nucleotide sequence-target nucleotide sequence-first barcode nucleotide sequence-second nucleotide tag sequence-second barcode nucleotide sequence-3'.

Embodiment 42: The method of embodiment 40, wherein the nucleic acid amplification uses a pair of inner primers, a pair of stuffer primers, and a pair of outer primers, wherein: the inner primers comprise: a forward, inner primer including a first nucleotide tag and a target-specific portion; and a reverse, inner primer including a target-specific portion and a second nucleotide tag; the stuffer primers comprise: a forward, stuffer primer including a third nucleotide tag, a first barcode nucleotide sequence, and a first nucleotide tag-specific portion; and a reverse, stuffer primer including a second nucleotide tag-specific portion, a first barcode nucleotide sequence, a fourth nucleotide tag; and the outer primers comprise: a forward, outer primer including a second barcode nucleotide sequence and a third nucleotide tag-specific portion; and a reverse, outer primer including a fourth nucleotide tag-specific portion and a second barcode nucleotide sequence; wherein the outer primers are in excess of the stuffer primers, which are in excess of the inner primers; and the nucleic acid amplification produces an amplicon including 5'-second barcode nucleotide sequence-third nucleotide tag sequence-first barcode nucleotide sequence-first nucleotide tag sequence-target nucleotide sequence-second nucleotide tag sequence-first barcode nucleotide sequence-fourth nucleotide tag sequence-second barcode nucleotide sequence-3'.

Embodiment 43: The method of embodiment 41, wherein the separate reaction volumes are separate compartments of a microfluidic device, the separate compartments being arranged as an array defined by rows and columns, wherein the combination of the first and second barcodes in each amplicon identifies the row and column of the compartment that was the source of the amplicon.

Embodiment 44: The method of embodiment 43, wherein said recovering includes pooling amplicons from compartments in a row or in a column.

Embodiment 45: The method of embodiment 41, wherein the outer primers additionally comprise first and second primer binding sites that are capable of being bound by DNA sequencing primers, and wherein the nucleic acid amplification produces an amplicon including 5'-first primer binding site-second barcode nucleotide sequence-first nucleotide tag sequence-first barcode nucleotide sequence-target nucleotide sequence-first barcode nucleotide sequence-second nucleotide tag sequence-second barcode nucleotide sequence-second primer binding site-3'.

Embodiment 46: The method of embodiment 45, wherein said analyzing includes sequencing the amplification products.

Embodiment 47: The method of any preceding embodiment, wherein the plurality of reactions is performed on intact particles.

Embodiment 48: The method of any preceding embodiment, wherein the plurality of reactions is performed on disrupted particles.

Embodiment 49: The method of embodiment 48, wherein the plurality of reactions is performed on lysed cells.

Embodiment 50: The method of any preceding embodiment, wherein the particles are treated with an agent that elicits biological response prior to performing the plurality of reactions.

Embodiment 51: The method of any preceding embodiment, wherein the method includes determining the presence or amount of one or more target nucleic acids in or associated with each particle.

Embodiment 52: The method of any preceding embodiment, wherein the method includes determining the copy numbers of one or more DNA molecule(s) in or associated with each particle.

Embodiment 53: The method of any preceding embodiment, wherein the method includes determining the genotype(s) at one or more loci in or associated with each particle.

Embodiment 54: The method of any preceding embodiment, wherein the method includes determining a haplotype for a plurality of loci in or associated with each particle.

Embodiment 55: The method of any preceding embodiment, wherein the method includes determining the expression level(s) of one or more RNA molecule(s) in or associated with each particle.

Embodiment 56: The method of any preceding embodiment, wherein the method includes determining the nucleotide sequence(s) of one or more RNA molecule(s) in or associated with each particle.

Embodiment 57: The method of any preceding embodiment, wherein the method includes determining the expression level(s) of one or more proteins in or associated with each particle.

Embodiment 58: The method of any preceding embodiment, wherein the results of the analysis indicate the presence of: two or more copy number variations that are correlated with a phenotype; two or more mutations that are correlated with a phenotype; or at least one copy number variation and at least on mutation that are, together, correlated with a phenotype.

Embodiment 59: The method of embodiment 58, wherein the phenotype is selected from the group consisting of risk, presence, severity, prognosis, and responsiveness to a specific therapy of a disease.

Embodiment 60: The method of embodiment 59, wherein the phenotype includes resistance to a drug.

Embodiment 61: The method of any preceding embodiment, where the results of analysis indicate the occurrence of genomic recombination.

Embodiment 62: The method of any preceding embodiment, where the results of analysis indicate co-expression of particular splice variants.

Embodiment 63: The method of any preceding embodiment, where the results of analysis indicate co-expression of particular light and heavy chains in B cells.

Embodiment 64: The method of any preceding embodiment, where the results of analysis indicate the presence of a particular pathogen in a particular host cell.

Embodiment 65: A method of isolating a single particle, said method including: capture of a support including a binding partner at a capture site on a substrate to produce an immobilized support at the capture site, wherein the binding partner binds a particle component, and the immobilized support displays the binding partner in a manner that permits binding of only one particle to each immobilized support; and binding of a particle to the binding partner on the immobilized support.

Embodiment 66: The method of embodiment 65, wherein the capture includes mechanical capture of a support.

Embodiment 67: The method of embodiment 65, wherein the capture site includes: a capture feature sized to contain only one support; and a drain feature, wherein when the capture feature is not occupied by a support, the drain feature permits the flow of fluid through the capture site.

Embodiment 68: The method of embodiment 65, wherein the substrate includes a focusing feature to focus flow to each capture site.

Embodiment 69: The method of any of embodiments 65-68, wherein the substrate includes a plurality of capture sites.

Embodiment 70: The method of embodiment 69, wherein each capture site is located within a separate compartment of a microfluidic device.

Embodiment 71: The method of embodiment 70, wherein the method includes passing a solution including the particles through the compartments of the microfluidic device, whereby 35% or more of the compartments comprise only a single particle.

DETAILED DESCRIPTION

Figure 1:
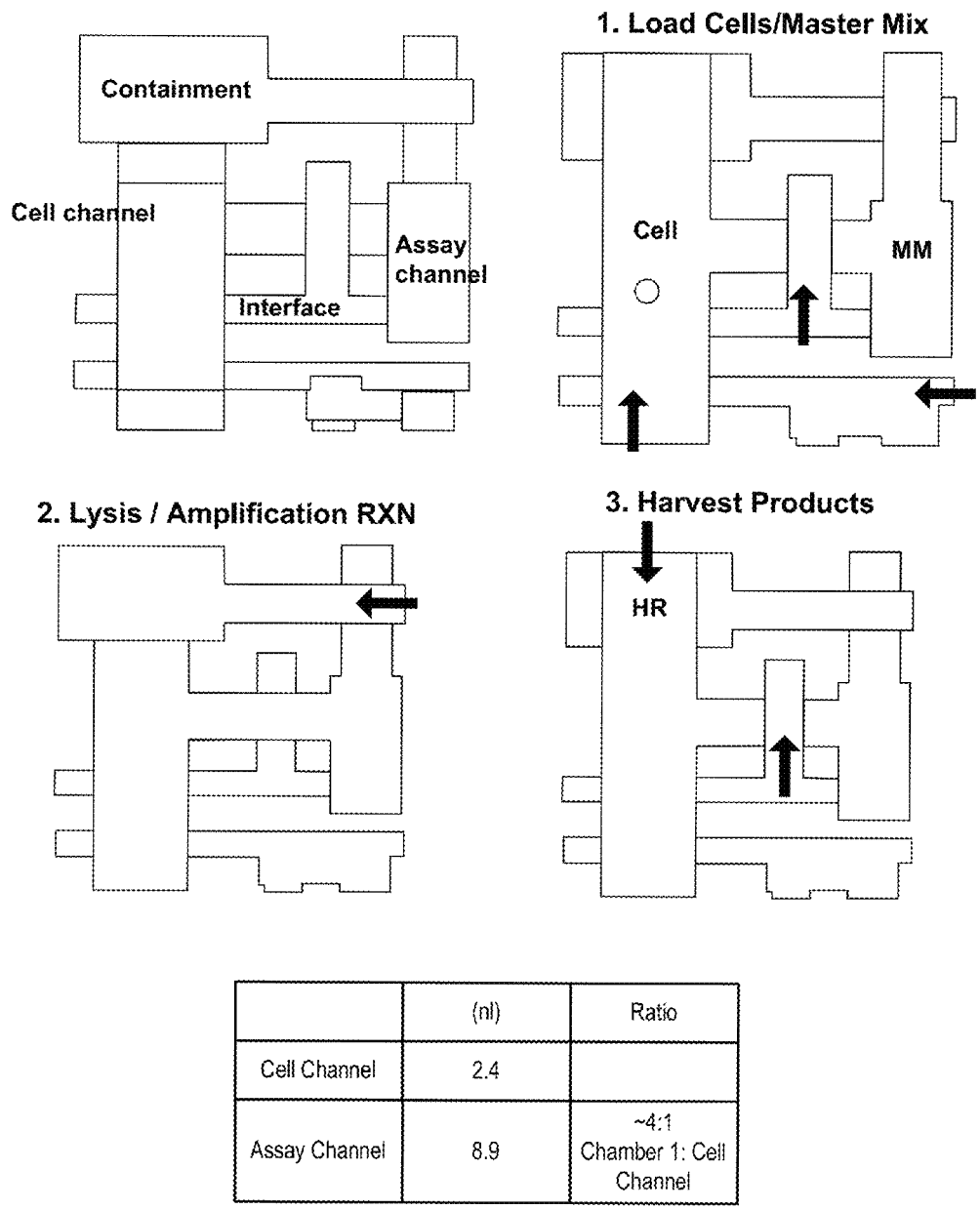
FIG. 1: A schematic diagram of the unit cell architecture for a microfluidic device adapted for Cell handling ("MA006"), showing on-chip processes.

In certain embodiments, the invention provides methods and devices for assaying single particles in a population of particles, wherein at least two parameters are measured for each particle. One or more parameters can be measured while the particles are in the separate reaction volumes. Alternatively or in addition, one or more parameters can be measured in a later analytic step, e.g., where reactions are carried out in the separate reaction volumes and the reaction products are recovered and analyzed. In particular embodiments, one or more parameter measurements are carried out "in parallel," i.e., essentially simultaneously in the separate reaction volumes. This method offers several advantages over measurements taken from the population as a whole. In particular, with the methods described herein, it is possible to measure the parameters, e.g., the expression levels of two genes, in individual cells, as opposed to population measurements, where it is impossible to determine that two genes are expressed in the same cell and/or where expression levels in individual cells cannot be determined. This is helpful for characterizing heterogeneous populations of cells and/or for determining the range of cellular phenotypes within a homogenous population. The ability to associate the results of single-particle analysis with each particle assayed can be exploited where, for example, two or more parameters are associated with a phenotype. The two or more parameters measured can be different types of parameters, e.g., RNA expression level and nucleotide sequence. Further applications of the single-cell analysis methods described herein are described below.

The method entails capturing particles of a population in separate reaction volumes to produce a plurality of separate reaction volumes containing only one particle each. In illustrative embodiments, the separate reaction volumes are present within individual compartments of a microfluidic device, such as, for example, any of those described herein. See also, U.S. Patent Publication No. 2004/0229349, published Nov. 18, 2004, Daridon et al., which is incorporated herein by reference in its entirety and, in particular, for its description of micro-fluidic particle analysis systems. A plurality of parameters is assayed for each particle. The results of the assay are associated with each particle to produce a data set that includes a plurality of parameters for each particle in the population that is in a separate reaction volume. In various embodiments, at least 1, 2, 3, 4, 5, 6, 7, 8, 9, or 10 or more of the parameters is assayed in each separate reaction volume.

In certain embodiments, a parameter is assayed by performing a reaction, such as nucleic acid amplification, in each separate reaction volume to produce one or more reaction products, which is/are analyzed to obtain the results that are then associated with the particle and entered into the data set. The particles may be captured in separate reaction volumes before being contacted with one or more reagent(s) for performing one or more reactions. Alternatively, or in addition, the particles may be contacted with one or more of such reagent(s), and the reaction mixture may be distributed into separate reaction volumes. In various embodiments, at least 2, 3, 4, 5, 6, 7, 8, 9, or 10 or more reactions are performed in each separate reaction volume. The analysis of the reaction products can be carried out in the separate reaction volumes. In some embodiments, however, it is advantageous to recover the contents of the separate reaction volumes for subsequent analysis or other purposes. For example, if a nucleic acid amplification is carried out in the separate reaction volumes, it may be desirable to recover the contents for subsequent analysis, e.g., by PCR and/or nucleic acid sequencing. The contents of the separate reaction volumes may be analyzed separately and the results associated with the particles present in the original reaction volumes. Alternatively, the particle/reaction volume identity can be encoded in the reaction product, e.g., as discussed below with respect to multi-primer nucleic acid amplification methods. Furthermore, these two strategies can be combined so that sets of separate reaction volumes are encoded, such that each reaction volume within the set is uniquely identifiable, and then pooled, with each pool then being analyzed separately.

DEFINITIONS

Terms used in the claims and specification are defined as set forth below unless otherwise specified. These terms are defined specifically for clarity, but all of the definitions are consistent with how a skilled artisan would understand these terms.

The term "nucleic acid" refers to a nucleotide polymer, and unless otherwise limited, includes known analogs of natural nucleotides that can function in a similar manner (e.g., hybridize) to naturally occurring nucleotides.

The term nucleic acid includes any form of DNA or RNA, including, for example, genomic DNA; complementary DNA (cDNA), which is a DNA representation of mRNA, usually obtained by reverse transcription of messenger RNA (mRNA) or by amplification; DNA molecules produced synthetically or by amplification; and mRNA.

The term nucleic acid encompasses double- or triple-stranded nucleic acids, as well as single-stranded molecules. In double- or triple-stranded nucleic acids, the nucleic acid strands need not be coextensive (i.e, a double-stranded nucleic acid need not be double-stranded along the entire length of both strands).

A double-stranded nucleic acid that is not double-stranded along the entire length of both strands has a 5' or 3' extension that is referred to herein as a "sticky end" or as a "tail sequence." The term "sticky end" is often used to refer to a relatively short 5' or 3' extension, such as that produced by a restriction enzyme, whereas the term "tail sequence" is often used to refer to longer 5' or 3' extensions.

The term nucleic acid also encompasses any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

More particularly, in certain embodiments, nucleic acids, can include polydeoxyribonucleotides (containing 2-deoxy-D-ribose), polyribonucleotides (containing D-ribose), and any other type of nucleic acid that is an N- or C-glycoside of a purine or pyrimidine base, as well as other polymers containing normucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. The term nucleic acid also encompasses linked nucleic acids (LNAs), which are described in U.S. Pat. Nos. 6,794,499, 6,670,461, 6,262,490, and 6,770,748, which are incorporated herein by reference in their entirety for their disclosure of LNAs.

The nucleic acid(s) can be derived from a completely chemical synthesis process, such as a solid phase-mediated chemical synthesis, from a biological source, such as through isolation from any species that produces nucleic acid, or from processes that involve the manipulation of nucleic acids by molecular biology tools, such as DNA replication, PCR amplification, reverse transcription, or from a combination of those processes.

The order of elements within a nucleic acid molecule is typically described herein from 5' to 3'. In the case of a double-stranded molecule, the "top" strand is typically shown from 5' to 3', according to convention, and the order of elements is described herein with reference to the top strand.

The term "target nucleic acids" is used herein to refer to particular nucleic acids to be detected in the methods described herein.

As used herein the term "target nucleotide sequence" refers to a molecule that includes the nucleotide sequence of a target nucleic acid, such as, for example, the amplification product obtained by amplifying a target nucleic acid or the cDNA produced upon reverse transcription of an RNA target nucleic acid.

As used herein, the term "complementary" refers to the capacity for precise pairing between two nucleotides. I.e., if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. The degree of complementarity between nucleic acid strands has significant effects on the efficiency and strength of hybridization between nucleic acid strands.

"Specific hybridization" refers to the binding of a nucleic acid to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

In particular embodiments, hybridizations are carried out under stringent hybridization conditions. The phrase "stringent hybridization conditions" generally refers to a temperature in a range from about 5° C. to about 20° C. or 25° C. below than the melting temperature ($T_m$) for a specific sequence at a defined ionic strength and pH. As used herein, the $T_m$ is the temperature at which a population of double-stranded nucleic acid molecules becomes half-dissociated into single strands. Methods for calculating the $T_m$ of nucleic acids are well known in the art (see, e.g., Berger and Kimmel (1987) METHODS IN ENZYMOLOGY, VOL. 152: GUIDE TO MOLECULAR CLONING TECHNIQUES, San Diego: Academic Press, Inc. and Sambrook et al. (1989) MOLECULAR CLONING: A LABORATORY MANUAL, 2ND ED., VOLS. 1-3, Cold Spring Harbor Laboratory), both incorporated herein by reference). As indicated by standard references, a simple estimate of the $T_m$ value may be calculated by the equation: $T_m=81.5+0.41(\% \text{ G}+\text{C})$, when a nucleic acid is in aqueous solution at 1 M NaCl (see, e.g., Anderson and Young, Quantitative Filter Hybridization in NUCLEIC ACID HYBRIDIZATION (1985)). The melting temperature of a hybrid (and thus the conditions for stringent hybridization) is affected by various factors such as the length and nature (DNA, RNA, base composition) of the primer or probe and nature of the target nucleic acid (DNA, RNA, base composition, present in solution or immobilized, and the like), as well as the concentration of salts and other components (e.g., the presence or absence of formamide, dextran sulfate, polyethylene glycol). The effects of these factors are well known and are discussed in standard references in the art. Illustrative stringent conditions suitable for achieving specific hybridization of most sequences are: a temperature of at least about 60° C. and a salt concentration of about 0.2 molar at pH7.

The term "oligonucleotide" is used to refer to a nucleic acid that is relatively short, generally shorter than 200 nucleotides, more particularly, shorter than 100 nucleotides, most particularly, shorter than 50 nucleotides. Typically, oligonucleotides are single-stranded DNA molecules.

The term "adaptor" is used to refer to a nucleic acid that, in use, becomes appended to one or both ends of a nucleic acid. An adaptor may be single-stranded, double-stranded, or may include single- and double-stranded portions.

The term "primer" refers to an oligonucleotide that is capable of hybridizing (also termed "annealing") with a nucleic acid and serving as an initiation site for nucleotide (RNA or DNA) polymerization under appropriate conditions (i.e., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but primers are typically at least 7 nucleotides long and, more typically range from 10 to 30 nucleotides, or even more typically from 15 to 30 nucleotides, in length. Other primers can be somewhat longer, e.g., 30 to 50 nucleotides long. In this context, "primer length" refers to the portion of an oligonucleotide or nucleic acid that hybridizes to a complementary "target" sequence and primes nucleotide synthesis. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target nucleic acid to which a primer hybridizes.

A primer is said to anneal to another nucleic acid if the primer, or a portion thereof, hybridizes to a nucleotide sequence within the nucleic acid. The statement that a primer hybridizes to a particular nucleotide sequence is not intended to imply that the primer hybridizes either completely or exclusively to that nucleotide sequence. For example, in certain embodiments, amplification primers used herein are said to "anneal to a nucleotide tag." This description encompasses primers that anneal wholly to the nucleotide tag, as well as primers that anneal partially to the nucleotide tag and partially to an adjacent nucleotide sequence, e.g., a target nucleotide sequence. Such hybrid primers can increase the specificity of the amplification reaction.

As used herein, the selection of primers "so as to avoid substantial annealing to the target nucleic acids" means that primers are selected so that the majority of the amplicons detected after amplification are "full-length" in the sense that they result from priming at the expected sites at each end of the target nucleic acid, as opposed to amplicons resulting from priming within the target nucleic acid, which produces shorter-than-expected amplicons. In various embodiments, primers are selected to that at least 55%, at least 60%, at least 65%, at least 70%, at least 75%, at least 80%, at least 85%, at least 90%, at least 95%, at least 96%, at least 97%, at least 98%, or at least 99% are full-length.

The term "primer pair" refers to a set of primers including a 5' "upstream primer" or "forward primer" that hybridizes with the complement of the 5' end of the DNA sequence to be amplified and a 3' "downstream primer" or "reverse primer" that hybridizes with the 3' end of the sequence to be amplified. As will be recognized by those of skill in the art, the terms "upstream" and "downstream" or "forward" and "reverse" are not intended to be limiting, but rather provide illustrative orientation in particular embodiments.

In embodiments in which two primer pairs are used, e.g., in an amplification reaction, the primer pairs may be denoted "inner" and "outer" primer pairs to indicate their relative position; i.e., "inner" primers are incorporated into the reaction product (e.g., an amplicon) at positions in between the positions at which the outer primers are incorporated.

In embodiments in which three primer pairs are used, e.g., in an amplification reaction, the term "stuffer primer" can be used to refer to a primer that has a position in between inner and outer primers; i.e., the "stuffer" primer is incorporated into the reaction product (e.g., an amplicon) at positions intermediate between the inner and outer primers.

A "probe" is a nucleic acid capable of binding to a target nucleic acid of complementary sequence through one or more types of chemical bonds, generally through complementary base pairing, usually through hydrogen bond formation, thus forming a duplex structure. The probe binds or hybridizes to a "probe binding site." The probe can be labeled with a detectable label to permit facile detection of the probe, particularly once the probe has hybridized to its complementary target. Alternatively, however, the probe may be unlabeled, but may be detectable by specific binding with a ligand that is labeled, either directly or indirectly. Probes can vary significantly in size. Generally, probes are at least 7 to 15 nucleotides in length. Other probes are at least 20, 30, or 40 nucleotides long. Still other probes are somewhat longer, being at least 50, 60, 70, 80, or 90 nucleotides long. Yet other probes are longer still, and are at least 100, 150, 200 or more nucleotides long. Probes can also be of any length that is within any range bounded by any of the above values (e.g., 15-20 nucleotides in length).

The primer or probe can be perfectly complementary to the target nucleic acid sequence or can be less than perfectly complementary. In certain embodiments, the primer has at least 65% identity to the complement of the target nucleic acid sequence over a sequence of at least 7 nucleotides, more typically over a sequence in the range of 10-30 nucleotides, and often over a sequence of at least 14-25 nucleotides, and more often has at least 75% identity, at least 85% identity, at least 90% identity, or at least 95%, 96%, 97%. 98%, or 99% identity. It will be understood that certain bases (e.g., the 3' base of a primer) are generally desirably perfectly complementary to corresponding bases of the target nucleic acid sequence. Primer and probes typically anneal to the target sequence under stringent hybridization conditions.

The term "nucleotide tag" is used herein to refer to a predetermined nucleotide sequence that is added to a target nucleotide sequence. The nucleotide tag can encode an item of information about the target nucleotide sequence, such the identity of the target nucleotide sequence or the identity of the sample from which the target nucleotide sequence was derived. In certain embodiments, such information may be encoded in one or more nucleotide tags, e.g., a combination of two nucleotide tags, one on either end of a target nucleotide sequence, can encode the identity of the target nucleotide sequence.

The term "transposon end" refers to an oligonucleotide that is capable of being appended to a nucleic acid by a transposase enzyme.

As used herein the term "barcode primer" refers to a primer that includes a specific barcode nucleotide sequence that encodes information about the amplicon produced when the barcode primer is employed in an amplification reaction. For example, a different barcode primer can be employed to amplify one or more target sequences from each of a number of different samples, such that the barcode nucleotide sequence indicates the sample origin of the resulting amplicons.

As used herein, the term "encoding reaction" refers to reaction in which at least one nucleotide tag is added to a target nucleotide sequence. Nucleotide tags can be added, for example, by an "encoding PCR" in which the at least one primer includes a target-specific portion and a nucleotide tag located on the 5' end of the target-specific portion, and a second primer that includes only a target-specific portion or a target-specific portion and a nucleotide tag located on the 5' end of the target-specific portion. For illustrative examples of PCR protocols applicable to encoding PCR, see pending WO Application US03/37808 as well as U.S. Pat. No. 6,605,451. Nucleotide tags can also be added by an "encoding ligation" reaction that can include a ligation reaction in which at least one primer includes a target-specific portion and nucleotide tag located on the 5' end of the target-specific portion, and a second primer that includes a target-specific portion only or a target-specific portion and a nucleotide tag located on the 5' end of the target specific portion. Illustrative encoding ligation reactions are described, for example, in U.S. Patent Publication No. 2005/0260640, which is hereby incorporated by reference in its entirety, and in particular for ligation reactions.

As used herein an "encoding reaction" can produce a "tagged target nucleotide sequence," which includes a nucleotide tag linked to a target nucleotide sequence.

As used herein with reference to a portion of a primer, the term "target-specific" nucleotide sequence refers to a sequence that can specifically anneal to a target nucleic acid or a target nucleotide sequence under suitable annealing conditions.

As used herein with reference to a portion of a primer, the term "nucleotide tag-specific nucleotide sequence" refers to a sequence that can specifically anneal to a nucleotide tag under suitable annealing conditions.

Amplification according to the present teachings encompasses any means by which at least a part of at least one target nucleic acid is reproduced, typically in a template-dependent manner, including without limitation, a broad range of techniques for amplifying nucleic acid sequences, either linearly or exponentially. Illustrative means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. No. 6,027,998; U.S. Pat. No. 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html-); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18- (2002); Lage et al., Genome Res. 2003 February; 13(2):294-307, and Landegren et al., Science 241:1077-80 (1988), Demidov, V., Expert Rev Mol. Diagn. 2002 November; 2(6):542-8., Cook et al., J Microbiol Methods. 2003 May; 53(2):165-74, Schweitzer et al., Curr Opin Biotechnol. 2001 February; 12(1):21-7, U.S. Pat. No. 5,830,711, U.S. Pat. No. 6,027,889, U.S. Pat. No. 5,686,243, PCT Publication No. WO0056927A3, and PCT Publication No. WO9803673A1.

In some embodiments, amplification includes at least one cycle of the sequential procedures of: annealing at least one primer with complementary or substantially complementary sequences in at least one target nucleic acid; synthesizing at least one strand of nucleotides in a template-dependent manner using a polymerase; and denaturing the newly-formed nucleic acid duplex to separate the strands. The cycle may or may not be repeated. Amplification can include thermocycling or can be performed isothermally.

The term "qPCR" is used herein to refer to quantitative real-time polymerase chain reaction (PCR), which is also known as "real-time PCR" or "kinetic polymerase chain reaction."

The term "substantially" as used herein with reference to a parameter means that the parameter is sufficient to provide a useful result. Thus, "substantially complementary," as applied to nucleic acid sequences generally means sufficiently complementary to work in the described context. Typically, substantially complementary means sufficiently complementary to hybridize under the conditions employed. In some embodiments described herein, reaction products must be differentiated from unreacted primers.

A "reagent" refers broadly to any agent used in a reaction, other than an analyte (e.g., nucleic acid being analyzed). Illustrative reagents for a nucleic acid amplification reaction include, but are not limited to, buffer, metal ions, polymerase, reverse transcriptase, primers, template nucleic acid, nucleotides, labels, dyes, nucleases, and the like. Reagents for enzyme reactions include, for example, substrates, cofactors, buffer, metal ions, inhibitors, and activators.

The term "universal detection probe" is used herein to refer to any probe that identifies the presence of an amplification product, regardless of the identity of the target nucleotide sequence present in the product.

The term "universal qPCR probe" is used herein to refer to any such probe that identifies the presence of an amplification product during qPCR. In particular embodiments, nucleotide tags can include a nucleotide sequence to which a detection probe, such as a universal qPCR probe binds. Where a tag is added to both ends of a target nucleotide sequence, each tag can, if desired, include a sequence recognized by a detection probe. The combination of such sequences can encode information about the identity or sample source of the tagged target nucleotide sequence. In other embodiments, one or more amplification primers can include a nucleotide sequence to which a detection probe, such as a universal qPCR probe binds. In this manner, one, two, or more probe binding sites can be added to an amplification product during the amplification step of the methods described herein. Those of skill in the art recognize that the possibility of incorporating multiple probe binding sites during preamplification (if carried out) and amplification facilitates multiplex detection, wherein two or more different amplification products can be detected in a given amplification mixture or aliquot thereof.

The term "universal detection probe" is also intended to encompass primers labeled with a detectable label (e.g., a fluorescent label), as well as non-sequence-specific probes, such as DNA binding dyes, including double-stranded DNA (dsDNA) dyes, such as SYBR Green and EVA Green.

The term "target-specific qPCR probe" is used herein to refer to a qPCR probe that identifies the presence of an amplification product during qPCR, based on hybridization of the qPCR probe to a target nucleotide sequence present in the product.

The term "stain", as used herein, generally refers to any organic or inorganic molecule that binds to a component of a reaction or assay mixture to facilitate detection of that component.

The term "dye," as used herein, generally refers to any organic or inorganic molecule that absorbs electromagnetic radiation at a wavelength greater than or equal 340 nm.

The term "label," as used herein, refers to any atom or molecule that can be used to provide a detectable and/or quantifiable signal. In particular, the label can be attached, directly or indirectly, to a nucleic acid or protein. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

The term "fluorescent dye," as used herein, generally refers to any dye that emits electromagnetic radiation of longer wavelength by a fluorescent mechanism upon irradiation by a source of electromagnetic radiation, such as a lamp, a photodiode, or a laser.

The term "elastomer" has the general meaning used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed.

As use herein, the term "variation" is used to refer to any difference. A variation can refer to a difference between individuals or populations. A variation encompasses a difference from a common or normal situation. Thus, a "copy number variation" or "mutation" can refer to a difference from a common or normal copy number or nucleotide sequence. An "expression level variation" or "splice variant" can refer to an expression level or RNA or protein that differs from the common or normal expression level or RNA or protein for a particular, cell or tissue, developmental stage, condition, etc.

A "polymorphic marker" or "polymorphic site" is a locus at which nucleotide sequence divergence occurs. Illustrative markers have at least two alleles, each occurring at frequency of greater than 1%, and more typically greater than 10% or 20% of a selected population. A polymorphic site may be as small as one base pair. Polymorphic markers include restriction fragment length polymorphism (RFLPs), variable number of tandem repeats (VNTR's), hypervariable regions, minisatellites, dinucleotide repeats, trinucleotide repeats, tetranucleotide repeats, simple sequence repeats, deletions, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A "single nucleotide polymorphism" (SNP) occurs at a polymorphic site occupied by a single nucleotide, which is the site of variation between allelic sequences. The site is usually preceded by and followed by highly conserved sequences of the allele (e.g., sequences that vary in less than $\frac{1}{100}$ or $\frac{1}{1000}$ members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele.

As used herein, the term "particle" refers to an entity that can range, in size and complexity, from a molecule to a cell. The term encompasses such molecules as nucleic acids, proteins, carbohydrates, lipids, and combinations thereof (e.g., lipoproteins), as well as viruses, chromosomes, cellular vesicles and organelles, and cells.

The term "capture feature" is used herein to refer to a feature located at a discrete site, termed the "capture site," within a microfluidic device that facilitates capture of a particle. The capture feature can facilitate capture by binding affinity and/or by mechanical capture, or by any other means. In certain embodiments, the capture feature is sized/designed so that only one particle can occupy, or be contained by, the capture feature.

The term "drain feature" is used herein to refer to a feature located in or near a capture site that facilitates fluid flow though the capture site. For example, a capture site may have one or more features such as physical barriers designed to retain a particle in the capture site. A drain feature in the capture site ensures that particle-free fluid can flow through the site at sufficiently low fluidic impedance when the site is empty (i.e., not containing a particle) to enhance the flow of particles toward the capture site, rather than around it.

As used herein, the term focusing feature refers to any feature of a microfluidic device that focuses particle flow to each capture site. The focusing feature can focus particle flow by any suitable means, including one or more physical feature(s) that direct particle flow as desired, vacuum forces, fluid flow in a loop, gravity, centrifugal force, magnetic force, electrical force (e.g., electrophoretic and/or electroosmotic force), and/or optically generated forces, among others.

As used with respect to embodiments that include the capture of a support, the term "support" refers to an insoluble substrate that is suitably shaped and sized to pass through a microfluidic device to a capture site, where the support can be captured.

As used herein with respect to reactions, reaction mixtures, reaction volumes, etc., the term "separate" refers to reactions, reaction mixtures, reaction volumes, etc., where reactions are carried out in isolation from other reactions. Separate reactions, reaction mixtures, reaction volumes, etc. include those carried out in droplets (See, e.g., U.S. Pat. No. 7,294,503, issued Nov. 13, 2007 to Quake et al., entitled "Microfabricated crossflow devices and methods," which is incorporated herein by reference in its entirety and specifically for its description of devices and methods for forming and analyzing droplets; U.S. Patent Publication No. 20100022414, published Jan. 28, 2010, by Link et al., entitled "Droplet libraries," which is incorporated herein by reference in its entirety and specifically for its description of devices and methods for forming and analyzing droplets; and U.S. Patent Publication No. 20110000560, published Jan. 6, 2011, by Miller et al., entitled "Manipulation of Microfluidic Droplets," which is incorporated herein by reference in its entirety and specifically for its description of devices and methods for forming and analyzing droplets.), which may, but need not, be in an emulsion, as well as those wherein reactions, reaction mixtures, reaction volumes, etc. are separated by mechanical barriers, e.g., separate vessels, separate wells of a microtiter plate, or separate compartments of a matrix-type microfluidic device.

Particles

The methods described herein can be used to analyze any type of particle. In certain embodiments, a particle generally includes any object that is small enough to be suspended in a fluid, but large enough to be distinguishable from the fluid. Particles may be microscopic or near-microscopic and may have diameters of about 0.005 to 100 µm, 0.1 to 50 µm, or about 0.5 to 30 µm. Alternatively, or in addition, particles may have masses of about $10^{-20}$ to $10^{-5}$ grams, $10^{-16}$ to $10^{-7}$ grams, or $10^{-14}$ to $10^{-8}$ grams. In certain embodiments, the particle is a particle from a biological source ("a biological particle"). Biological particles include, for example, molecules such as nucleic acids, proteins, carbohydrates, lipids, and combinations or aggregates thereof (e.g., lipoproteins), as well as larger entities, such as viruses, chromosomes, cellular vesicles and organelles, and cells. Particles that can be analyzed as described herein also include those that have an insoluble component, e.g., a bead, to which molecules to be analyzed are attached.

In illustrative embodiments, the particles are cells. Cells suitable for use as particles in the methods described herein generally include any self-replicating, membrane-bounded biological entity or any non-replicating, membrane-bounded descendant thereof. Non-replicating descendants may be senescent cells, terminally differentiated cells, cell chimeras, serum-starved cells, infected cells, non-replicating mutants, anucleate cells, etc. Cells used in the methods described herein may have any origin, genetic background, state of health, state of fixation, membrane permeability, pretreatment, and/or population purity, among other characteristics. Suitable cells may be eukaryotic, prokaryotic, archaeon, etc., and may be from animals, plants, fungi, protists, bacteria, and/or the like. In illustrative embodiments, human cells are analyzed. Cells may be from any stage of organismal development, e.g., in the case of mammalian cells (e.g., human cells), embryonic, fetal, or adult cells may be analyzed. In certain embodiments, the cells are stem cells. Cells may be wild-type; natural, chemical, or viral mutants; engineered mutants (such as transgenics); and/or the like. In addition, cells may be growing, quiescent, senescent, transformed, and/or immortalized, among other states. Furthermore, cells may be a monoculture, generally derived as a clonal population from a single cell or a small set of very similar cells; may be presorted by any suitable mechanism, such as affinity binding, FACS, drug selection, etc.; and/or may be a mixed or heterogeneous population of distinct cell types.

Particles that include membranes (e.g., cells or cellular vesicles or organelles), cell walls, or any other type of barrier separating one or more interior components from the exterior space may be intact or disrupted, partially (e.g., permeabilized) or fully (e.g., to release interior components). Where the particles are cells, fixed and/or unfixed cells may be used. Living or dead, fixed or unfixed cells may have intact membranes, and/or be permeabilized/disrupted membranes to allow uptake of ions, stains, dyes, labels, ligands, etc., and/or be lysed to allow release of cell contents.

One advantage of the methods described herein is that they can be used to analyze virtually any number of particles, including numbers well below the millions of particles required for other methods. In various embodiments, the number of particles analyzed can be about 10, about 50, about 100, about 500, about 1000, about 2000, about 3000, about 4000, about 5000, about 6000, about 7,000, about 8000, about 9,000, about 10,000, about 15,000, about 20,000, about 25,000, about 30,000, about 35,000, about 40,000, about 45,000, about 50,000, about 75,000, or about 100,000. In specific embodiments, the number of particles analyzed can fall within a range bounded by any two values listed above.

Particle Capture

Particles may be captured in separate reaction volumes by any means known in the art or described herein. Particle-containing separate reaction volumes can be formed in droplets, in emulsions, in vessels, in wells of a microtiter plate, or in compartments of a matrix-type microfluidic device. In certain embodiments, a capture feature retains one or more cells at a capture site within separate reaction volume. In preferred embodiments, the capture feature preferentially retains only a single cell at the capture site. In certain preferred embodiments, each capture site is located within a separate compartment of the microfluidic device. The term "separate compartment" is used herein to refer to a compartment that is at least temporarily separate from other compartments within a microfluidic device, such that the compartments can contain separate reaction volumes. Temporary separation can be achieved, e.g., with the use of valves, as in the case of microfluidic devices available from Fluidgm, Inc. (South San Francisco, Calif.). The degree of separation must be such that that assays/reactions can be carried out separately within the compartments. As used herein, the term "capture feature" includes single or plural mechanisms, operating in series and/or in parallel. Capture features may act to overcome the positioning force exerted by fluid flow. Suitable capture features may be based on physical barriers coupled with flow (termed "mechanical capture"), chemical interactions (termed "affinity-based capture), vacuum forces, fluid flow in a loop, gravity, centrifugal forces, magnetic forces, electrical forces (e.g., electrophoretic or electroosmotic forces), and/or optically generated forces, among others.

Capture features may be selective or nonselective. Selective mechanisms may be fractionally selective, that is, retaining less than all (a subset of) inputted particles. Fractionally selective mechanisms may rely at least in part on stochastic focusing features (see below). Alternatively, or in addition, selective mechanisms may be particle-dependent, that is, retaining particles based on one or more properties of the inputted particle, such as size, surface chemistry, density, magnetic character, electrical charge, optical property (such as refractive index), and/or the like.

Mechanical Capture

Mechanical capture may be based at least partially on particle contact with any suitable physical barrier(s) disposed, e.g., in a microfluidic device. Such particle-barrier contact generally restricts longitudinal particle movement along the direction of fluid flow, producing flow-assisted retention. Flow-assisted particle-barrier contact also may restrict side-to-side/orthogonal (transverse) movement. Suitable physical barriers may be formed by protrusions that extend inward from any portion of a channel or other passage (that is, walls, roof, and/or floor). For example, the protrusions may be fixed and/or movable, including columns, posts, blocks, bumps, walls, and/or partially/completely closed valves, among others. Some physical barriers, such as valves, may be movable or regulatable. Alternatively, or in addition, a physical barrier may be defined by a recess(es) (e.g., niches), formed in a channel or other passage, or by a fluid-permeable membrane. Other physical barriers may be formed based on the cross-sectional dimensions of passages. For example, size-selective channels may retain particles that are too large to enter the channels. (Size-selective channels also may be referred to as filter channels, microchannels, or particle-restrictive or particle-selective channels.) Examples 2 and 4 provide illustrative mechanical capture embodiments.

Affinity-Based Capture

Affinity-based capture may retain particles based on one or more chemical interaction(s), i.e., wherein a binding partner binds a particle component. The chemical interactions may be covalent and/or noncovalent interactions, including ionic, electrostatic, hydrophobic, van der Waals, and/or metal coordination interactions, among others. Chemical interactions may retain particles selectively and/or non-selectively. Selective and non-selective retention may be based on specific and/or non-specific chemical interactions between particles and surfaces, e.g., in a microfluidic device.

Specific chemical mechanisms may use specific binding partners (SBPs), for example, with first and second SBPs disposed on particles and device surfaces, respectively. Exemplary SBPs may include biotin/avidin, antibody/antigen, lectin/carbohydrate, etc. SBPs may be disposed locally within microfluidic devices before, during and/or after formation of the devices. For example, surfaces of a substrate and/or a fluid layer component may be locally modified by adhesion/attachment of a SBP member before the substrate and fluid layer component are joined. Alternatively, or in addition, an SBP may be locally associated with a portion of a microfluidic device after the device has been formed, for example, by local chemical reaction of the SBP member with the device (such as one catalyzed by local illumination with light). See also Example 3, which describes an embodiment in which beads bearing an SBP member are mechanically caught at capture sites to display the SBP member for affinity-based capture of particles (i.e., cells).

Non-specific chemical mechanisms may rely on local differences in the surface chemistry of microfluidic devices. Such local differences may be created before, during and/or after microfluidic device formation, as described above. The local differences may result from localized chemical reactions, for example, to create hydrophobic or hydrophilic regions, and/or localized binding of materials. The bound materials may include poly-L-lysine, poly-D-lysine, polyethylenimine, albumin, gelatin, collagen, laminin, fibronectin, entactin, vitronectin, fibrillin, elastin, heparin, keratan sulfate, heparan sulfate, chondroitin sulfate, hyaluronic acid, and/or extracellular matrix extracts/mixtures, among others.

Other Capture Features

Other capture features may be used alternatively, or in addition to, affinity-based or mechanical capture. Some or all of these mechanisms, and/or the mechanisms described above, may rely at least partially on friction between particles and microfluidic device channels or passages to assist retention.

Capture features may be based on vacuum forces, fluid flow, and/or gravity. Vacuum-based capture features may exert forces that pull particles into tighter contact with passage surfaces, for example, using a force directed outwardly from a channel. Application of a vacuum, and/or particle retention, may be assisted by an aperture/orifice in the wall of a channel or other passage. By contrast, fluid flow-based capture features may produce fluid flow paths, such as loops, that retain particles. These fluid flow paths may be formed by a closed channel-circuit having no outlet (e.g., by valve closure and active pumping), and/or by an eddy, such as that produced by generally circular fluid-flow within a recess. Gravity-based capture features may hold particles against the bottom surfaces of passages, thus combining with friction to restrict particle movement. Gravity-based retention may be facilitated by recesses and/or reduced fluid flow rates.

Capture features may be based on centrifugal forces, magnetic forces, and/or optically generated forces. Capture features based on centrifugal force may retain particles by pushing the particle against passage surfaces, typically by exerting a force on the particles that is generally orthogonal to fluid flow. Such forces may be exerted by centrifugation of a microfluidic device and/or by particle movement within a fluid flow path. Magnetic force-based capture features may retain particles using magnetic fields, generated external and/or internal to a microfluidic device. The magnetic field may interact with ferromagnetic and/or paramagnetic portions of particles. For example, beads may be formed at least partially of ferromagnetic materials, or cells may include surface-bound or internalized ferromagnetic particles. Electrical force-based capture features may retain charged particles and/or populations using electrical fields. By contrast, capture features that operate based on optically generated forces may use light to retain particles. Such mechanisms may operate based on the principal of optical tweezers, among others.

Another form of capture feature is a blind-fill channel, where a channel has an inlet, but no outlet, either fixedly or transiently. For example, when the microfluidic device is made from a gas permeable material, such as PDMS, gas present in a dead-end channel can escape, or be forced out of the channel through the gas permeable material when urged out by the inflow of liquid through the inlet. This is a preferred example of blind-filling. Blind-filling can be used with a channel or compartment that has an inlet, and an outlet that is gated or valved by a valve. In this example, blind filling of a gas-filled channel or compartment occurs when the outlet valve is closed while filling the channel or compartment through the inlet. If the inlet also has a valve, that valve can then be closed after the blind fill is complete, and the outlet can then be opened to expose the channel or compartment contents to another channel or compartment. If a third inlet is in communication with the channel or compartment, that third inlet can introduce another fluid, gas or liquid, into the channel or compartment to expel the blind-filled liquid to be expelled from the channel or compartment in a measured amount.

Focusing Features

Particle capture can be enhanced in microfluidic devices with the use of a one or more focusing feature(s) to focus particle flow to each capture site. Focusing features may be categorized without limitation in various ways, for example, to reflect their origins and/or operational principles, including direct and/or indirect, fluid-mediated and/or non-fluid-mediated, external and/or internal, and so on. These categories are not mutually exclusive. Thus, a given focusing feature may position a particle in two or more ways; for example, electric fields may position a particle directly (e.g., via electrophoresis) and indirectly (e.g., via electroosmosis).

The focusing features may act to define particle position longitudinally and/or transversely. The term "longitudinal position" denotes position parallel to or along the long axis of a microfluidic channel and/or a fluid flow stream within the channel. In contrast, the term "transverse position" denotes position orthogonal to the long axis of a channel and/or an associated main fluid flow stream. Both longitudinal and transverse positions may be defined locally, by equating "long axis" with "tangent" in curved channels. Focusing features may act to move particles along a path at any angle, relative to the long axis of a channel and/or flow stream, between longitudinal and transverse flow.

The focusing features may be used alone and/or in combination. If used in combination, the features may be used serially (i.e., sequentially) and/or in parallel (i.e., simultaneously). For example, an indirect mechanism such as fluid flow may be used for rough positioning, and a direct mechanism such as optical tweezers may be used for final positioning.

Direct focusing features generally include any mechanism in which a force acts directly on a particle(s) to position the particle(s) within a microfluidic network. Direct focusing features may be based on any suitable mechanism, including optical, electrical, magnetic, and/or gravity-based forces, among others. Optical focusing features use light to mediate or at least facilitate positioning of particles. Suitable optical focusing features include "optical tweezers," which use an appropriately focused and movable light source to impart a positioning force on particles. Electrical focusing features use electricity to position particles. Suitable electrical mechanisms include "electrokinesis," that is, the application of voltage and/or current across some or all of a microfluidic network, which may, as mentioned above, move charged particles directly (e.g., via electrophoresis) and/or indirectly, through movement of ions in fluid (e.g., via electroosmosis). Magnetic focusing features use magnetism to position particles based on magnetic interactions. Suitable magnetic mechanisms involve applying a magnetic field in or around a fluid network, to position particles via their association with ferromagnetic and/or paramagnetic materials in, on, or about the particles. Gravity-based focusing features use the force of gravity to position particles, for example, to contact adherent cells with a substrate at positions of cell culture.

Indirect focusing features generally include any mechanism in which a force acts indirectly on a particle(s), for example, via fluid, to move the particle(s) within a microfluidic network, longitudinally and/or transversely. Longitudinal indirect focusing features generally may be created and/or regulated by fluid flow along channels and/or other passages. Accordingly, longitudinal focusing features may be facilitated and/or regulated by valves and/or pumps that regulate flow rate and/or path. In some cases, longitudinal focusing features may be facilitated and/or regulated by electroosmotic focusing features. Alternatively, or in addition, longitudinal focusing features may be input-based, that is, facilitated and/or regulated by input mechanisms, such as pressure or gravity-based mechanisms, including a pressure head created by unequal heights of fluid columns.

Transverse indirect focusing features generally may be created and/or regulated by fluid flow streams at channel junctions, laterally disposed regions of reduced fluid flow, channel bends, and/or physical barriers (i.e., baffles). Channel junctions may be unifying sites or dividing sites, based on the number of channels that carry fluid to the sites relative to the number that carry fluid away from the sites. Physical barriers may have any suitable design to direct particle flow toward capture sites. For example, a baffle may extend outward from any channel surface, e.g., at an angle to direct particle flow toward a capture site. Baffle length, angle with the channel surface, and distance from the capture site can be adjusted to enhance particle flow toward the capture site. Baffles may be formed by protrusions that extend inward from any portion of a channel or other passage (that is, walls, roof, and/or floor). For example, the protrusions may be fixed and/or movable, including columns, posts, blocks, bumps, walls, and/or partially/completely closed valves, among others. Some physical barriers, such as valves, may be movable or regulatable.

Figure 14A:
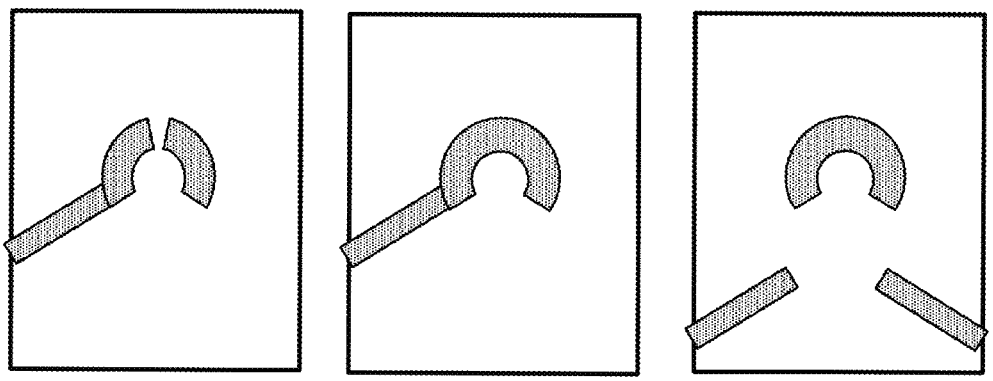
FIG. 14A-C: Capture architectures can be designed to maximize the probability that cells will come into contact with the surface markers. For example, baffles on one or more channel walls can be used to direct beads towards capture feature. (A) Illustrative capture feature/baffle combinations. (B) Performance of the capture feature can be adjusted by adjusting one or more variables, including angle of baffles, distance of baffles from capture site, length of baffles, size and shape of capture feature, size of drain in capture feature (if present). Baffles on the channel wall are used to direct beads towards a capture feature. (C) The capture feature is coupled to a baffle on a channel wall; individual capture feature/baffle combinations can be located on alternate walls to focus flow towards the adjacent capture feature/baffle combination.

In some embodiments, multiple baffles may be employed for each capture site. For example, a baffle extending outward, at an angle, from each lateral wall of a channel can be employed to direct particle flow toward a capture site that is centrally located in the channel. See FIG. 14A-B. Where mechanical capture is employed, baffles may be spaced apart from the physical barrier(s) in the capture sites. Alternatively, or additionally, baffles may contact or be an integral part of the physical barrier(s) in the capture sites. See FIGS. 14A and 14C. For example, a baffle extending outward, at an angle, from a channel wall can contact or be an integral part of a concave capture feature (e.g., physical barrier(s)). It will be appreciated a "concave" capture feature is concave on the side of the capture feature that generally faces the direction of fluid flow. The baffle directs particle flow away from the channel wall and toward the concave capture feature, facilitating particle capture. The next capture site along the path of flow can have a similar baffle-concave capture feature configuration, with the baffle extending from the same wall of the channel. However, it is advantageous, in some embodiments, for the next baffle-concave capture feature to extend from the opposite channel wall. This alternating configuration acts to focus flow from one baffle to the next, whereby flow along each baffle enhances particle flow into each concave capture feature. See FIG. 14C.

Transverse indirect focusing features may be based on laminar flow, stochastic partitioning, and/or centrifugal force, among other mechanisms. Transverse positioning of particles and/or reagents in a microfluidic device may be mediated at least in part by a laminar flow-based mechanism. Laminar flow-based mechanisms generally include any focusing feature in which the position of an input flow stream within a channel is determined by the presence, absence, and/or relative position(s) of additional flow streams within the channel. Such laminar flow-based mechanisms may be defined by a channel junction(s) that is a unifying site, at which inlet flow streams from two, three, or more channels, flowing toward the junction, unify to form a smaller number of outlet flow streams, preferably one, flowing away from the junction. Due to the laminar flow properties of flow streams on a microfluidic scale, the unifying site may maintain the relative distribution of inlet flow streams after they unify as laminar outlet flow streams. Accordingly, particles and/or reagents may remain localized to any selected one or more of the laminar flow streams, based on which inlet channels carry particles and/or reagents, thus positioning the particles and/or reagents transversely. See, e.g., FIG. 16D.

The relative size (or flow rate) and position of each inlet flow stream may determine both position and relative width of flow streams that carry particles and/or reagents. For example, an inlet flow stream for particles/reagents that is relatively small (narrow), flanked by two larger (wider) flow streams, may occupy a narrow central position in a single outlet channel. By contrast, an inlet flow stream for particles/reagents that is relatively large (wide), flanked by a comparably sized flow stream and a smaller (narrower) flow stream, may occupy a wider position that is biased transversely toward the smaller flow stream. In either case, the laminar flow-based mechanism may be called a focusing mechanism, because the particles/reagents are "focused" to a subset of the cross-sectional area of outlet channels. Laminar flow-based mechanisms may be used to individually address particles and/or reagents to plural distinct capture sites.

A laminar flow-based mechanism may be a variable mechanism to vary the transverse position of particles/reagents. As described above, the relative contribution of each inlet flow stream may determine the transverse position of particles/reagents flow streams. Altered flow of any inlet flow stream may vary its contribution to the outlet flow stream(s), shifting particles/reagents flow streams accordingly. In an extreme case, referred to as a perfusion mechanism, a reagent (or particle) flow stream may be moved transversely, either in contact with, or spaced from, retained particles (reagents), based on presence or absence of flow from an adjacent inlet flow stream. Such a mechanism also may be used to effect variable or regulated transverse positioning of particles, for example, to direct particles to capture sites having different transverse positions.

Transverse positioning of particles and/or reagents in a microfluidic device may be mediated at least in part by a stochastic (or portioned flow) focusing feature. Stochastic transverse focusing features generally include any focusing feature in which an at least partially randomly selected subset of inputted particles or reagent is distributed laterally away from a main flow stream to a region of reduced fluid flow within a channel (or, potentially, to a distinct channel). The region of reduced flow may promote particle retention, treatment, detection, minimize particle damage, and/or promote particle contact with a substrate. Stochastic focusing features may be determined by dividing flow sites and/or locally widened channels, among others.

Dividing flow sites may effect stochastic positioning by forming regions of reduced fluid flow rate. Dividing flow sites generally include any channel junction at which inlet flow streams from one (preferably) or more inlet channels are divided into a greater number of outlet channels, including two, three, or more, channels. Such dividing sites may deliver a subset of particles, which may be selected stochastically and/or based on a property of the particles (such as mass), to a region of reduced flow rate or quasi-stagnant flow formed at or near the junction. The fraction of particles represented by the subset may be dependent upon the relative flow directions of the outlet channels relative to the inlet channels. These flow directions may be generally orthogonal to an inlet flow stream, being directed in opposite directions, to form a "T-junction." Alternatively, outlet flow directions may form angles of less than and/or greater than 90 degrees.

The dividing-flow focusing feature, with two or more outlet channels, may be used as a portioned-flow mechanism. Specifically, fluid, particles, and/or reagents carried to the channel junction may be portioned according to fluid flow through the two or more outlet channels. Accordingly, the fractional number or volume of particles or reagent that enters the two or more channels may be regulated by the relative sizes of the channels and/or the flow rate of fluid through the channels, which in turn may be regulated by valves, or other suitable flow regulatory-mechanisms. In a first set of embodiments, outlet channels may be of very unequal sizes, so that only a small fraction of particle and/or reagents are directed to the smaller channel. In a second set of embodiments, valves may be used to forms desired dilutions of reagents. In a third set of embodiments, valves may be used to selectively direct particles to one of two or more fluid paths.

Locally widened channels may promote stochastic positioning by producing regions of decreased flow rate lateral to a main flow stream. The decreased flow rate may deposit a subset of inputted particles at a region of decreased flow rate. Such widened channels may include nonlinear channels that curve or bend at an angle. Alternatively, or in addition, widened regions may be formed by recesses formed in a channel wall(s), chambers that intersect channels, and/or the like, particularly at the outer edge of a curved or bent channel.

Transverse positioning of particles and/or reagents also may be mediated at least in part by a centrifugal focusing feature. In centrifugal focusing features, particles may experience a centrifugal force determined by a change in velocity, for example, by moving through a bend in a fluid path. Size and/or density of particles may determine the rate of velocity change, distributing distinct sizes and/or densities of particle to distinct transverse positions.

Drain Features

In certain embodiments, the capture site also includes a drain feature. Where mechanical capture is employed, for example, the drain feature can include one or more interruptions in a capture feature that is/are sized to permit fluid flow, but not particle flow, through and/or around the capture feature. Thus, for example, the capture feature can include two physical barriers, separated by a space (the drain feature), wherein the space is sufficiently large to permit particle-free fluid to flow between the barriers with sufficiently low impedance to direct cells toward the barriers, thereby enhancing the probability of particle capture. The space between the physical barriers should generally be sufficiently small and/or suitably configured such that the particles to be captured at the capture site will not pass between the barriers. In a specific, illustrative embodiment, the capture feature includes two concave physical barriers, with first and second ends, wherein the barriers are arranged with a small space between first ends of the barriers, forming a drain feature, and a larger space between the second ends of the barriers. See FIG. 14B (where d3 is greater than d1, which forms a drain). In this configuration, the barriers form a "cup" suitably sized to capture a particle, with a drain at the base of the cup. By virtue of the drain, particles flow toward the cup, as long as it is unoccupied. Once a particle flows into the cup, the drain is "plugged," which tends to enhance particle flow around the cup and on to the next capture feature in the microfluidic device.

Non-Optimized Single-Particle Capture

In particular embodiments, a capture technique, such as limiting dilution is used to capture particles in separate reaction volumes. In this type of capture, there is no use of any capture feature, such as binding affinity or a mechanical feature(s), e.g., in a microfluidic device, that preferentially retains only a single cell at a capture site. For example, limiting dilution can be carried out by preparing a series of dilutions of a particle suspension, and distributing aliquots from each dilution into separate reaction volumes. The number of particles in each reaction volume is determined, and the dilution that produces the highest fraction of reaction volumes having only a single particle is then selected and used to capture particles for the parameter measurements described herein.

Optimized Single-Particle Capture

In some embodiments, the methods entail the use of an optimized capture technique to increase the expected fraction of separate reaction volumes having only one particle above that achieved using a method such as limiting dilution (i.e., above about 33 percent). In variations of these embodiments, capturing is optimized such that the expected fraction of separate reaction volumes with only one particle each is at least about 35 percent, at least about 40 percent, at least about 45 percent, at least about 50 percent, at least about 55 percent, at least about 60 percent, at least about 65 percent, at least about 70 percent, at least about 75 percent, at least about 80 percent, at least about 85 percent, at least about 90 percent, or at least about 95 percent of the total number of separate reaction volumes. In specific embodiments, the expected fraction of separate reaction volumes with only one particle each falls within a range bounded by any two percentages listed above. The expected fraction of separate reaction volume with only one particle each can be determined by empirical or statistical means, depending on the particular capture technique (e.g., limiting dilution produces reaction volumes having only one particle in a manner consistent with the Poisson distribution). As used herein, the term "optimizing" does not imply that an optimal result is achieved, but merely that some measure is taken to increase the expected fraction of separate reaction volumes with only one particle above about 33 percent. In particular embodiments, optimized single-particle capture can be achieved, for example, using a size-based mechanism that excludes retention of more than one particle at in each reaction volume (capture site).

In certain embodiments, mechanical capture is used alone or in combination with one or more other capture features to preferentially capture a single particle in each separate reaction volume (i.e., each capture site within a microfluidic device). For example, each capture site can include one or more physical barrier(s) sized to contain only one particle. The shape of the physical barrier can be designed to enhance the retention of the particle. For example, where the particles are cells, the physical barrier(s) can be sized and configured to form a concave surface suitable for retaining just one cell. In such embodiments, the physical barrier(s) can be designed so as to permit the flow of fluid through the capture site, when it is not occupied by a cell, and/or the capture site may include a drain feature that facilitates this flow. In particular embodiments, a microfluidic device contains a plurality of suitably sized/configured physical barriers, whereby a plurality of individual particles is retained within the device, one particle being retained by each physical barrier. In illustrative embodiments, the physical barriers can be located within separate compartments within a microfluidic device, one region per compartment. The compartments can be arranged to form an array, such as, for example, the microfluidic arrays available from Fluidigm Corp. (South San Francisco, Calif.) and described herein. See also FIG. 16A-G.

In certain embodiments, affinity-based capture is used alone or in combination with one or more other capture features, e.g., mechanical capture, to preferentially capture a single cell in each separate reaction volume (i.e., each capture site within a microfluidic device). For example, a discrete region of a microfluidic device surface that contains a binding partner for a particle or particle component may be sized so that only one particle can bind to the region, with the binding of subsequent particles blocked by steric hindrance. In particular embodiments, a microfluidic device contains a plurality of suitably sized regions, whereby a plurality of individual particles, one at each region, is retained within the device. In illustrative embodiments, these regions can be located within separate compartments within a microfluidic device, one region per compartment. The compartments can be arranged to form an array, such as, for example, the microfluidic arrays available from Fluidigm Corp. (South San Francisco, Calif.) and described herein.

Figure 15A:
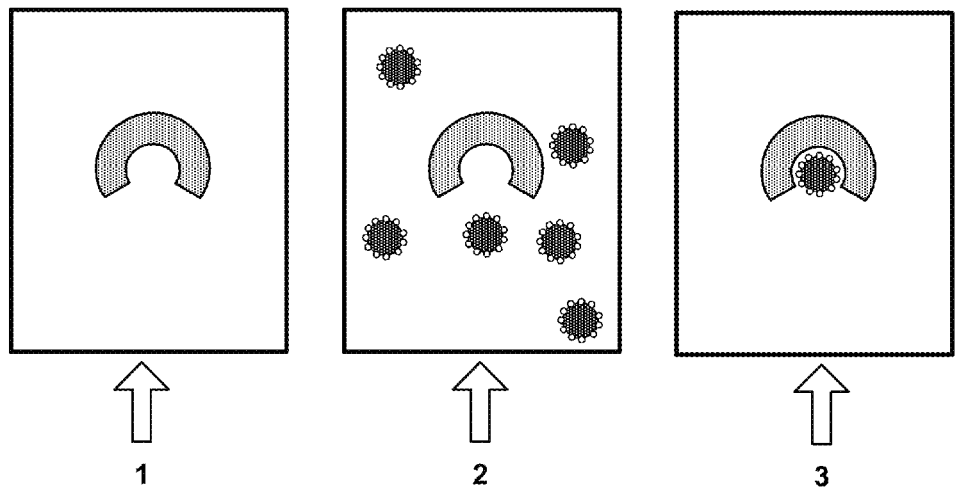
FIG. 15A-B: A strategy for using capture features to catch single, affinity-reagent-coated beads, which then display the affinity reagent (e.g., antibody) so as to capture single particles (e.g., cells). (A-1) Flow is initiated in a channel containing capture features. (A-2) Antibody-bound beads flow toward the capture features until a bead lodges in the capture feature. (A-3) The channel is then washed to remove non-captured beads. (B-1) cells bearing a cell-surface marker to which the antibody binds are flowed into the channel containing the captured beads. (B-2) Cells bearing the marker interact with and bind to antibodies displayed by the captured bead. The display area is sized so that a bound cell will inhibit other cells from interacting with the captured bead through steric occlusion, such that only one cell binds to each captured bead. (B-3) The channel is then washed to remove non-bound cells, leaving one cell immobilized at each capture site.

One approach to affinity-based, optimized single-particle capture is based on capturing a support including a binding partner that binds the particle to be assayed. In illustrative embodiments, the support can be a bead that has the binding partner distributed over its surface. See FIG. 15A. The bead can be captured by mechanical capture using a cup-shaped capture feature to produce a single immobilized support (e.g., bead) at each capture site. In addition to immobilizing the support, the capture feature can, in certain embodiments, reduce the surface area of the support (e.g., bead) that displays the binding partner. This surface can be sufficiently reduced that only one particle can bind to the area of the immobilized support (e.g., bead) that displays the binding partner. To facilitate particle-support binding, in some embodiments, the area of the immobilized support that displays the binding partners faces the flow path of the particles. In specific, illustrative embodiments, a flow channel of a microfluidic device contains a series of capture features. A suspension of beads bearing binding partners (e.g., cell-specific antibodies) is inputted into the channel to produce a series of immobilized beads at the capture sites. The channel is then washed to remove any free (i.e., non-immobilized) beads. FIG. 15A. A cell suspension is then input into the channel. An individual cell can bind to the portion of each bead that displays binding partners. Each bound cell prevents any other cells from binding to the bead through steric occlusion. Washing of the channel removes unbound cells. See FIG. 15B. Valves in between the capture sites can then be closed to create separate reaction volumes, each containing one capture site with one bound cell. One or more focusing features can be employed to direct bead, as well as, particle flow toward each capture site. Alternatively or in addition, the capture features can each include a drain feature that permits the flow of fluid through the capture site when the capture feature is not occupied by a bead.

Determination of Number of Particles Captured

In certain embodiments, it is advantageous to determine the number of particles in each separate reaction volume. This determination can be made when using limiting dilution to identify the dilution that produces the highest fraction of compartments having only a single particle. This determination can also be made after any capture technique to identify those reaction volumes that contain only one particle. For example, in some embodiments, the assay results can be sorted into multiple "bins," based on whether they come from reaction volumes containing 0, 1, 2, or more cells, permitting separate analysis of one or more of these bins.

In some embodiments, the number of particles in each separate reaction volume is determined by microscopy. For example, where the separate reaction volumes are in compartments of a microfluidic device that is sufficiently transparent or translucent, simple brightfield microscopy can be used to visualize and count particles, e.g., cells, per compartment. See Example 1. The microfluidic devices described below and available from Fluidigm Corp. (South San Francisco, Calif.) are suitable for use in this brightfield microscopy approach.

In certain embodiments a stain, dye, or label can be employed to detect the number of particles in each separate reaction volume. Any stain, dye, or label that can be detected in the separate reaction volumes can be used. In illustrative embodiments, a fluorescent stain, dye, or label can be used. The stain, dye, or label employed can be tailored to the particular application. Where the particles are cells, and the parameter to be measured is a feature of the cell surface, the stain, dye, or label can be a cell-surface stain, dye, or label that need not penetrate the cells. For example, a labeled antibody specific for a cell-surface marker can employed to detect the number of cells in each separate reaction volume. Where the particles are cells, and the parameter to be measure is an internal feature of the cell (e.g., nucleic acid), the stain, dye, or label can be a membrane-permeant stain, dye, or label (e.g., a double-stranded DNA binding dye). See Example 1.

Particle Assay

Assay Methods

Particles may be assayed for selected parameters using any suitable assay method, which may be qualitative and/or quantitative. Suitable detection methods may include spectroscopic methods, electrical methods, hydrodynamic methods, imaging methods, and/or biological methods, among others, especially those adapted or adaptable to the analysis of particles. These methods may involve detection of single or multiple values, time-dependent or time-independent (e.g., steady-state or endpoint) values, and/or averaged or (temporally and/or spatially) distributed values, among others. These methods may measure and/or output analog and/or digital values.

Spectroscopic methods generally may include detection of any property of light (or a wavelike particle), particularly properties that are changed via interaction with a sample. Suitable spectroscopic methods may include absorption, luminescence (including photoluminescence, chemiluminescence, and electrochemiluminescence), magnetic resonance (including nuclear and electron spin resonance), scattering (including light scattering, electron scattering, and neutron scattering), diffraction, circular dichroism, and optical rotation, among others. Suitable photoluminescence methods may include fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), fluorescence activated cell sorting (FACS), and their phosphorescence and other analogs, among others.

Electrical methods generally may include detection of any electrical parameter. Suitable electrical parameters may include current, voltage, resistance, capacitance, and/or power, among others.

Imaging methods generally may include detection of spatially distributed signals, typically for visualizing a sample or its components, including optical microscopy and electron microscopy, among others.

Biological methods generally may include detection of some biological activity that is conducted, mediated, and/or influenced by the particle.

Site of Assay

Particle parameters may be assayed at any suitable site. In embodiments employing a microfluidic device, particle parameters may be assayed at a site internal and/or external to the microfluidic device.

Assay sites internal to a microfluidic device may include channels, compartments, and/or traps, and portions thereof. Particles or particle characteristics may be detected while the particles (or released components/assay products) are stationary or moving. Stationary particles may be assayed following particle capture. Moving particles may be assayed before and/or after particle capture. In particular, particles may be moved past a detection site by any suitable positioning mechanism, for example, by fluid flow (flow-based detection).

Suitable external assay sites may include any site(s) away from or independent of a microfluidic device. External assay sites may be used to detect a particle or particle characteristic after removal of particles, particle components, or reaction products from a microfluidic device. One or more of these external sites may be used instead of and/or in addition to internal sites, allowing particles, particle components, or reaction products to be further manipulated and/or analyzed. These further manipulations and/or analysis methods may overlap with, but preferably complement, the manipulations and/or methods performed in the microfluidic device, including mass spectrometry, electrophoresis, centrifugation, PCR, nucleic acid sequencing, and/or cell culture, among others.

Parameters Assayed

The assay method may detect and/or monitor any suitable parameter of a particle, directly and/or indirectly (e.g., via a reporter molecule). Suitable parameters may include particle identity, number, concentration, position (absolute or relative), composition, structure, sequence, and/or activity among others. The detected parameters may include molecular or supramolecular characteristics, such as the presence/absence, concentration, localization, structure (e.g., sequence)/modification, conformation, morphology, activity, number, and/or movement of DNA, RNA, protein, enzyme, lipid, carbohydrate, ions, metabolites, organelles, added reagent, and/or complexes thereof, among others. The detected parameters also may include cellular characteristics, such as any suitable cellular genotype or phenotype, including morphology, growth, apoptosis, necrosis, lysis, alive/dead, position in the cell cycle, activity of a signaling pathway, differentiation, transcriptional activity, substrate attachment, cell-cell interaction, translational activity, replication activity, transformation, heat shock response, motility, spreading, membrane integrity, and/or neurite outgrowth, among others.

Reactions and Assay of Reaction Products

As noted above, in particular embodiments, particle assay can entail performing a plurality of reactions on each particle, or particle components, in each separate reaction volume to produce a plurality of reaction products for each particle. As used in this context, the term "reaction" includes the binding of two binding partners, as well as reactions in which molecules are altered, created, or destroyed. The products of the reaction can then analyzed, qualitatively and/or quantitatively, to yield the results that are then associated with each particle. In certain embodiments, the contents of the separate reaction volumes can be recovered and, optionally, the reaction products subjected to further analysis.

Illustrative reactions include various manipulations of one or more nucleic acids in or associated with the particle. Suitable reactions of this type include, for example, amplification of DNA, digestion of DNA with a nuclease, ligation of DNA, ligation of (an) adaptor sequence(s) onto one or more DNA molecules, transposase-mediated incorporation of a transposon end into a DNA molecule, DNA sequencing, reverse transcription of RNA, amplification of RNA, and digestion of RNA with an RNase. Whole genome amplification and/or whole transcriptome amplification of all of the DNA or RNA, respectively, in or associated with a particle can be carried to generate a representation of the total DNA or total RNA complement of the particle. Although these terms are typically used with respect to the total DNA or RNA complement of a cell, they are used more broadly herein to relate to any particle (e.g., "whole genome amplification" of a chromosome aims to amplify the entire chromosome). In certain embodiments, the reactions carried out in the separate reaction volumes add one or more nucleotide sequences to target nucleic acids, for example, via amplification (see "Multi-Primer Methods for Incorporating Nucleic Acid Sequences into Target Nucleic Acids," below), ligation (e.g., as in ligation of adaptors), or using transposase to incorporate selected transposon ends.

Reagents

Particles may be exposed one or more to reagents before, during, or after parameter measurement. Suitable reagents include any chemical substance(s), compound(s), ion(s), polymer(s), material(s), complex(es), mixture(s), aggregate(s), and/or biological particle(s), among others, that directly or indirectly contacts a particle in any of the methods described herein. Reagents may play a role in particle analysis, including operating as chemical/biological modulators, detection/assay reagents, solvents, buffers, media, washing solutions, and/or so on.

Chemical modulators or biological modulators may include any reagent that is being tested for interaction with particles. Interaction generally includes specific binding to particles and/or any detectable genotypic and/or phenotypic effect on particles (or modulators). Chemical/biological modulators may include ligands that interact with receptors (e.g., antagonists, agonists, hormones, etc.). Ligands may be small molecules, peptides, proteins, carbohydrates, lipids, etc.

Alternatively, or in addition, chemical/biological modulators may be nucleic acids. The nucleic acids may be DNA, RNA, peptide nucleic acids, modified nucleic acids, and/or mixtures thereof, and may be single, double, and/or triple-stranded. The nucleic acids may be produced by chemical synthesis, enzymatic synthesis, and/or biosynthesis, and may be plasmids, fragments, sense/antisense expression vectors, reporter genes, vectors for genomic integration/modification (such as targeting nucleic acids/vectors (for knockout/-down/-in)), viral vectors, antisense oligonucleotides, dsRNA, siRNA, nucleozymes, and/or the like. Nucleic acid reagents may also include transfection reagents to promote uptake of the nucleic acids by cells, such as lipid reagents (e.g., lipofectamine), precipitate-forming agents (such as calcium phosphate), DMSO, polyethylene glycol, viral coats that package the nucleic acids, and/or so on.

Chemical/biological modulators may include miscellaneous chemical materials and/or biological entities. Miscellaneous chemical modulators may be ions (such as calcium, sodium, potassium, lithium, hydrogen (pH), chloride, fluoride, iodide, etc.), dissolved gases (NO, $CO_2$, $O_2$, etc.), carbohydrates, lipids, organics, polymers, etc. In some embodiments, biological modulators may be exposed to cells, for example, to infect cells, to measure cell-cell interactions, etc. Biological modulators may include any cells, viruses, or organelles.

Where the particles are cells, the cells may be pretreated before use in the methods described herein or treated during or after these methods by any suitable processing step(s). Such processing steps may include modulator treatment, transfection (including infection, injection, particle bombardment, lipofection, coprecipitate transfection, etc.), processing with assay reagents, and/or so on.

Reagents employed in the method described herein can include detection/assay reagents. Detection/assay reagents generally include any reagents that are contacted with particles to facilitate processing particles (or particle components) for detection of a preexisting or newly created parameter of the particles (or components). Detection/assay reagents may include stains, dyes, labels, enzymes, substrates, cofactors, and/or specific binding partners (SBPs), among others. Suitable labels may be luminophores, fluorophores, chromogens, chromophores, and/or the like. Stains, dyes, or labels may be conjugated to, or may be, SBPs; may act as enzyme substrates; may inherently label cells or cell structures (e.g., DNA dyes, membrane dyes, trafficking dyes, etc.); may act as indicator dyes (such as calcium indicators, pH indicators, etc.); and/or the like. Enzymes may operate in particle assays by incorporating labels into products and/or by producing a product that may be detected subsequently. Suitable enzymes may include polymerases (RNA and/or DNA), heat-stable polymerases (such as Taq, VENT, etc.), peroxidases (such as HRP), phosphatases (such as alkaline phosphatase), kinases, methylases, ligases, proteases, galactosidases (such as beta-galactosidase, glucuronidase, etc.), transferases (such as chloramphenicol acetyltransferase), oxidoreductases (such as luciferase), and/or nucleases (such as DNAses, RNAses, etc.), among others. SBPs, such as antibodies, digoxigenin, nucleic acids, etc., may be directly conjugated to stains, dyes, labels, enzymes, and/or other SBPs; may be noncovalently bound to dyes, labels, and/or enzymes (either pre-bound or bound in an additional exposure step); and/or so on.

Analysis of Nucleic Acids in Single Particles

In particular embodiments, the methods described herein are used in the analysis of one or more nucleic acids. For example, the presence and/or level of a particular target nucleic acid can be determined, as can a characteristic of the target nucleic acid, e.g., the nucleotide sequence. In illustrative embodiments, a population of particles with one or more sample nucleic acids in or associated with the particle is captured in separate reaction volumes, each preferably containing only a single particle. Reactions, such ligation and/or amplification for DNA, or reverse transcription and/or amplification for RNA are carried out, which produce reaction products for any reaction volume containing one or more target nucleic acids. These reaction products can be analyzed within the reaction volumes, or the reaction volumes can be recovered, separately or in pools, for subsequent analysis, such as DNA sequencing.

In certain embodiments, the reactions incorporate one or more nucleotide sequences into the reaction products. These sequences can be incorporated by any suitable method, including ligation, transposase-mediated incorporation, or amplification using one or more primers bearing one or more nucleotide tags that include the sequence to be incorporated. These incorporated nucleotide sequence(s) can serve any function that facilitates any assay described herein. For example, one or more nucleotide sequences can be incorporated into a reaction product to encode an item of information about that reaction product, such as the identity of the reaction volume that was the source of the reaction product. In this case, the reactions are referred to herein as "encoding reactions." Multi-primer methods for adding "barcode" nucleotide sequences to target nucleic acids can be employed for this purpose and are described below. In specific embodiments, nucleic acid amplification is carried out using at least two amplification primers, wherein each amplification primer includes a barcode nucleotide sequence, and the combination of barcode nucleotide sequences encodes the identity of the reaction volume that was the source of the reaction product (termed "combinatorial barcoding"). These embodiments are conveniently employed when the separate reaction volumes are in separate compartments of a matrix-type microfluidic device, e.g., like those available from Fluidigm Corp. (South San Francisco, Calif.) and described below (see "Microfluidic Devices"). Each separate compartment can contain a combination of barcode nucleotide sequences that identifies the row and column of the compartment in which the encoding reaction was carried out. If the reaction volumes are recovered and subjected to further analysis that includes detection of the barcode combination, the results can be associated with a particular compartment and, thereby, with a particle in the compartment. This association can be carried out for all compartments that contain a single particle to permit single-particle (e.g., single-cell) analysis for a population of particles.

The following sections discuss suitable nucleic acid samples, and within these, target nucleic acids suitable for analysis in the methods described herein. Amplification primer design and illustrative amplification methods are then described. Following this is a description of multi-primer amplification methods for incorporating nucleic acid sequences into target nucleic acids. The remaining sections discuss various labeling strategies and removal of undesired reaction components. These sections are described with respect to methods that employ amplification for incorporating nucleic acid sequences into target nucleic acids and/or analyzing them. However, those of skill in the art will recognize, based on the guidance herein, that amplification is not critical to carrying out many of the methods described herein. For example, nucleic acid sequences can be incorporated by other means, such as ligation or using a transposase.

Sample Nucleic Acids

Preparations of nucleic acids ("samples") can be obtained from biological sources and prepared using conventional methods known in the art. In particular, DNA or RNA useful in the methods described herein can be extracted and/or amplified from any source, including bacteria, protozoa, fungi, viruses, organelles, as well higher organisms such as plants or animals, particularly mammals, and more particularly humans. Suitable nucleic acids can also be obtained from environmental sources (e.g., pond water), from man-made products (e.g., food), from forensic samples, and the like. Nucleic acids can be extracted or amplified from cells, bodily fluids (e.g., blood, a blood fraction, urine, etc.), or tissue samples by any of a variety of standard techniques. Illustrative samples include samples of plasma, serum, spinal fluid, lymph fluid, peritoneal fluid, pleural fluid, oral fluid, and external sections of the skin; samples from the respiratory, intestinal genital, and urinary tracts; samples of tears, saliva, blood cells, stem cells, or tumors. For example, samples of fetal DNA can be obtained from an embryo or from maternal blood. Samples can be obtained from live or dead organisms or from in vitro cultures. Illustrative samples can include single cells, formalin-fixed and/or paraffin-embedded tissue samples, and needle biopsies. Nucleic acids useful in the methods described herein can also be derived from one or more nucleic acid libraries, including cDNA, cosmid, YAC, BAC, Pl, PAC libraries, and the like.

Nucleic acids of interest can be isolated using methods well known in the art, with the choice of a specific method depending on the source, the nature of nucleic acid, and similar factors. The sample nucleic acids need not be in pure form, but are typically sufficiently pure to allow the reactions of interest to be performed. Where the target nucleic acids are RNA, the RNA can be reversed transcribed into cDNA by standard methods known in the art and as described in Sambrook, J., Fritsch, E. F., and Maniatis, T., *Molecular Cloning: A Laboratory Manual.* Cold Spring Harbor Laboratory Press, NY, Vol. 1, 2, 3 (1989), for example.

Target Nucleic Acids

Target nucleic acids useful in the methods described herein can be derived from any of the sample nucleic acids described above. In typical embodiments, at least some nucleotide sequence information will be known for the target nucleic acids. For example, if PCR is employed as the encoding reaction, sufficient sequence information is generally available for each end of a given target nucleic acid to permit design of suitable amplification primers. In an alternative embodiment, target-specific sequences in primers could be replaced by random or degenerate nucleotide sequences.

The targets can include, for example, nucleic acids associated with pathogens, such as viruses, bacteria, protozoa, or fungi; RNAs, e.g., those for which over- or under-expression is indicative of disease, those that are expressed in a tissue- or developmental-specific manner; or those that are induced by particular stimuli; genomic DNA, which can be analyzed for specific polymorphisms (such as SNPs), alleles, or haplotypes, e.g., in genotyping. Of particular interest are genomic DNAs that are altered (e.g., amplified, deleted, rearranged, and/or mutated) in genetic diseases or other pathologies; sequences that are associated with desirable or undesirable traits; and/or sequences that uniquely identify an individual (e.g., in forensic or paternity determinations).

In various embodiments, a target nucleic acid to be amplified can be, e.g., 25 bases, 50 bases, 100 bases, 200 bases, 500 bases, or 750 bases. In certain embodiments of the methods described herein, a long-range amplification method, such as long-range PCR can be employed to produce amplicons from the amplification mixtures. Long-range PCR permits the amplification of target nucleic acids ranging from one or a few kilobases (kb) to over 50 kb. In various embodiments, the target nucleic acids that are amplified by long-range PCR are at least about 1, 2, 3, 4, 5, 6, 7, 8, 9, 10, 11, 12, 13, 14, 15, 20, 25, 30, 35, 40, 45, or 50 kb in length. Target nucleic acids can also fall within any range having any of these values as endpoints (e.g., 25 bases to 100 bases or 5-15 kb).

Primer Design

Primers suitable for nucleic acid amplification are sufficiently long to prime the synthesis of extension products in the presence of the agent for polymerization. The exact length and composition of the primer will depend on many factors, including, for example, temperature of the annealing reaction, source and composition of the primer, and where a probe is employed, proximity of the probe annealing site to the primer annealing site and ratio of primer:probe concentration. For example, depending on the complexity of the target nucleic acid sequence, an oligonucleotide primer typically contains in the range of about 15 to about 30 nucleotides, although it may contain more or fewer nucleotides. The primers should be sufficiently complementary to selectively anneal to their respective strands and form stable duplexes. One skilled in the art knows how to select appropriate primer pairs to amplify the target nucleic acid of interest.

For example, PCR primers can be designed by using any commercially available software or open source software, such as Primer3 (see, e.g., Rozen and Skaletsky (2000) *Meth. Mol. Biol.,* 132: 365-386; www.broad.mit.edu/node/1060, and the like) or by accessing the Roche UPL website. The amplicon sequences are input into the Primer3 program with the UPL probe sequences in brackets to ensure that the Primer3 program will design primers on either side of the bracketed probe sequence.

Primers may be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; the solid support method of U.S. Pat. No. 4,458,066 and the like, or can be provided from a commercial source.

Primers may be purified by using a Sephadex column (Amersham Biosciences, Inc., Piscataway, N.J.) or other methods known to those skilled in the art. Primer purification may improve the sensitivity of the methods described herein.

Amplification Methods

Nucleic acids can be amplified in accordance with the methods described herein for any useful purpose, e.g., to increase the concentration of target nucleic acids for subsequent analysis, and/or to incorporate one or more nucleotide sequences, and/or to detect and/or quantify and/or sequence one or more target nucleic acids. Amplification can be carried out in droplets, in emulsions, in vessels, in wells of a microtiter plate, in compartments of a matrix-type microfluidic device, etc.

Amplification to Increase the Concentration of Target Nucleic Acids

Amplification to increase the concentration of target nucleic acids can be aimed at amplifying all nucleic acids in a reaction mixture, all nucleic acids of a particular type (e.g., DNA or RNA), or specific target nucleic acids. In specific, illustrative embodiments, whole genome amplification can be carried out to increase the concentration of genomic DNA; RNA can be amplified, optionally preceded by a reverse transcription step; and/or general or target-specific preamplification.

Whole Genome Amplification

To analyze genomic DNA, the sample nucleic acids can be amplified using a whole genome amplification (WGA) procedure. Suitable WGA procedures include primer extension PCR (PEP) and improved PEP (1-PEP), degenerated oligonucleotide primed PCR (DOP-PCR), ligation-mediated PCR (LMP), T7-based linear amplification of DNA (TLAD), and multiple displacement amplification (MDA). These techniques are described in U.S. Patent Publication No. 20100178655, published Jul. 15, 2010 (Hamilton et al.), which is incorporated herein by reference in its entirety and specifically for its description of methods useful in single-cell nucleic acid analysis.

Kits for WGA are available commercially from, e.g., Qiagen, Inc. (Valencia, Calif. USA), Sigma-Aldrich (Rubicon Genomics; e.g., Sigma GenomePlex® Single Cell Whole Genome Amplification Kit, PN WGA4-50RXN). The WGA step of the methods described herein can be carried out using any of the available kits according to the manufacturer's instructions.

In particular embodiments, the WGA step is limited WGA, i.e., WGA is stopped before a reaction plateau is reached. Typically, WGA is performed for more than two amplification cycles. In certain embodiments, WGA is performed for fewer than about 10 amplification cycles, e.g., between four and eight cycles, inclusive. However, WGA can be performed for 3, 4, 5, 6, 7, 8, or 9 cycles or for a number of cycles falling within a range defined by any of these values.

RNA Amplification

In certain embodiments, RNA from single cell or a small population of cells can be analyzed for one or more RNA targets. Suitable RNA targets include mRNA, as well as non-coding RNA, such as small nucleolar RNA (snoRNA), microRNA (miRNA), small interfering RNA (siRNA), and Piwi-interacting RNAs (piRNA). In particular embodiments, the RNA of interest is converted to DNA, e.g., by reverse transcription or amplification.

For example, to analyze mRNA of a single cell or a small population of cells, the mRNA is generally converted to a DNA representation of the mRNA population. In certain embodiments, the method(s) employed preferably yield(s) a population of cDNAs, wherein the relative amounts of each cDNA is approximately the same as the relative amounts of the corresponding mRNAs in the sample population.

In particular embodiments, reverse transcription can be employed to produce cDNA from the mRNA template, utilizing reverse transcriptase according to standard techniques. Reverse transcription of a cell's mRNA population can be primed, e.g., with the use of specific primers, oligo-dT, or random primers. To synthesize a cDNA library representative of cellular mRNA, a first strand of cDNA complementary to the sample cellular RNA can be synthesized using reverse transcriptase. This can be done using the commercially available BRL Superscript II kit (BRL, Gaithersburg, Md.) or any other commercially available kit. Reverse transcriptase preferentially utilizes RNA as a template, but can also utilize single-stranded DNA templates. Accordingly, second strand cDNA synthesis can be carried out using reverse transcriptase and suitable primers (e.g., poly-A, random primers, etc.). Second strand synthesis can also be carried out using E. coli DNA polymerase I. The RNA can be removed at the same time the second cDNA strand is synthesized or afterwards. This is done by, for example, treating the mixture to an RNase such as E. coli RNase H, that degrades the RNA.

In other embodiments, an amplification method is employed to produce cDNA from the mRNA template. In such embodiments, an amplification method that produces a population of cDNA that is representative of the mRNA population is typically employed.

The analysis of non-coding RNA from a single cell or a small population of cells also typically begins with the conversion of the RNA of interest to DNA. This conversion can be carried out by reverse transcription or amplification. In certain embodiments, the method(s) employed preferably yield(s) a population of DNAs, wherein the relative amounts of each DNA is approximately the same as the relative amounts of the corresponding mRNAs in the sample population. The target RNAs can be selectively reverse-transcribed or amplified using primers that anneal preferentially to the RNAs of interest. Suitable primers are commercially available or can be designed by those of skill in the art. For example, Life Technologies sells MegaPlex™ Pools of primers for microRNA (miRNA) targets. These primers can be used for both reverse transcription (RT) and specific target amplification (STA). See, e.g., Example 2B.

Preamplification

Preamplification can be carried to increase the concentration of nucleic acid sequences in a reaction mixture, generally, e.g, using a set of random primers, primers that are specific for one or more sequences common to a plurality of, or all, nucleic acids present (e.g., poly-dT to prime poly-A tails), or a combination of a set of random primers and a specific primer. Alternatively, preamplification can be carried out using one or more primer pairs specific for the one or more target nucleic acids of interest. In specific, illustrative embodiments, an amplified genome produced by WGA or the DNA produced from RNA (e.g., cDNA) can preamplified to produce a preamplification reaction mixture that includes one or more amplicons specific for one or more target nucleic acids of interest. Preamplification is typically carried out using preamplification primers, a suitable buffer system, nucleotides, and DNA polymerase enzyme (e.g., a polymerase enzyme modified for "hot start" conditions).

In particular embodiments, the preamplification primers are the same sequence as those to be used in an amplification assay for which the sample is being prepared although generally in reduced concentration. The primer concentration can, e.g, be about 10 to about 250 times less than the primer concentrations used in the amplification assay. Embodiments include the use of primers that are about 10, 20, 35, 50, 65, 75, 100, 125, 150, 175, and 200 times less than that of the primer concentration in the amplification assay.

In specific embodiments, preamplification is carried out for at least two cycles. In certain embodiments, preamplification is carried out for fewer than about 20 cycles, e.g., between 8 and 18 cycles, inclusive. However, preamplification can be performed for 3, 4, 5, 6, 7, 8, 9, 10, 11, 12, 13, 14, 15, 16, 17, 18, 19, 20, 21, 22, 23, or 24 cycles or for a number of cycles falling within a range defined by any of these values. In an exemplary embodiment, preamplification is carried out for about 14 cycles in order to increase the amplicons to be detected by about 16,000 fold.

Amplification for Incorporating Nucleic Acid Sequences into Target Nucleic Acids Amplification to incorporate one or more nucleotide sequences into target nucleic acids can be carried out using two or more primers that contain one or more nucleic acid sequences in addition to portions that anneal to the target nucleic acids. One or more of these portions may contain random sequences to incorporate nucleic acid sequences into essentially all nucleic acids in the sample. Alternatively, or in addition, one or more of these portions may be specific for one or more sequences common to a plurality of, or all, nucleic acids present. In other embodiments, the primers include portions specific for one or more particular target nucleic acids. Nucleic acid sequences can be incorporated using as few as two primers. However, various embodiments employ three, four, five, or six or more primers, as discussed in more detail below.

Three-Primer Methods

In particular embodiments, the invention provides an amplification method for incorporating a plurality (e.g., at least three) of selected nucleotide sequences into one or more target nucleic acid(s). The method entails amplifying a plurality of target nucleic acids, in some embodiments, in a plurality of samples. In illustrative embodiments, the same set of target nucleic acids can be amplified in each of two or more different samples. The samples can differ from one another in any way, e.g., the samples can be from different tissues, subjects, environmental sources, etc. At least three primers can be used to amplify each target nucleic acid, namely: forward and reverse amplification primers, each primer including a target-specific portion and one or both primers including a nucleotide tag. The target-specific portions can specifically anneal to a target under suitable annealing conditions. The nucleotide tag for the forward primer can have a sequence that is the same as, or different from, the nucleotide tag for the reverse primer. Generally, the nucleotide tags are 5' of the target-specific portions. The third primer is a barcode primer comprising a barcode nucleotide sequence and a first and/or second nucleotide tag-specific portion. The barcode nucleotide sequence is a sequence selected to encode information about the amplicon produced when the barcode primer is employed in an amplification reaction. The tag-specific portion can specifically anneal to the one or both nucleotide tags in the forward and reverse primers. The barcode primer is generally 5' of the tag-specific portion.

The barcode primer is typically present in the amplification mixture in excess of the forward and/or reverse or (inner) primer(s). More specifically, if the barcode primer anneals to the nucleotide tag in the forward primer, the barcode primer is generally present in excess of the forward primer. If the barcode primer anneals to the nucleotide tag in the reverse primer, the barcode primer is generally present in excess of the reverse primer. In each instance the third primer in the amplification mixture, i.e., the reverse primer or the forward primer, respectively, can be present, in illustrative embodiments, at a concentration approximately similar to that of the barcode primer. Generally the barcode primer is present in substantial excess. For example, the concentration of the barcode primer in the amplification mixtures can be at least 2-fold, at least 4-fold, at least 5-fold, at least 10-fold, at least 15-fold, at least 20-fold, at least 25-fold, at least 30-fold, at least 35-fold, at least 40-fold, at least 45-fold, at least 50-fold, at least 100-fold, at least 500-fold, at least $10^3$-fold, at least $5\times10^3$-fold, at least $10^4$-fold, at least $5\times10^4$-fold, at least $10^5$-fold, at least $5\times10^5$-fold, at least $10^6$-fold, or higher, relative to the concentration of the forward and/or reverse primer(s). In addition, the concentration excess of the barcode primer can fall within any range having any of the above values as endpoints (e.g., 2-fold to $10^5$-fold). In illustrative embodiments, where the barcode primer has a tag-specific portion that is specific for the nucleotide tag on the forward primer, the forward primer can be present in picomolar to nanomolar concentrations, e.g., about 5 µM to 500 nM, about 5 µM to 100 nM, about 5 µM to 50 nM, about 5 µM to 10 nM, about 5 µM to 5 nM, about 10 µM to 1 nM, about 50 µM to about 500 µM, about 100 µM or any other range having any of these values as endpoints (e.g., 10 µM to 50 µM). Suitable, illustrative concentrations of barcode primer that could be used on combination with any of these concentrations of forward primer include about 10 nM to about 10 µM, about 25 nM to about 7.5 µM, about 50 nM to about 5 µM, about 75 nM to about 2.5 µM, about 100 nM to about 1 µM, about 250 nM to about 750 nM, about 500 nM or any other range having any of these values as endpoints (e.g., 100 nM to 500 nM). In amplification reactions using such concentrations of forward and barcode primers, the reverse primer have a concentration on the same order as the barcode primer (e.g. within about 10-fold, within about 5-fold, or equal).

Each amplification mixture can be subjected to amplification to produce target amplicons comprising tagged target nucleotide sequences, each comprising first and second nucleotide tags flanking the target nucleotide sequence, and at least one barcode nucleotide sequence at the 5' or 3' end of the target amplicon (relative to one strand of the target amplicon). In certain embodiments, the first and second nucleotide tags and/or the barcode nucleotide sequence are selected so as to avoid substantial annealing to the target nucleic acids. In such embodiments, the tagged target nucleotide sequences can include molecules having the following elements: 5'-(barcode nucleotide sequence)-(first nucleotide tag from the forward primer)-(target nucleotide sequence)-(second nucleotide tag sequence from the reverse primer)-3' or 5'-(first nucleotide tag from the forward primer)-(target nucleotide sequence)-(second nucleotide tag sequence from the reverse primer)-(barcode nucleotide sequence)-3'.

Four-Primer Methods

In some embodiments, more than three primers can be employed to add desired elements to a target nucleotide sequence. For example, four primers can be employed to produce molecules having the same elements discussed above, plus an optional additional barcode e.g., 5'-(barcode nucleotide sequence)-(first nucleotide tag from the forward primer)-(target nucleotide sequence)-(second nucleotide tag from the reverse primer)-(additional barcode nucleotide sequence)-3'. In an illustrative four-primer embodiment, the forward primer includes a target-specific portion and first nucleotide tag, and the reverse primer includes a target-specific portion and a second nucleotide tag. Together, these two primers constitute the "inner primers." The remaining two primers are the "outer primers," which anneal to the first and second nucleotide tags present in the inner primers. One outer primer is a barcode primer, as described above. The second outer primer can include a second tag-specific portion and an additional barcode nucleotide sequence, i.e., it can be a second barcode primer.

Amplification to incorporate elements from more than three primers can be carried out in one or multiple amplification reactions. For example, a four-primer amplification can be carried out in one amplification reaction, in which all four primers are present. Alternatively, a four-primer amplification can be carried out, e.g., in two amplification reactions: one to incorporate the inner primers and a separate amplification reaction to incorporate the outer primers. Where all four primers are present in one amplification reaction, the outer primers are generally present in the reaction mixture in excess. The relative concentration values give above for the barcode primer relative to the forward and/or reverse primers also applies to the concentrations of the outer primers relative to inner primers in a one-step, four-primer amplification reaction.

Combinatorial Methods

In an illustrative embodiment of the four-primer amplification reaction, each of the outer primers contains a unique barcode. For example, one barcode primer would be constructed of the elements 5'-(first barcode nucleotide sequence)-(first nucleotide tag)-3', and the second barcode primer would be constructed of the elements 5'-(second barcode nucleotide sequence)-(second nucleotide tag)-3'. In this embodiment, a number (J) of first barcode primers can be combined with a number (K) of second barcode primers to create J×K unique amplification products.

In a further illustrative embodiment of the invention, more than four primers can be combined in a single reaction to append different combinations of barcode nucleotide sequences and nucleotide tags. For example, outer barcode primers containing the following elements: 5'-(first barcode nucleotide sequence)-(first nucleotide tag)-3',5'-(first barcode nucleotide sequence)-(second nucleotide tag)-3',5'-(first barcode nucleotide sequence)-(first nucleotide tag)-3', 5'-(first barcode nucleotide sequence)-(second nucleotide tag)-3', can be combined with inner target-specific primers as described above to produce amplification product pools containing all combinations of the barcode primers with the desired amplicon sequence.

In other illustrative embodiments of the invention, outer barcode primers in any of the combinations described above, or other combinations that would be obvious to one of skill in the art, can be combined with more than one pair of target primer sequences bearing the same first and second nucleotide tag sequences. For example, inner primers containing up to ten different target-specific forward primer sequences combined with the same first nucleotide tag and up to ten different target-specific reverse primer sequences combined with the same second nucleotide tag can be combined with the up to 2 or up to 4 outer barcode primers to generate multiple amplification products as described above. In various embodiments, at least 10, at least 20, at least 50, at least 100, at least 200, at least 500, at least 1000, at least 2000, at least 5000 or at least 10000 different target-specific primer pairs bearing the same first nucleotide tag and second nucleotide tag would be combined with the up to 2 or up to 4 outer barcode primers to generate multiple amplification products.

Bidirectional Combinatorial Methods

In an illustrative embodiment of the four-primer amplification reaction, inner and outer primers can each include a unique barcode, such that amplification produces a barcode combination at each end of the resultant amplicons. This approach is useful when the amplicons are to be sequenced because the barcode combination can be read from either end of the sequence. For example, four primers can be employed to produce molecules having the following elements: 5'-second barcode nucleotide sequence-first nucleotide tag sequence-first barcode nucleotide sequence-target nucleotide sequence-first barcode nucleotide sequence-second nucleotide tag sequence-second barcode nucleotide sequence-3'. In an illustrative four-primer embodiment, two inner primers can include:
 a forward, inner primer including a first nucleotide tag, a first barcode nucleotide sequence, and a target-specific portion; and
 a reverse, inner primer including a target-specific portion, a first barcode nucleotide sequence, and a second nucleotide tag. Two outer primers can include:
 a forward, outer primer including a second barcode nucleotide sequence and a first nucleotide tag-specific portion; and
 a reverse, outer primer including a second nucleotide tag-specific portion and a second barcode nucleotide sequence. As discussed above, if the inner and outer primers are included in the same reaction mixture, the outer primers are preferably present in excess.

A similar combination of elements may be produced in a six-primer amplification method that employs "stuffer" primers, in addition to inner and outer primers. Thus, for example, two inner primers can include:
 a forward, inner primer including a first nucleotide tag and a target-specific portion; and
 a reverse, inner primer including a target-specific portion and a second nucleotide tag. Two stuffer primers can include:
 a forward, stuffer primer including a third nucleotide tag, a first barcode nucleotide sequence, and a first nucleotide tag-specific portion; and
 a reverse, stuffer primer including a second nucleotide tag-specific portion, a first barcode nucleotide sequence, a fourth nucleotide tag. Two outer primers can include:
 a forward, outer primer including a second barcode nucleotide sequence and a third nucleotide tag-specific portion; and
 a reverse, outer primer including a fourth nucleotide tag-specific portion and a second barcode nucleotide sequence. Nucleic acid amplification produces an amplicon including the following elements: 5'-second barcode nucleotide sequence-third nucleotide tag sequence-first barcode nucleotide sequence-first nucleotide tag sequence-target nucleotide sequence-second nucleotide tag sequence-first barcode nucleotide sequence-fourth nucleotide tag sequence-second barcode nucleotide sequence-3'. Amplification can be carried out in one, two, three amplification reactions. For example, all three primer pairs can be included in one reaction. Alternatively, two reactions can be carried out, e.g., a first reaction including the inner and stuffer primers, and a second reaction including only the outer primers; or a first reaction including only the inner primers, followed by a second reaction including the stuffer and outer primers. Where more than one primer pair is present, the primer pair that is the "outer" pair, relative to the other pair is preferably present in excess, as discussed above. Thus, if the inner and stuffer primers are included in a reaction mixture, the stuffer primers are preferably present in excess, and if the stuffer and outer primers are included in a reaction mixture, the outer primers are preferably present in excess. When all three primer pairs are included in a single reaction, the stuffer primers can be present at a concentration intermediate between that of the inner primers and the outer primers.

Reactions to Incorporate Nucleic Acid Sequences

Any method can be employed to incorporate nucleic acids sequences into target nucleic acids. In illustrative embodiments, PCR is employed. When using three or more primers, the amplification is generally carried out for at least three cycles to incorporate the first and second nucleotide tags and the barcode nucleotide sequence. In various embodiments, amplification is carried out for 5, 10, 15, 20, 25, 30, 35, 40, 45, or 50 cycles, or for any number of cycles falling within a range having any of these values as endpoints (e.g. 5-10 cycles). In particular embodiments, amplification is carried out for a sufficient number of cycles to normalize target amplicon copy number across targets and across samples (e.g., 15, 20, 25, 30, 35, 40, 45, or 50 cycles, or for any number of cycles falling within a range having any of these values as endpoints).

Particular embodiments of the above-described method provide substantially uniform amplification, yielding a plurality of target amplicons wherein the majority of amplicons are present at a level relatively close to the average copy number calculated for the plurality of target amplicons.

Thus, in various embodiments, at least 50, at least 55, at least 60, at least 65, at least 70, at least 75, at least 80, at least 85, at least 90, at least 91, at least 92, at least 93, at least 94, at least 95, at least 96, at least 97, at least 98, or at least 99 percent of the target amplicons are present at greater than 50 percent of the average number of copies of target amplicons and less than 2-fold the average number of copies of target amplicons.

Barcoding Applications

In illustrative embodiments, the barcode nucleotide sequence identifies a particular sample. Thus, for example, a set of T target nucleic acids can be amplified in each of S samples, where S and T are integers, typically greater than one. In such embodiments, amplification can be performed separately for each sample, wherein the same set of forward and reverse primers is used for each sample and the set of forward and reverse primers has at least one nucleotide tag that is common to all primers in the set. A different barcode primer can be used for each sample, wherein the bar code primers have different barcode nucleotide sequences, but the same tag-specific portion that can anneal to the common nucleotide tag. This embodiment has the advantage of reducing the number of different primers that would need to be synthesized to encode sample origin in amplicons produced for a plurality of target sequences. Alternatively, different sets of forward and reverse primers can be employed for each sample, wherein each set has a nucleotide tag that is different from the primers in the other set, and different barcode primers are used for each sample, wherein the barcode primers have different barcode nucleotide sequences and different tag-specific portions. In either case, the amplification produces a set of T amplicons from each sample that bear sample-specific barcodes.

In embodiments wherein the same set of forward and reverse primers is used for each sample, the forward and reverse primers for each target can be initially combined separately from the sample, and each barcode primer can be initially combined with its corresponding sample. Aliquots of the initially combined forward and reverse primers can then be added to aliquots of the initially combined sample and barcode primer to produce S×T amplification mixtures. These amplification mixtures can be formed in any article that can be subjected to conditions suitable for amplification. For example, the amplification mixtures can be formed in, or distributed into, separate compartments of a microfluidic device prior to amplification. Suitable microfluidic devices include, in illustrative embodiments, matrix-type microfluidic devices, such as those described below.

In certain embodiments, target amplicons produced in any of the methods described herein can be recovered from the amplification mixtures. For example, a matrix-type microfluidic device that is adapted to permit recovery of the contents of each reaction compartment (see below) can be employed for the amplification to generate the target amplicons. In variations of these embodiments, the target amplicons can be subjected to further amplification and/or analysis. In certain embodiments, the amount of target amplicons produced in the amplification mixtures can be quantified during amplification, e.g., by quantitative real-time PCR, or after.

In embodiments that are useful in single-particle analysis, combinatorial barcoding can be used to encode the identity of a reaction volume, and thus particle, that was the source of an amplification product. In specific embodiments, nucleic acid amplification is carried out using at least two amplification primers, wherein each amplification primer includes a barcode sequence, and the combination of barcode sequences encodes the identity of the reaction volume that was the source of the reaction product (termed "combinatorial barcoding"). These embodiments are conveniently employed when the separate reaction volumes are in separate compartments of a matrix-type microfluidic device, e.g., like those available from Fluidigm Corp. (South San Francisco, Calif.) and described below (see "Microfluidic Devices"). Each separate compartment can contain a combination of barcode nucleotide sequences that identifies the row and column of the compartment in which the encoding reaction was carried out. If the reaction volumes are recovered and subjected to further analysis that includes detection of the barcode combination (e.g., by DNA sequencing), the results can be associated with a particular compartment and, thereby, with a particular particle in the compartment. Such embodiments are particularly useful when separate reaction volumes are combined during or after the recovery process, such that reaction products from a plurality of separate reaction volumes are combined ("pooled"). In a matrix-type microfluidic device, for example, reaction products from all compartments in a row, all compartments in a column, or all compartments in the device could be pooled. If all compartments in a row are pooled, each column within a row preferably has a unique barcode combination. If all compartments in a column are pooled, each row within a column has a unique barcode combination. If all compartments with a device are pooled, every compartment within the device has a unique barcode combination.

Amplification for Detection and/or Quantification of Target Nucleic Acids

Any method of detection and/or quantification of nucleic acids can be used in the methods described herein to detect amplification products. In one embodiment, PCR (polymerase chain reaction) is used to amplify and/or quantify target nucleic acids. In other embodiments, other amplification systems or detection systems are used, including, e.g., systems described in U.S. Pat. No. 7,118,910 (which is incorporated herein by reference in its entirety for its description of amplification/detection systems). In particular embodiments, real-time quantification methods are used. For example, "quantitative real-time PCR" methods can be used to determine the quantity of a target nucleic acid present in a sample by measuring the amount of amplification product formed during the amplification process itself.

Fluorogenic nuclease assays are one specific example of a real-time quantification method that can be used successfully in the methods described herein. This method of monitoring the formation of amplification product involves the continuous measurement of PCR product accumulation using a dual-labeled fluorogenic oligonucleotide probe—an approach frequently referred to in the literature as the "TaqMan® method." See U.S. Pat. No. 5,723,591; Heid et al., 1996, Real-time quantitative PCR Genome Res. 6:986-94, each incorporated herein by reference in their entireties for their descriptions of fluorogenic nuclease assays. It will be appreciated that while "TaqMan® probes" are the most widely used for qPCR, the methods described herein are not limited to use of these probes; any suitable probe can be used.

Other detection/quantification methods that can be employed in the present invention include FRET and template extension reactions, molecular beacon detection, Scorpion detection, Invader detection, and padlock probe detection.

FRET and template extension reactions utilize a primer labeled with one member of a donor/acceptor pair and a nucleotide labeled with the other member of the donor/ acceptor pair. Prior to incorporation of the labeled nucleotide into the primer during a template-dependent extension reaction, the donor and acceptor are spaced far enough apart that energy transfer cannot occur. However, if the labeled nucleotide is incorporated into the primer and the spacing is sufficiently close, then energy transfer occurs and can be detected. These methods are particularly useful in conducting single base pair extension reactions in the detection of single nucleotide polymorphisms and are described in U.S. Pat. No. 5,945,283 and PCT Publication WO 97/22719.

With molecular beacons, a change in conformation of the probe as it hybridizes to a complementary region of the amplified product results in the formation of a detectable signal. The probe itself includes two sections: one section at the 5' end and the other section at the 3' end. These sections flank the section of the probe that anneals to the probe binding site and are complementary to one another. One end section is typically attached to a reporter dye and the other end section is usually attached to a quencher dye. In solution, the two end sections can hybridize with each other to form a hairpin loop. In this conformation, the reporter and quencher dye are in sufficiently close proximity that fluorescence from the reporter dye is effectively quenched by the quencher dye. Hybridized probe, in contrast, results in a linearized conformation in which the extent of quenching is decreased. Thus, by monitoring emission changes for the two dyes, it is possible to indirectly monitor the formation of amplification product. Probes of this type and methods of their use are described further, for example, by Piatek et al., 1998, Nat. Biotechnol. 16:359-63; Tyagi, and Kramer, 1996, Nat. Biotechnology 14:303-308; and Tyagi, et al., 1998, Nat. Biotechnol. 16:49-53 (1998).

The Scorpion detection method is described, for example, by Thelwell et al. 2000, Nucleic Acids Research, 28:3752-3761 and Solinas et al., 2001, "Duplex Scorpion primers in SNP analysis and FRET applications" Nucleic Acids Research 29:20. Scorpion primers are fluorogenic PCR primers with a probe element attached at the 5'-end via a PCR stopper. They are used in real-time amplicon-specific detection of PCR products in homogeneous solution. Two different formats are possible, the "stem-loop" format and the "duplex" format. In both cases the probing mechanism is intramolecular. The basic elements of Scorpions in all formats are: (i) a PCR primer; (ii) a PCR stopper to prevent PCR read-through of the probe element; (iii) a specific probe sequence; and (iv) a fluorescence detection system containing at least one fluorophore and quencher. After PCR extension of the Scorpion primer, the resultant amplicon contains a sequence that is complementary to the probe, which is rendered single-stranded during the denaturation stage of each PCR cycle. On cooling, the probe is free to bind to this complementary sequence, producing an increase in fluorescence, as the quencher is no longer in the vicinity of the fluorophore. The PCR stopper prevents undesirable read-through of the probe by Taq DNA polymerase.

Invader assays (Third Wave Technologies, Madison, Wis.) are used particularly for SNP genotyping and utilize an oligonucleotide, designated the signal probe, that is complementary to the target nucleic acid (DNA or RNA) or polymorphism site. A second oligonucleotide, designated the Invader Oligo, contains the same 5' nucleotide sequence, but the 3' nucleotide sequence contains a nucleotide polymorphism. The Invader Oligo interferes with the binding of the signal probe to the target nucleic acid such that the 5' end of the signal probe forms a "flap" at the nucleotide containing the polymorphism. This complex is recognized by a structure specific endonuclease, called the Cleavase enzyme. Cleavase cleaves the 5' flap of the nucleotides. The released flap binds with a third probe bearing FRET labels, thereby forming another duplex structure recognized by the Cleavase enzyme. This time, the Cleavase enzyme cleaves a fluorophore away from a quencher and produces a fluorescent signal. For SNP genotyping, the signal probe will be designed to hybridize with either the reference (wild type) allele or the variant (mutant) allele. Unlike PCR, there is a linear amplification of signal with no amplification of the nucleic acid. Further details sufficient to guide one of ordinary skill in the art are provided by, for example, Neri, B. P., et al., *Advances in Nucleic Acid and Protein Analysis* 3826:117-125, 2000) and U.S. Pat. No. 6,706,471.

Padlock probes (PLPs) are long (e.g., about 100 bases) linear oligonucleotides. The sequences at the 3' and 5' ends of the probe are complementary to adjacent sequences in the target nucleic acid. In the central, noncomplementary region of the PLP there is a "tag" sequence that can be used to identify the specific PLP. The tag sequence is flanked by universal priming sites, which allow PCR amplification of the tag. Upon hybridization to the target, the two ends of the PLP oligonucleotide are brought into close proximity and can be joined by enzymatic ligation. The resulting product is a circular probe molecule catenated to the target DNA strand. Any unligated probes (i.e., probes that did not hybridize to a target) are removed by the action of an exonuclease. Hybridization and ligation of a PLP requires that both end segments recognize the target sequence. In this manner, PLPs provide extremely specific target recognition.

The tag regions of circularized PLPs can then be amplified and resulting amplicons detected. For example, TaqMan® real-time PCR can be carried out to detect and quantify the amplicon. The presence and amount of amplicon can be correlated with the presence and quantity of target sequence in the sample. For descriptions of PLPs see, e.g., Landegren et al., 2003, Padlock and proximity probes for in situ and array-based analyses: tools for the post-genomic era, *Comparative and Functional Genomics* 4:525-30; Nilsson et al., 2006, Analyzing genes using closing and replicating circles *Trends Biotechnol.* 24:83-8; Nilsson et al., 1994, Padlock probes: circularizing oligonucleotides for localized DNA detection, *Science* 265:2085-8.

In particular embodiments, fluorophores that can be used as detectable labels for probes include, but are not limited to, rhodamine, cyanine 3 (Cy 3), cyanine 5 (Cy 5), fluorescein, Vic™, Liz™., Tamra™, 5-Fam™, 6-Fam™, and Texas Red (Molecular Probes). (Vic™, Liz™, Tamra™, 5-Fam™, 6-Fam™ are all available from Life Technologies, Foster City, Calif.).

In some embodiments, one can simply monitor the amount of amplification product after a predetermined number of cycles sufficient to indicate the presence of the target nucleic acid sequence in the sample. One skilled in the art can easily determine, for any given sample type, primer sequence, and reaction condition, how many cycles are sufficient to determine the presence of a given target nucleic acid. In other embodiments, detection is carried out at the end of exponential amplification, i.e., during the "plateau" phase, or endpoint PCR is carried out. In various embodiments, amplification can be carried out for about: 2, 4, 10, 15, 20, 25, 30, 35, or 40 cycles or for a number of cycles falling within any range bounded by any of these values.

By acquiring fluorescence over different temperatures, it is possible to follow the extent of hybridization. Moreover, the temperature-dependence of PCR product hybridization can be used for the identification and/or quantification of PCR products. Accordingly, the methods described herein encompass the use of melting curve analysis in detecting and/or quantifying amplicons. Melting curve analysis is well known and is described, for example, in U.S. Pat. Nos. 6,174,670; 6,472,156; and 6,569,627, each of which is hereby incorporated by reference in its entirety, and specifically for its description of the use of melting curve analysis to detect and/or quantify amplification products. In illustrative embodiments, melting curve analysis is carried out using a double-stranded DNA dye, such as SYBR Green, Pico Green (Molecular Probes, Inc., Eugene, Oreg.), EVA Green (Biotinum), ethidium bromide, and the like (see Zhu et al., 1994, Anal. Chem. 66:1941-48).

In certain embodiments, multiplex detection is carried out in individual amplification mixture, e.g., in individual reaction compartments of a microfluidic device, which can be used to further increase the number of samples and/or targets that can be analyzed in a single assay or to carry out comparative methods, such as comparative genomic hybridization (CGH). In various embodiments, up to 2, 3, 4, 5, 6, 7, 8, 9, 10, 50, 100, 500, 1000, 5000, 10000 or more amplification reactions are carried out in each individual reaction compartment.

According to certain embodiments, one can employ an internal standard to quantify the amplification product indicated by the fluorescent signal. See, e.g., U.S. Pat. No. 5,736,333.

Devices have been developed that can perform a thermal cycling reaction with compositions containing a fluorescent dye, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670.

In some embodiments, each of these functions can be performed by separate devices. For example, if one employs a Q-beta replicase reaction for amplification, the reaction may not take place in a thermal cycler, but could include a light beam emitted at a specific wavelength, detection of the fluorescent signal, and calculation and display of the amount of amplification product.

In particular embodiments, combined thermal cycling and fluorescence detecting devices can be used for precise quantification of target nucleic acids. In some embodiments, fluorescent signals can be detected and displayed during and/or after one or more thermal cycles, thus permitting monitoring of amplification products as the reactions occur in real-time. In certain embodiments, one can use the amount of amplification product and number of amplification cycles to calculate how much of the target nucleic acid sequence was in the sample prior to amplification.

Amplification for DNA Sequencing

In certain embodiments, amplification methods are employed to produce amplicons suitable for automated DNA sequencing. Many current DNA sequencing techniques rely on "sequencing by synthesis." These techniques entail library creation, massively parallel PCR amplification of library molecules, and sequencing. Library creation starts with conversion of sample nucleic acids to appropriately sized fragments, ligation of adaptor sequences onto the ends of the fragments, and selection for molecules properly appended with adaptors. The presence of the adaptor sequences on the ends of the library molecules enables amplification of random-sequence inserts. The above-described methods for tagging nucleotide sequences can be substituted for ligation, to incorporate adaptor sequences, as described in greater detail below.

In addition, the ability of the above-described methods to provide substantially uniform amplification of target nucleotide sequences is helpful in preparing DNA sequencing libraries having good coverage. In the context of automated DNA sequencing, the term "coverage" refers to the number of times the sequence is measured upon sequencing. A DNA sequencing library that has substantially uniform coverage can yield sequence data where the coverage is also substantially uniform. Thus, in various embodiments, upon performing automated sequencing of a plurality of target amplicons prepared as described herein, the sequences of at least 50 percent of the target amplicons are present at greater than 50 percent of the average number of copies of target amplicon sequences and less than 2-fold the average number of copies of target amplicon sequences. In various embodiments of this method at least 55, at least 60, at least 65, at least 70, at least 75, at least 80, at least 85, at least 90, at least 91, at least 92, at least 93, at least 94, at least 95, at least 96, at least 97, at least 98, or at least 99 percent of the target amplicon sequences are present at greater than 50 percent of the average number of copies of target amplicon sequences and less than 2-fold the average number of copies of target amplicon sequences.

In certain embodiments, at least three primers can be employed to produce amplicons suitable for DNA sequencing: forward, reverse, and barcode primers. However, one or more of the forward primer, reverse primer, and barcode primer can includes at least one additional primer binding site. In specific embodiments, the barcode primer includes at least a first additional primer binding site upstream of the barcode nucleotide sequence, which is upstream of the first nucleotide tag-specific portion. In certain embodiments, two of the forward primer, reverse primer, and barcode primer include at least one additional primer binding site (i.e, such that the amplicon produced upon amplification includes the nucleotide tag sequences, the barcode nucleotide sequence, and the two additional binding sites). For example, if the barcode primer includes a first additional primer binding site upstream of the barcode nucleotide sequence, in specific embodiments, the reverse primer can include at least a second additional primer binding site downstream of the second nucleotide tag. Amplification then yields a molecule having the following elements: 5'-first additional primer binding site-barcode nucleotide sequence-first nucleotide tag from the forward primer-target nucleotide sequence-second nucleotide tag from the reverse primer-second additional primer binding site-3'. In specific embodiments, the first and second additional primer binding sites are capable of being bound by DNA sequencing primers, to facilitate sequencing of the entire amplicon, including the barcode, which, as discussed above, can indicate sample origin.

In other embodiments, at least four primers are employed to produce amplicons suitable for DNA. For example, inner primers can be used with outer primers that additionally include first and second primer binding sites that are capable of being bound by DNA sequencing primers. Amplification yields a molecule having the following elements: 5'-first primer binding site-second barcode nucleotide sequence-first nucleotide tag sequence-first barcode nucleotide sequence-target nucleotide sequence-first barcode nucleotide sequence-second nucleotide tag sequence-second barcode nucleotide sequence-second primer binding site-3'. Because this molecule contains the barcode combination at either end, sequence can be obtained from either end of the molecule to identify the barcode combination.

In a similar manner, six primers can be employed to prepare DNA for sequencing. More specifically, inner and stuffer primers, as discussed above, can be used with outer primers that additionally include first and second primer binding sites that are capable of being bound by DNA sequencing primers. Amplification yields a molecule having the following elements: 5'-first primer binding site-second barcode nucleotide sequence-third nucleotide tag sequence-first barcode nucleotide sequence-first nucleotide tag sequence-target nucleotide sequence-second nucleotide tag sequence-first barcode nucleotide sequence-fourth nucleotide tag sequence-second barcode nucleotide sequence-second primer binding site-3'. Because this molecule contains the barcode combination at either end, sequence can be obtained from either end of the molecule to identify the barcode combination.

The methods described herein can include subjecting at least one target amplicon to DNA sequencing using any available DNA sequencing method. In particular embodiments, a plurality of target amplicons is sequenced using a high throughput sequencing method. Such methods typically use an in vitro cloning step to amplify individual DNA molecules. Emulsion PCR (emPCR) isolates individual DNA molecules along with primer-coated beads in aqueous droplets within an oil phase. PCR produces copies of the DNA molecule, which bind to primers on the bead, followed by immobilization for later sequencing. emPCR is used in the methods by Marguilis et al. (commercialized by 454 Life Sciences, Branford, Conn.), Shendure and Porreca et al. (also known as "polony sequencing") and SOLiD sequencing, (Life Technologies, Foster City, Calif.). See M. Margulies, et al. (2005) "Genome sequencing in microfabricated high-density picoliter reactors" Nature 437: 376-380; J. Shendure, et al. (2005) "Accurate Multiplex Polony Sequencing of an Evolved Bacterial Genome" Science 309 (5741): 1728-1732. In vitro clonal amplification can also be carried out by "bridge PCR," where fragments are amplified upon primers attached to a solid surface. Braslavsky et al. developed a single-molecule method (commercialized by Helicos Biosciences Corp., Cambridge, Mass.) that omits this amplification step, directly fixing DNA molecules to a surface. I. Braslavsky, et al. (2003) "Sequence information can be obtained from single DNA molecules" Proceedings of the National Academy of Sciences of the United States of America 100: 3960-3964.

DNA molecules that are physically bound to a surface can be sequenced in parallel. "Sequencing by synthesis," like dye-termination electrophoretic sequencing, uses a DNA polymerase to determine the base sequence. Reversible terminator methods (commercialized by Illumina, Inc., San Diego, Calif. and Helicos Biosciences Corp., Cambridge, Mass.) use reversible versions of dye-terminators, adding one nucleotide at a time, and detect fluorescence at each position in real time, by repeated removal of the blocking group to allow polymerization of another nucleotide. "Pyrosequencing" also uses DNA polymerization, adding one nucleotide at a time and detecting and quantifying the number of nucleotides added to a given location through the light emitted by the release of attached pyrophosphates (commercialized by 454 Life Sciences, Branford, Conn.). See M. Ronaghi, et al. (1996). "Real-time DNA sequencing using detection of pyrophosphate release" Analytical Biochemistry 242: 84-89.

Labeling Strategies

Any suitable labeling strategy can be employed in the methods described herein. Where the assay mixture is aliquoted, and each aliquot is analyzed for presence of a single amplification product, a universal detection probe can be employed in the amplification mixture. In particular embodiments, real-time PCR detection can be carried out using a universal qPCR probe. Suitable universal qPCR probes include double-stranded DNA dyes, such as SYBR Green, Pico Green (Molecular Probes, Inc., Eugene, Oreg.), EVA Green (Biotinum), ethidium bromide, and the like (see Zhu et al., 1994, Anal. Chem. 66:1941-48). Suitable universal qPCR probes also include sequence-specific probes that bind to a nucleotide sequence present in all amplification products. Binding sites for such probes can be conveniently incorporated into the tagged target nucleic acids during amplification.

Alternatively, one or more target-specific qPCR probes (i.e., specific for a target nucleotide sequence to be detected) is employed in the amplification mixtures to detect amplification products. Target-specific probes could be useful, e.g., when only a few target nucleic acids are to be detected in a large number of samples. For example, if only three targets were to be detected, a target-specific probe with a different fluorescent label for each target could be employed. By judicious choice of labels, analyses can be conducted in which the different labels are excited and/or detected at different wavelengths in a single reaction. See, e.g., Fluorescence Spectroscopy (Pesce et al., Eds.) Marcel Dekker, New York, (1971); White et al., Fluorescence Analysis: A Practical Approach, Marcel Dekker, New York, (1970); Berlman, Handbook of Fluorescence Spectra of Aromatic Molecules, 2nd ed., Academic Press, New York, (1971); Griffiths, Colour and Constitution of Organic Molecules, Academic Press, New York, (1976); Indicators (Bishop, Ed.). Pergamon Press, Oxford, 19723; and Haugland, Handbook of Fluorescent Probes and Research Chemicals, Molecular Probes, Eugene (1992).

Removal of Undesired Reaction Components

It will be appreciated that reactions involving complex mixtures of nucleic acids in which a number of reactive steps are employed can result in a variety of unincorporated reaction components, and that removal of such unincorporated reaction components, or reduction of their concentration, by any of a variety of clean-up procedures can improve the efficiency and specificity of subsequently occurring reactions. For example, it may be desirable, in some embodiments, to remove, or reduce the concentration of preamplification primers prior to carrying out the amplification steps described herein.

In certain embodiments, the concentration of undesired components can be reduced by simple dilution. For example, preamplified samples can be diluted about 2-, 5-, 10-, 50-, 100-, 500-, 1000-fold prior to amplification to improve the specificity of the subsequent amplification step.

In some embodiments, undesired components can be removed by a variety of enzymatic means. Alternatively, or in addition to the above-described methods, undesired components can be removed by purification. For example, a purification tag can be incorporated into any of the above-described primers (e.g., into the barcode nucleotide sequence) to facilitate purification of the tagged target nucleotides.

In particular embodiments, clean-up includes selective immobilization of the desired nucleic acids. For example, desired nucleic acids can be preferentially immobilized on a solid support. In an illustrative embodiment, an affinity moiety, such as biotin (e.g., photo-biotin), is attached to desired nucleic acid, and the resulting biotin-labeled nucleic acids immobilized on a solid support comprising an affinity moiety-binder such as streptavidin. Immobilized nucleic acids can be queried with probes, and non-hybridized and/or non-ligated probes removed by washing (See, e.g., Published P.C.T. Application WO 03/006677 and U.S. Ser. No. 09/931,285.) Alternatively, immobilized nucleic acids can be washed to remove other components and then released from the solid support for further analysis. This approach can be used, for example, in recovering target amplicons from amplification mixtures after the addition of primer binding sites for DNA sequencing. In particular embodiments, an affinity moiety, such as biotin, can be attached to an amplification primer such that amplification produces an affinity moiety-labeled (e.g., biotin-labeled) amplicon. Thus, for example, where three primers are employed to add barcode and nucleotide tag elements to a target nucleotide sequence, as described above, at least one of the barcode or reverse primers can include an affinity moiety. Where four primers (two inner primers and two outer primers) are employed to add desired element to a target nucleotide sequence, at least one of the outer primers can include an affinity moiety.

Microfluidic Devices

In certain embodiments, methods described herein can be carried out using a microfluidic device. In illustrative embodiments, the device is a matrix-type microfluidic device that allows the simultaneous combination of a plurality of substrate solutions with reagent solutions in separate isolated reaction compartments. It will be recognized, that a substrate solution can include one or a plurality of substrates (e.g., target nucleic acids) and a reagent solution can include one or a plurality of reagents. For example, the microfluidic device can allow the simultaneous pair-wise combination of a plurality of different amplification primers and samples. In certain embodiments, the device is configured to contain a different combination of primers and samples in each of the different compartments. In various embodiments, the number of separate reaction compartments can be greater than 50, usually greater than 100, more often greater than 500, even more often greater than 1000, and sometimes greater than 5000, or greater than 10,000.

In particular embodiments, the matrix-type microfluidic device is a Dynamic Array ("DA") microfluidic device. A DA microfluidic device is a matrix-type microfluidic device designed to isolate pair-wise combinations of samples and reagents (e.g., amplification primers, detection probes, etc.) and suited for carrying out qualitative and quantitative PCR reactions including real-time quantitative PCR analysis. In some embodiments, the DA microfluidic device is fabricated, at least in part, from an elastomer. DA microfluidic devices are described in PCT Publication No. WO05107938A2 (Thermal Reaction Device and Method For Using The Same) and U.S. Patent Publication No. US20050252773A1, both incorporated herein by reference in their entireties for their descriptions of DA microfluidic devices. DA microfluidic devices may incorporate high-density matrix designs that utilize fluid communication vias between layers of the microfluidic device to weave control lines and fluid lines through the device and between layers. By virtue of fluid lines in multiple layers of an elastomeric block, high density reaction cell arrangements are possible. Alternatively DA microfluidic devices may be designed so that all of the reagent and sample channels are in the same elastomeric layer, with control channels in a different layer. In certain embodiments, DA microfluidic devices may be used for reacting M number of different samples with N number of different reagents.

Although the DA microfluidic devices described in WO05107938 are well suited for conducting the methods described herein, the invention is not limited to any particular device or design. Any device that partitions a sample and/or allows independent pair-wise combinations of reagents and sample may be used. U.S. Patent Publication No. 20080108063 (which is hereby incorporated by reference it its entirety) includes a diagram illustrating the 48.48 Dynamic Array IFC (Integrated Fluidic Circuit), a commercially available device available from Fluidigm Corp. (South San Francisco Calif.). It will be understood that other configurations are possible and contemplated such as, for example, 48×96; 96×96; 30×120; etc.

In specific embodiments, the microfluidic device can be a Digital Array microfluidic device, which is adapted to perform digital amplification. Such devices can have integrated channels and valves that partition mixtures of sample and reagents into nanoliter volume reaction compartments. In some embodiments, the Digital Array microfluidic device is fabricated, at least in part, from an elastomer. Illustrative Digital Array microfluidic devices are described in copending U.S. Applications owned by Fluidigm Corp. (South San Francisco, Calif.), such as U.S. application Ser. No. 12/170, 414, entitled "Method and Apparatus for Determining Copy Number Variation Using Digital PCR." One illustrative embodiment has 12 input ports corresponding to 12 separate sample inputs to the device. The device can have 12 panels, and each of the 12 panels can contain 765 6 nL reaction compartments with a total volume of 4.59 µL per panel. Microfluidic channels can connect the various reaction compartments on the panels to fluid sources. Pressure can be applied to an accumulator in order to open and close valves connecting the reaction compartments to fluid sources. In illustrative embodiments, 12 inlets can be provided for loading of the sample reagent mixture. 48 inlets can be used to provide a source for reagents, which are supplied to the chip when pressure is applied to accumulator. Additionally, two or more inlets can be provided to provide hydration to the chip.

While the Digital Array microfluidic devices are well suited for carrying out certain amplification methods described herein, one of ordinary skill in the art would recognize many variations and alternatives to these devices. The geometry of a given Digital Array microfluidic device will depend on the particular application. Additional description related to devices suitable for use in the methods described herein is provided in U.S. Patent Publication No. 20050252773, incorporated herein by reference for its disclosure of Digital Array microfluidic devices.

In certain embodiments, the methods described herein can be performed using a microfluidic device that provides for recovery of reaction products. Such devices are described in detail in copending U.S. Application No. 61/166,105, filed Apr. 2, 2009, (which is hereby incorporated by reference in its entirety and specifically for its description of microfluidic devices that permit reaction product recovery and related methods) and sold by Fluidigm Corp. as Access Array™ IFC (Integrated Fluidic Circuit).

In an illustrative device of this type, independent sample inputs are combined with primer inputs in an M×N array configuration. Thus, each reaction is a unique combination of a particular sample and a particular reagent mixture. Samples are loaded into sample compartments in the microfluidic device through sample input lines arranged as columns in one implementation. Assay reagents (e.g., primers) are loaded into assay compartments in the microfluidic device through assay input lines arranged as rows crossing the columns. The sample compartments and the assay compartments are in fluidic isolation during loading. After the loading process is completed, an interface valve operable to obstruct a fluid line passing between pairs of sample and assay compartments is opened to enable free interface diffusion of the pairwise combinations of samples and assays. Precise mixture of the samples and assays enables reactions to occur between the various pairwise combinations, producing one or more reaction product(s) in each compartment. The reaction products are harvested and can then be used for subsequent processes. The terms "assay" and "sample" as used herein are descriptive of particular uses of the devices in some embodiments. However, the uses of the devices are not limited to the use of "sample(s)" and "assay(s)" in all embodiments. For example, in other embodiments, "sample(s)" may refer to "a first reagent" or a plurality of "first reagents" and "assay(s)" may refer to "a second reagent" or a plurality of "second reagents." The M×N character of the devices enable the combination of any set of first reagents to be combined with any set of second reagents.

According to particular embodiments, the reaction products from the M×N pairwise combinations can be recovered from the microfluidic device in discrete pools, e.g., one for each of M samples. Typically, the discrete pools are contained in a sample input port provided on the carrier. In some processes, the reaction products may be harvested on a "per amplicon" basis for purposes of normalization. Utilizing embodiments of the present invention, it is possible to achieve results (for replicate experiments assembled from the same input solutions of samples and assays) for which the copy number of amplification products varies by no more than ±25% within a sample and no more than ±25% between samples. Thus, the amplification products recovered from the microfluidic device will be representative of the input samples as measured by the distribution of specific known genotypes. In certain embodiments, output sample concentration will be greater than 2,000 copies/amplicon/microliter, and recovery of reaction products will be performed in less than two hours.

In some embodiments, reaction products are recovered by dilation pumping. Dilation pumping provides benefits not typically available using conventional techniques. For example, dilation pumping enables for a slow removal of the reaction products from the microfluidic device. In an exemplary embodiment, the reaction products are recovered at a fluid flow rate of less than 100 µl per hour. In this example, for 48 reaction products distributed among the reaction compartments in each column, with a volume of each reaction product of about 1.5 µl, removal of the reaction products in a period of about 30 minutes, will result in a fluid flow rate of 72 µl/hour. (i.e., 48×1.5/0.5 hour). In other embodiments, the removal rate of the reaction products is performed at a rate of less than 90 µl/hr, 80 µl/hr, 70 µl/hr, 60 µl/hr, 50 µl/hr, 40 µl/hr, 30 µl/hr, 20 µl/hr, 10 µl/hr, 9 µl/hr, less than 8 µl/hr, less than 7 µl/hr, less than 6 µl/hr, less than 5 µl/hr, less than 4 µl/hr, less than 3 µl/hr, less than 2 µl/hr, less than 1 µl/hr, or less than 0.5 µl/hr.

Dilation pumping results in clearing of substantially a high percentage and potentially all the reaction products present in the microfluidic device. Some embodiments remove more than 75% of the reaction products present in the reaction compartments (e.g., sample compartments) of the microfluidic device. As an example, some embodiments remove more than 80%, 85%, 90%, 92%, 95%, 96%, 97%, 98%, or 99% of the reaction products present in the reaction compartments.

The methods described herein may use microfluidic devices with a plurality of "unit cells" that generally include a sample compartment and an assay compartment. Such unit cells can have dimensions on the order of several hundred microns, for example unit cells with dimension of 500×500 µm, 525×525 µm, 550×550 µm, 575×575 µm, 600×600 µm, 625×625 µm, 650×650 µm, 675×675 µm, 700×700 µm, or the like. The dimensions of the sample compartments and the assay compartments are selected to provide amounts of materials sufficient for desired processes while reducing sample and assay usage. As examples, sample compartments can have dimensions on the order of 100-400 µm in width× 200-600 µm in length×100-500 µm in height. For example, the width can be 100 µm, 125 µm, 150 µm, 175 µm, 200 µm, 225 µm, 250 µm, 275 µm, 300 µm, 325 µm, 350 µm, 375 µm, 400 µm, or the like. For example, the length can be 200 µm, 225 µm, 250 µm, 275 µm, 300 µm, 325 µm, 350 µm, 375 µm, 400 µm, 425 µm, 450 µm, 475 µm, 500 µm, 525 µm, 550 µm, 575 µm, 600 µm, or the like. For example, the height can be 100 µm, 125 µm, 150 µm, 175 µm, 200 µm, 225 µm, 250 µm, 275 µm, 300 µm, 325 µm, 350 µm, 375 µm, 400 µm, 425 µm, 450 µm, 475 µm, 500 µm, 525 µm, 550 µm, 575 µm, 600 µm, or the like. Assay compartments can have similar dimensional ranges, typically providing similar steps sizes over smaller ranges than the smaller compartment volumes. In some embodiments, the ratio of the sample compartment volume to the assay compartment volume is about 5:1, 10:1, 15:1, 20:1, 25:1, or 30:1. Smaller compartment volumes than the listed ranges are included within the scope of the invention and are readily fabricated using microfluidic device fabrication techniques.

Higher density microfluidic devices will typically utilize smaller compartment volumes in order to reduce the footprint of the unit cells. In applications for which very small sample sizes are available, reduced compartment volumes will facilitate testing of such small samples.

For single-particle analysis, microfluidic devices can be designed to facilitate loading and capture of the particular particles to be analyzed. FIG. 1 shows the unit cell architecture for an illustrative microfluidic device for analyzing mammalian cells. Each unit cell has a "cell channel" (i.e., sample compartment) and an "assay channel" (i.e., assay compartment). The cell channel is rounded for loading mammalian cells, with dimensions on the order of tens microns in diameter to a hundred of several hundred microns in length. Diameters can be about 15 µm, about 20 µm, about 25 µm, about 30 µm, about 35 µm, about 40 µm, or about 45 µm or more, or can fall within a range having any of these values as endpoints, depending on the size of the cells being analyzed. Lengths can be about 60 µm, about 90 µm, about 120 µm, about 150 µm, about 170 µm, about 200 µm, about 230 µm, about 260 µm, about 290 µm or more, or can fall within a range having any of these values as endpoints, depending on the size of the cells being analyzed. In an illustrative microfluidic device based on the Access Array™ IFC platform (the "MA006"), a unit cell for loading mammalian cells can be about 30 µm×170 µm. Such a device can be equipped to provide, or to facilitate providing, heat to cell channels after loading to lyse the cells. As shown in FIG. 1, the device can include assay channels separate from cell channels for conducting reactions such as nucleic acid amplification. 170 µm×170 containment valves can be used to close cell channels.

Co-pending U.S. App. No. 61/605,016, filed Feb. 29, 2012, and entitled "Methods, Systems, And Devices For Multiple Single-Particle or Single-Cell Processing Using Microfluidics," describes methods, systems, and devices for multiple single-particle or single-cell processing utilizing microfluidics. Various embodiments provide for capturing, partitioning, and/or manipulating individual particles or cells from a larger population of particles of cells along with generating genetic information and/or reaction(s) related to each individual particle or cell. Some embodiments may be configured for imaging the individual particles or cells or associated reaction products as part of the processing. This application is incorporated by reference herein it its entirety and, in particular, for its description of microfluidic devices configured for multiple single-particle or single-cell processing and related systems.

In specific embodiments, a microfluidic device is employed that facilitates assays having a dynamic range of at least 3 orders of magnitude, more often at least 4, at least 5, at least 6, at least 7, or at least 8 orders of magnitude.

Fabrication methods using elastomeric materials and methods for design of devices and their components have been described in detail in the scientific and patent literature. See, e.g., Unger et al. (2000) Science 288:113-116; U.S. Pat. No. 6,960,437 (Nucleic acid amplification utilizing microfluidic devices); U.S. Pat. No. 6,899,137 (Microfabricated elastomeric valve and pump systems); U.S. Pat. No. 6,767,706 (Integrated active flux microfluidic devices and methods); U.S. Pat. No. 6,752,922 (Microfluidic chromatography); U.S. Pat. No. 6,408,878 (Microfabricated elastomeric valve and pump systems); U.S. Pat. No. 6,645,432 (Microfluidic devices including three-dimensionally arrayed channel networks); U.S. Patent Application Publication Nos. 2004/0115838; 2005/0072946; 2005/0000900; 2002/0127736; 2002/0109114; 2004/0115838; 2003/0138829; 2002/0164816; 2002/0127736; and 2002/0109114; PCT Publication Nos. WO 2005/084191; WO 05/030822A2; and WO 01/01025; Quake & Scherer, 2000, "From micro to nanofabrication with soft materials" Science 290: 1536-40; Unger et al., 2000, "Monolithic microfabricated valves and pumps by multilayer soft lithography" Science 288:113-116; Thorsen et al., 2002, "Microfluidic large-scale integration" Science 298:580-584; Chou et al., 2000, "Microfabricated Rotary Pump" Biomedical Microdevices 3:323-330; Liu et al., 2003, "Solving the "world-to-chip" interface problem with a microfluidic matrix" Analytical Chemistry 75, 4718-23, Hong et al, 2004, "A nanoliter-scale nucleic acid processor with parallel architecture" Nature Biotechnology 22:435-39.

Data Output and Analysis

In certain embodiments, when the methods described herein are carried out on a matrix-type microfluidic device, the data can be output as a heat matrix (also termed "heat map"). In the heat matrix, each square, representing a reaction compartment on the DA matrix, has been assigned a color value which can be shown in gray scale, but is more typically shown in color. In gray scale, black squares indicate that no amplification product was detected, whereas white squares indicate the highest level of amplification produce, with shades of gray indicating levels of amplification product in between. In a further aspect, a software program may be used to compile the data generated in the heat matrix into a more reader-friendly format.

Applications

In particular embodiments, the methods described herein are used in the analysis of one or more nucleic acids, e.g., in or associated with a particle. Thus, for example, these methods are applicable to identifying the presence of particular polymorphisms (such as SNPs), alleles, or haplotypes, or chromosomal abnormalities, such as amplifications, deletions, rearrangements, or aneuploidy. The methods may be employed in genotyping, which can be carried out in a number of contexts, including diagnosis of genetic diseases or disorders, cancer, pharmacogenomics (personalized medicine), quality control in agriculture (e.g., for seeds or livestock), the study and management of populations of plants or animals (e.g., in aquaculture or fisheries management or in the determination of population diversity), or paternity or forensic identifications. The methods described herein can be applied in the identification of sequences indicative of particular conditions or organisms in biological or environmental samples. For example, the methods can be used in assays to identify pathogens, such as viruses, bacteria, and fungi. The methods can also be used in studies aimed at characterizing environments or microenvironments, e.g., characterizing the microbial species in the human gut.

In certain embodiments, these methods can also be employed in determinations of DNA or RNA copy number. Determinations of aberrant DNA copy number in genomic DNA is useful, for example, in the diagnosis and/or prognosis of genetic defects and diseases, such as cancer. Determination of RNA "copy number," i.e., expression level is useful for expression monitoring of genes of interest, e.g., in different individuals, tissues, or cells under different conditions (e.g., different external stimuli or disease states) and/or at different developmental stages.

In addition, the methods can be employed to prepare nucleic acid samples for further analysis, such as, e.g., DNA sequencing.

Furthermore, nucleic acid samples can be tagged as a first step, prior subsequent analysis, to reduce the risk that mislabeling or cross-contamination of samples will compromise the results. For example, any physician's office, laboratory, or hospital could tag samples immediately after collection, and the tags could be confirmed at the time of analysis. Similarly, samples containing nucleic acids collected at a crime scene could be tagged as soon as practicable, to ensure that the samples could not be mislabeled or tampered with. Detection of the tag upon each transfer of the sample from one party to another could be used to establish chain of custody of the sample.

As discussed above, the methods described herein can be used in the analysis of other parameters of particles besides nucleic acids, such as, for example, the expression level(s) of one or more proteins in or associated with each particle. In some embodiments, one or more nucleic acids are analyzed, together with one or more other parameters, for each particle.

The ability to associate assay results for multiple parameters with each particle in a population of particles can be exploited in a variety of different types of investigations. In various embodiments, the methods described herein can be employed to identify two or more copy number variations, two or more mutations, or at least one copy number variation and at least one mutation that are, together, correlated with a phenotype. The phenotype can, for example, be risk, presence, severity, prognosis, and/or responsiveness to a specific therapy of a disease or resistance to a drug. The methods described here can also be used to detect the co-occurrence of particular nucleic acid sequences, which can indicate genomic recombination, co-expression of particular splice variants, co-expression of particular light and heavy chains in B cells. The methods are also applicable to detecting presence of a particular pathogen in a particular host cell, e.g., where both pathogen-specific and host cell-specific nucleic acids (or other parameter) co-occur in the same cell. The methods can also be employed for targeted re-sequencing from circulating tumor cells, e.g., at mutation hot spots in different cancers.

Kits

Kits according to the invention can include one or more reagents useful for practicing one or more assay methods described herein. A kit generally includes a package with one or more containers holding the reagent(s) (e.g., primers and/or probe(s)), as one or more separate compositions or, optionally, as admixture where the compatibility of the reagents will allow. The kit can also include other material(s) that may be desirable from a user standpoint, such as a buffer(s), a diluent(s), a standard(s), and/or any other material useful in sample processing, washing, or conducting any other step of the assay.

Kits generally include instructions for carrying out one or more of the methods described herein. Instructions included in kits can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), RF tags, and the like. As used herein, the term "instructions" can include the address of an internet site that provides the instructions.

It is understood that the examples and embodiments described herein are for illustrative purposes only and that various modifications or changes in light thereof will be suggested to persons skilled in the art and are to be included within the spirit and purview of this application and scope of the appended claims.

In addition, all other publications, patents, and patent applications cited herein are hereby incorporated by reference in their entirety for all purposes.

EXAMPLES

Example 1

Method to Prepare Nucleic Acids for Sequencing from Single Cells Using AccessArray™ IFC Adapted for Cell Handling ("MA006")

Summary of General Approach

A "chip," herein referred to as MA006, has been developed using the AccessArray™ platform as have methods using MA006 that integrate cell handling and sample preparation for nucleic acid sequencing. See FIG. 1 for a schematic diagram of the MA006 unit cell architecture, showing on-chip processes. This integration simplifies the steps required to execute the experiment. Moreover, only hundreds of cells are required to load the chip.

The MA006 chip has the following features:
Unit cell with 170×30 pm rounded channel to load mammalian cells
48.48 matrix format;
Use heat to lyse cells in cell channels;
Separate reaction chamber for amplification reaction;
170×170 pm containment valves to close cell channels;
Extra resist layer: PourOB-30 gm rounded resist;
Chip fabrication: Use current AA48.48 processes;
65 pm alignment tolerance;
130 pm punch diameter;
65×85 pm valve size; and
3-layer design process.
There are no cell capture features on the MA006 chip. The result is that a limiting dilution strategy is used to obtain the desired number of cells per chamber. However, cell capture features can be designed into the chip. They can be physical (for example, cups, or chalice structures), biological (for example, spotted peptides), or chemical (for example, charged ions).

Cell Handling off of the chip: Cells to be analyzed are prepared to a density such that a desired number of cells per sample chamber ("cell channel" in FIG. 1) is obtained. Since the MA006 chip uses a limiting dilution strategy, the number of cells per chamber follows a Poisson distribution, both theoretical and real. Since, in the first instance, a maximum number of chambers containing a single cell was desired, the optimal cell density was 300-600 cells per microliter. Minimal volumes of one to two microliters can be applied to the inlets. Therefore, experiments can be carried out with only hundreds of cells. Any cell type (i.e., mammalian, bacterial, etc.) from any source can be used (i.e., living organisms, tissue culture, etc.). Any form or extent of preparation, washing, and/or staining can be used, as long as this is compatible with downstream applications.

Cell tracking in the chip: In the absence of any polymerase/amplification dependent chemistry, the cells in the chip can be monitored for position, identity, and/or content using brightfield or fluorescence microscopy. The cells can be stained with any stain (i.e., nucleic acid-specific staining, such as SYT010; immunodetection, such as Cy5 conjugated anti-CD19; etc.) as long as this is compatible with downstream applications. This can be used, for example, to identify rare cells, i.e. cancer stem cells, in a heterogeneous cell population.

Chemistry: After the cells are loaded into the MA006, the assays are loaded in the assay chamber ("assay channel" in FIG. 1), and the interface valves are released to mix the contents of the sample and assay chambers. The chip is subjected to thermal cycling according to the selected chemistry and imaged in real-time or at the end point if this is required and/or supported by the chemistry. This procedure is not limited to gene-specific amplification, i.e. non-specific degenerate primers can be used, or RNA-specific amplification can be carried out. In the case of gene-specific amplification, more than one gene can be targeted simultaneously using a "multiplex" strategy. The chemistry is flexible, provided that the output is a substrate for sequencing, and should not be restricted to polymerase chain reaction or even amplification.

Figure 2:
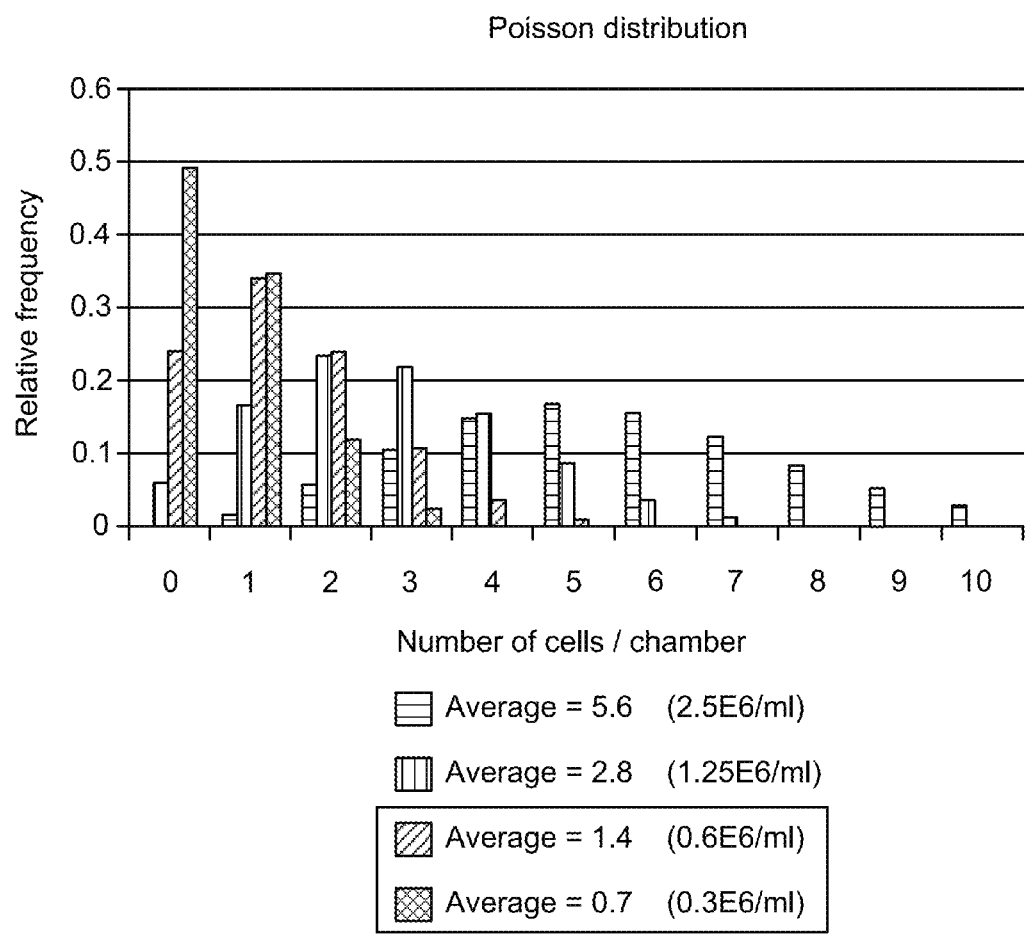
FIG. 2: The use of limiting dilution of a cell suspension to obtain a single cell per separate reaction volume ("chamber" of a microfluidic device or "chip"). The theoretical distribution (Poisson distribution) for various cell densities is shown.
Figure 3A:
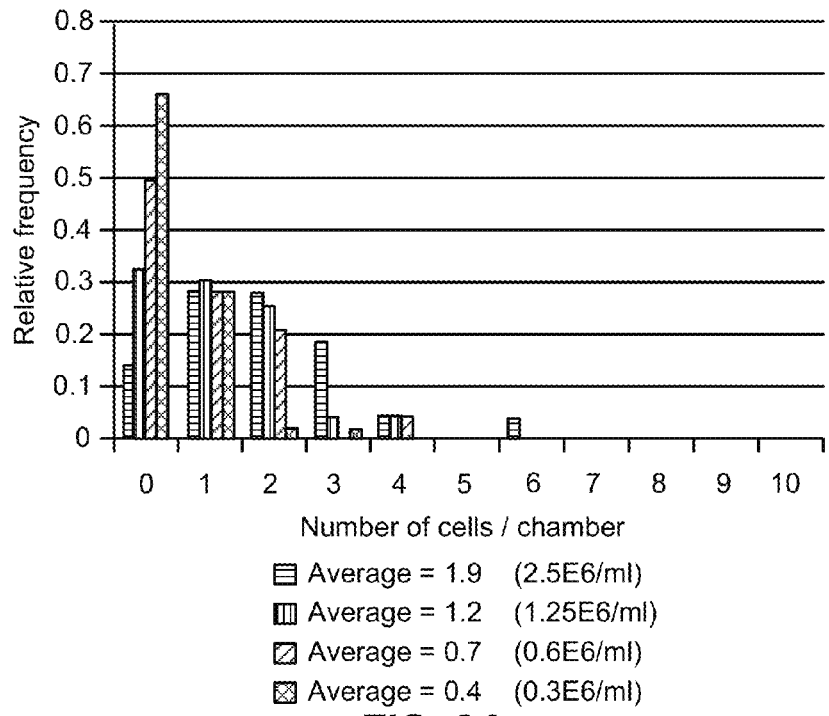
FIG. 3A-B: The results of cell counting in a chip using brightfield (A) to image, as compared to the theoretical distribution (B). Cell density in the chip, based on brightfield imaging, is close to, but lower than, the Poisson distribution, with this tendency exacerbated at higher cell densities.
Figure 3B:
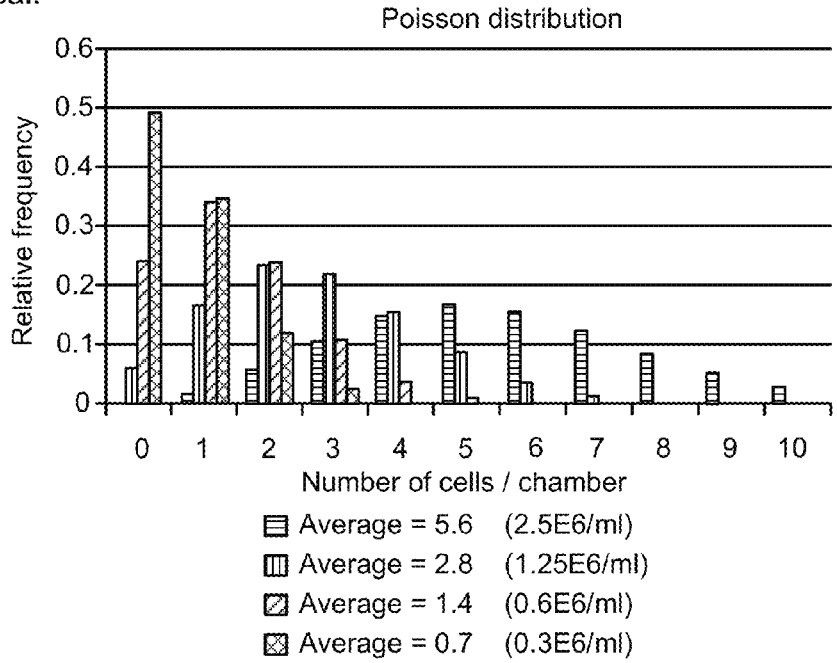

Cell Handling
Cell Counting: Brightfield Imaging
RAMOS cells were handled as follows:
(1) Harvest cells.
(2) Wash 2-3× in ice-cold Tris Saline BSA buffer.
(3) Count and make appropriate dilution. The theoretical distribution (Poisson distribution) for various cell densities is shown in FIG. 2.
(4) Push cells into MA006 chip.
(5) Image by brightfield.
FIG. 3A-B shows the results of cell counting in the chip using brightfield (A) to image, as compared to the theoretical distribution (B). Cell density in the chip, based on brightfield imaging, is close to, but lower than, the Poisson distribution, with this tendency exacerbated at higher cell densities. This may be due, in part, to "shadowing" created by chip features, which can reduce the measurable area within which cells can be detected using brightfield imaging.

Figure 4A:
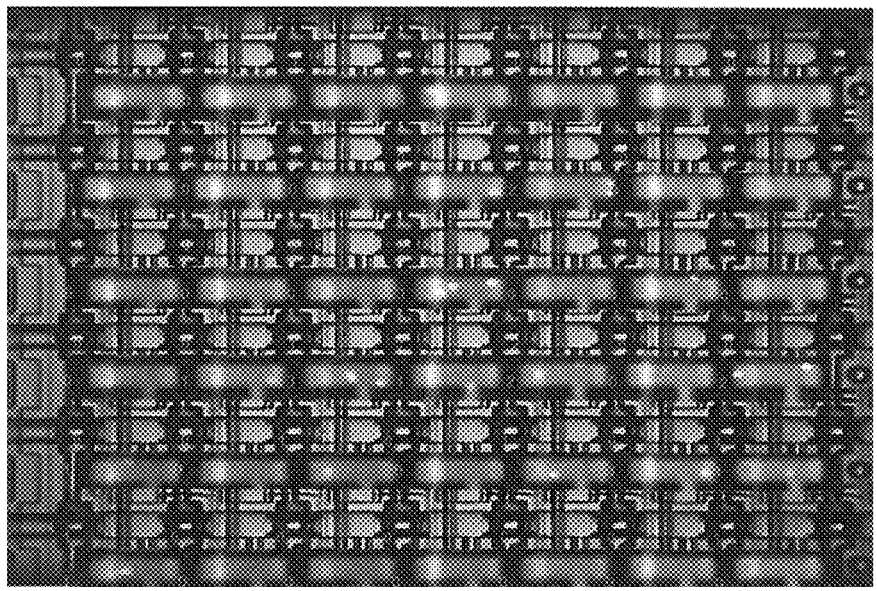
FIG. 4A-B: Fluorescent cell "ghost" images (A) permit detection of more cells than pre-PCR brightfield imaging, so that the cell density more closely approximates the Poisson distribution (B).
Figure 4B:
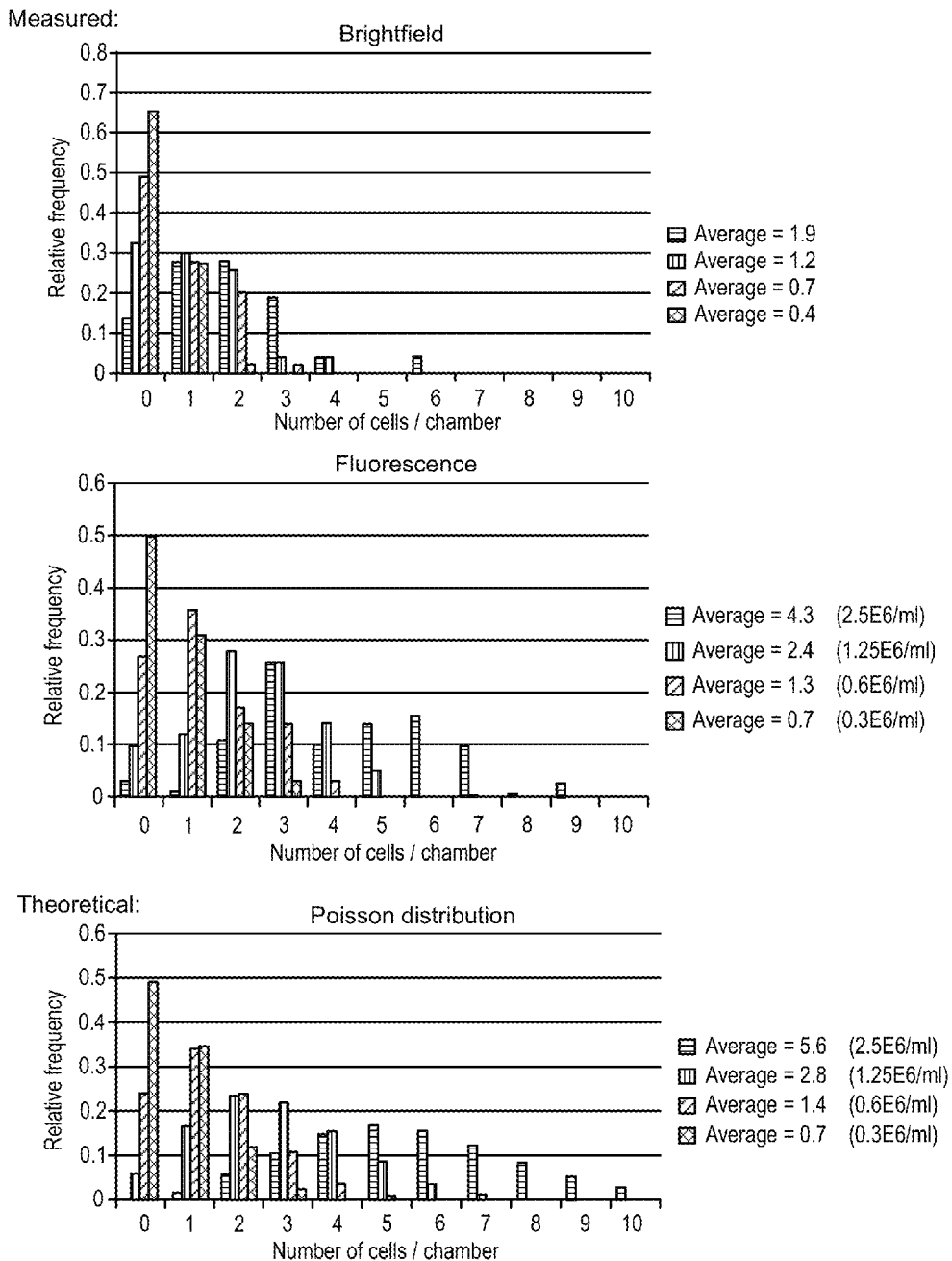

Cell Counting: Post-PCR Fluorescence
Cells were loaded into the MA006 chip at 0.15E6/ml and subjected to RT-PCR using Cells-Direct™ RT PCR components, Rox, and EVA green. FIGS. 4A-B show that fluorescent cell "ghost" images (A) permit detection of more cells then pre-PCR brightfield, so that the cell density more closely approximates the Poisson distribution (B). Based on these results, if 4000 cells are applied per inlet (e.g., 4 µl of 1000 cell/µl) of the MA006 chip and distributed throughout, approximately ⅓ of 2304 (48×48) or 800 chambers have a single cell.

More Specific Approaches

More specific methods for detecting cells in the chip that can be used include, e.g., the use of a cell membrane-permeant nucleic acid stain and/or cell-specific surface marker detection with an antibody. Thus, for example, RAMOS cells could be handled as follows:

(1) Harvest cells.
(2) Wash 2-3× in ice-cold Tris Saline BSA buffer.
(3) Stain with Syto10 DNA stain and/or Cy5-labeled anti-CD19 antibodies.
(4) Wash 2-3× in ice-cold Tris Saline BSA buffer.
(5) Count and make appropriate dilution.
(6) Push cells into MA006 chip.
(7) Image.

Figure 5:
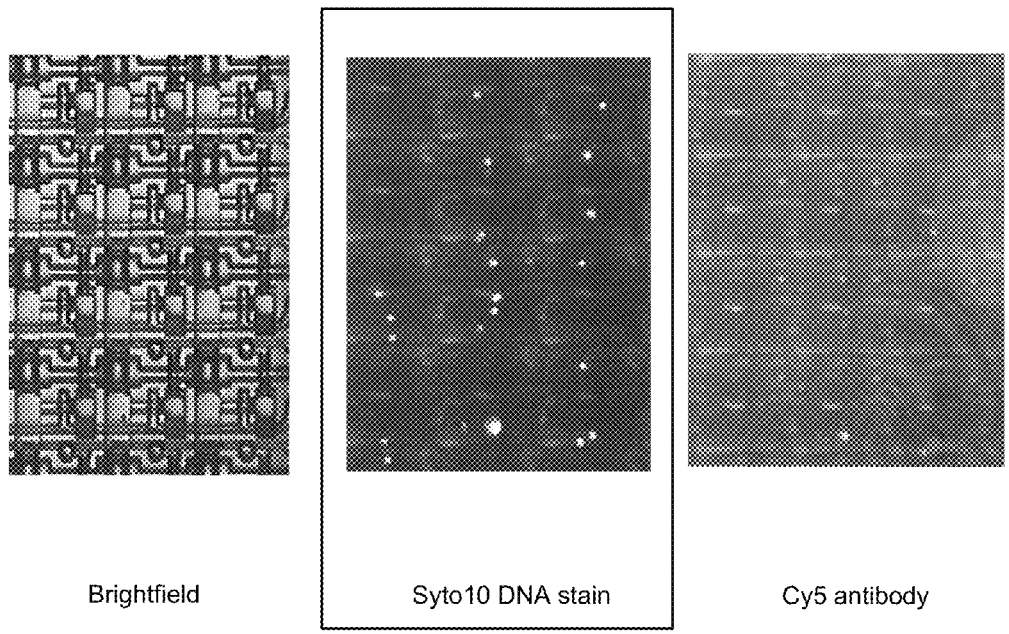
FIG. 5: Specific methods for detecting cells in a chip that can be used include, e.g., the use of a cell membrane-permeant nucleic acid stain and/or cell-specific surface marker detection with an antibody. The results of these more specific approaches are shown for a cell density of 1E6/ml.
Figure 6A:
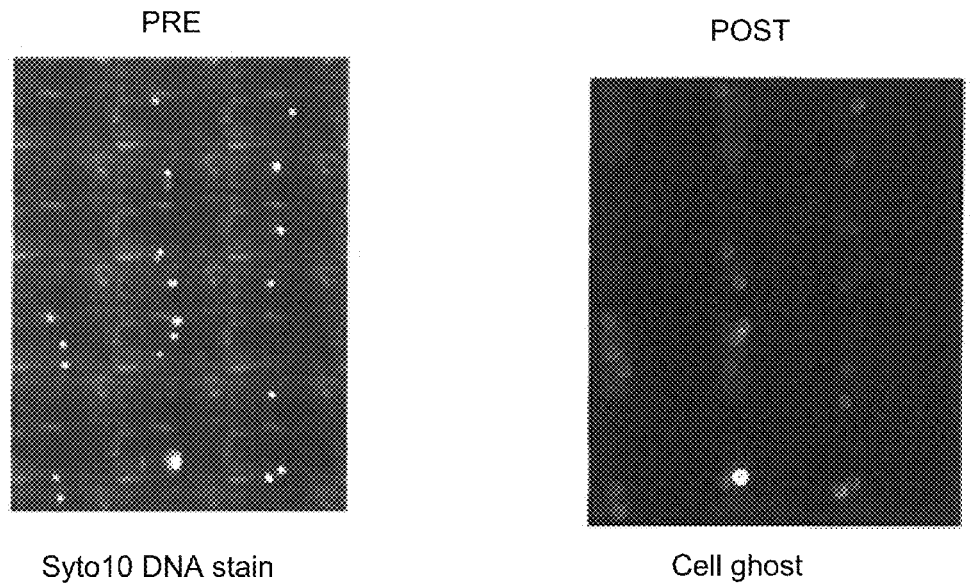
FIG. 6A-B: (A) A comparison the use of pre-RT-PCR nucleic acid stain (Syto10 DNA stain) to detect cells in a chip versus post RT-PCR ghost images (Cell ghost). (B) Syto10 does not inhibit RT-PCR of GAPDH.
Figure 6B:
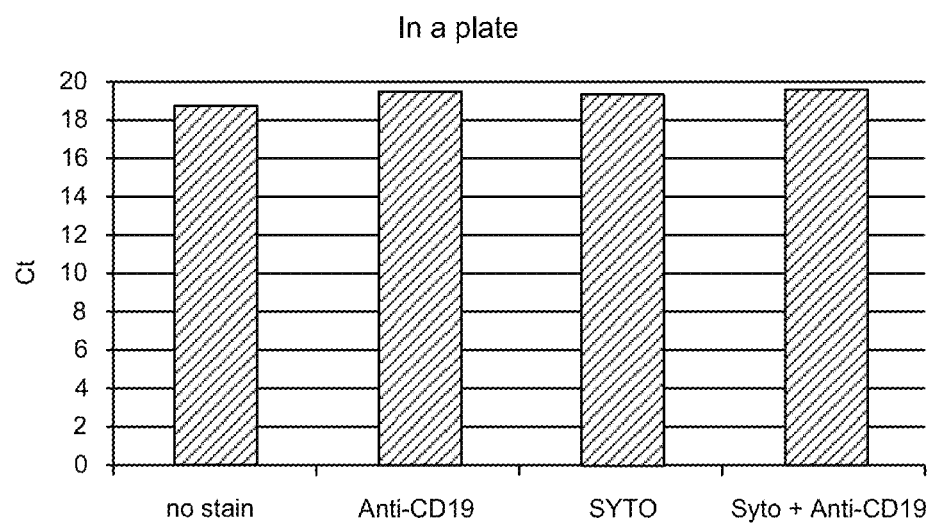

The results of these more specific approaches are shown for a cell density of 1E6/ml in FIG. 5. FIG. 6A shows a comparison between pre-RT-PCR nucleic acid stain (Syto10 DNA stain) versus post RT-PCR ghost images (Cell ghost), and FIG. 6B shows that Syto10 does not inhibit RT-PCR of GAPDH. A proposed workflow for cell detection in the chip could include staining cells with a DNA stain and/or antibody, followed by counting pre-RT-PCR and then counting cell ghosts as a back-up post-RT-PCR.

Chemistry: One-Step Gene-Specific RT-PCR

Figure 7:
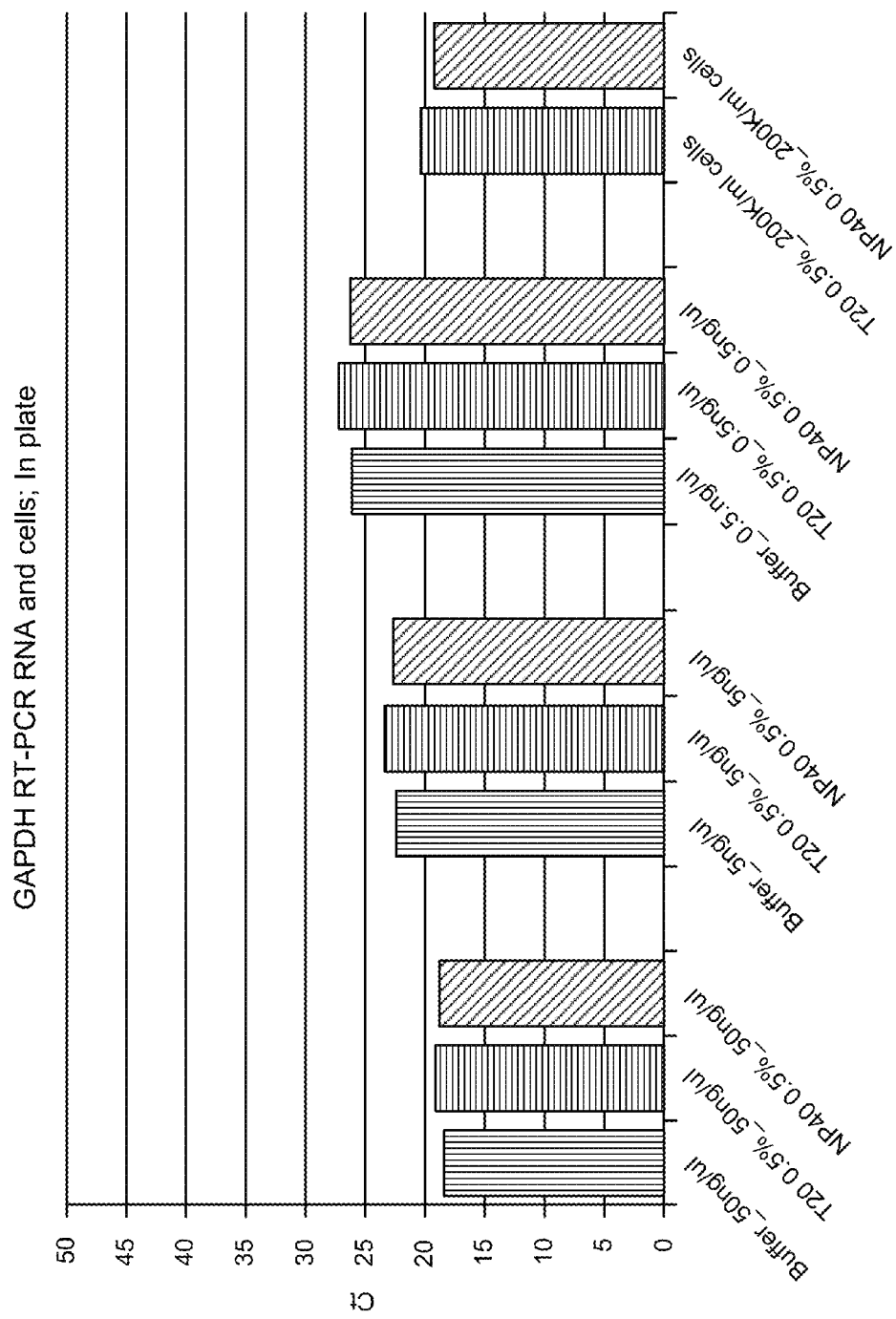
FIG. 7: RT-PCR of GAPDH carried out in the presence of 0.5% Tween 20 or 0.5% NP40 (the latter is a cell lysis reagent). Neither inhibited RT-PCR of GAPDH significantly

Different chemistries were investigated to find an efficient chemistry to convert gene-specific RNA in cells into amplicons in the MA006 chip. Cells are pushed into cell channels in Tris Saline BSA (0.5 µg/ml) buffer. Reagents loaded into assay channels included:

Primers (500 nM final concentration)
CellsDirect™ One-Step qRT-PCR kit components (available from Life Technologies, Foster City, Calif.)
Reaction Mix
Enzyme Mix: Superscripte III+Platinum Taq Polymerase
Buffer
Rox
EVA Green
Loading Reagent—AA or GE (available from Fluidigm Corp., South San Francisco, Calif.) to prevent non-specific absorption by PDMS ("depletion effect") and to lyse cells. RT-PCR of GAPDH was carried out with or without AA or GE loading reagent. The results showed that both loading reagents inhibited RT-PCR. The loading reagents contain: Prionex (AA) or BSA (GE) and 0.5% Tween-20. RT-PCR of GAPDH was carried out in the presence of Prionex or BSA. Prionex, but not BSA, was found to inhibit RT-PCR. RT-PCR of GAPDH was carried out in the presence of 0.5% Tween 20 or 0.5% NP40 (the latter is a cell lysis reagent). The results of this study are shown in FIG. 7. Neither 0.5% Tween 20 or 0.5% NP40 inhibited RT-PCR of GAPDH significantly.

Figure 8:
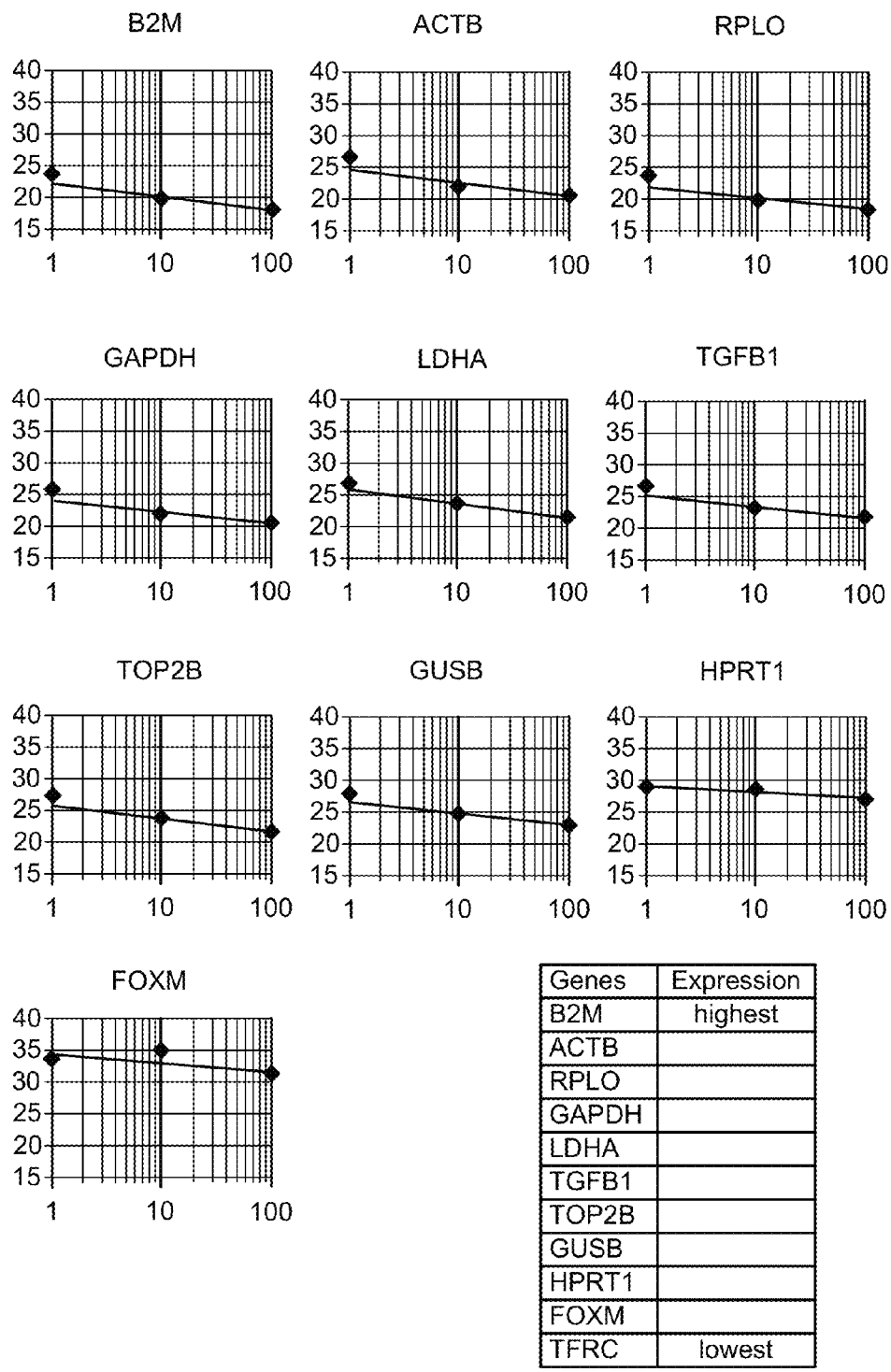
FIG. 8: Standard curve amplification of 11 genes, carried out in the MA006 chip. These results demonstrate that the CellsDirect™ One-Step qRT-PCR kit can be used with 0.5% NP40 (for cell lysis and to prevent the depletion effect in the chip) to convert gene-specific RNA in cells into amplicons in an MA006 chip.

To determine that the reaction conditions developed for RT-PCR of GAPDH from cells would permit RT-PCR of other genes, expressed at different levels, RT-PCR of 11 genes covering a range of expression levels was carried out with 10 ng/µl of RNA and the reagents described above, except that 0.5% NP40 was substituted for AA/GE Loading Reagent. The thermal protocol was 50° C. for 30 minutes; 55° C. for 30 minutes; 95° C. for 2 minutes; and then 45 cycles of: 95° C. for 15 seconds, 60° C. for 30 seconds, and 72° C. for 60 seconds. Standard curve amplification of these 11 genes, carried out in the MA006 chip, is shown in FIG. 8. These results demonstrate that the CellsDirect™ One-Step qRT-PCR kit can be used with 0.5% NP40 (for cell lysis and to prevent the depletion effect in the chip) to convert gene-specific RNA in cells into amplicons in the MA006 chip.

Sequencing

Figure 9:
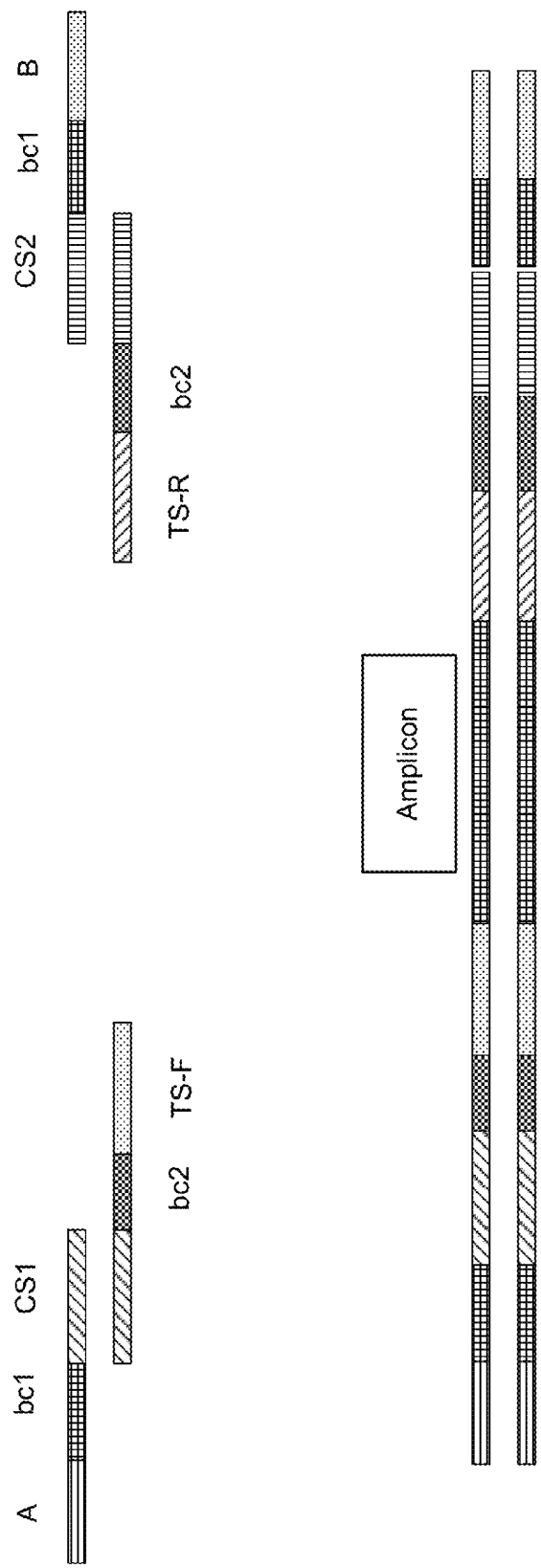
FIG. 9: A four-primer, combinatorial barcoding method was employed to put a combination of two barcodes on either end of each amplicon Inner primers include target-specific portions ("TS-F" in the forward primer and "TS-R" in the reverse primer), a barcode nucleotide sequence ("bc2"), and different nucleotide tags. Outer primers include tag-specific portions ("CS1" and "CS2"), a different barcode nucleotide sequence ("bc1"), primer binding sites for sequencing primers ("A" and "B").
Figure 10A:
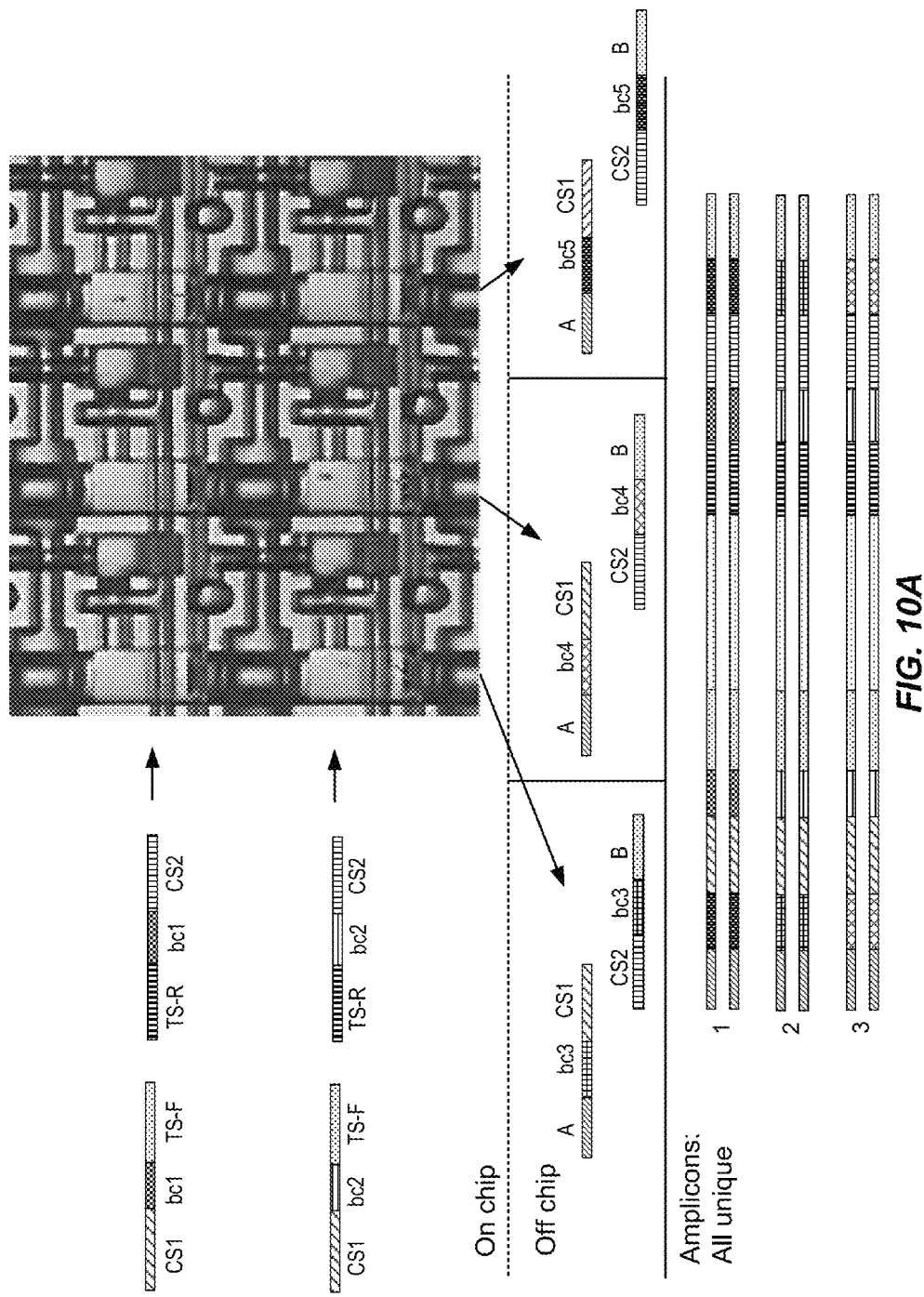
FIG. 10A-B: An illustration of how 4-primer barcoding can be carried out on a chip, such as the MA006. (A) Amplification is carried out on-chip with inner primers, where each row of chambers has the same pair of inner primers with the same barcode. (B) Reaction products from each column of chambers can be harvested as a pool and each pool subjected to amplification using a different pair of outer primers. This amplification produces amplicons having barcode combinations at either end of the amplicon that uniquely identify the chamber (by row and column) in which the initial amplification was carried out.
Figure 10B:
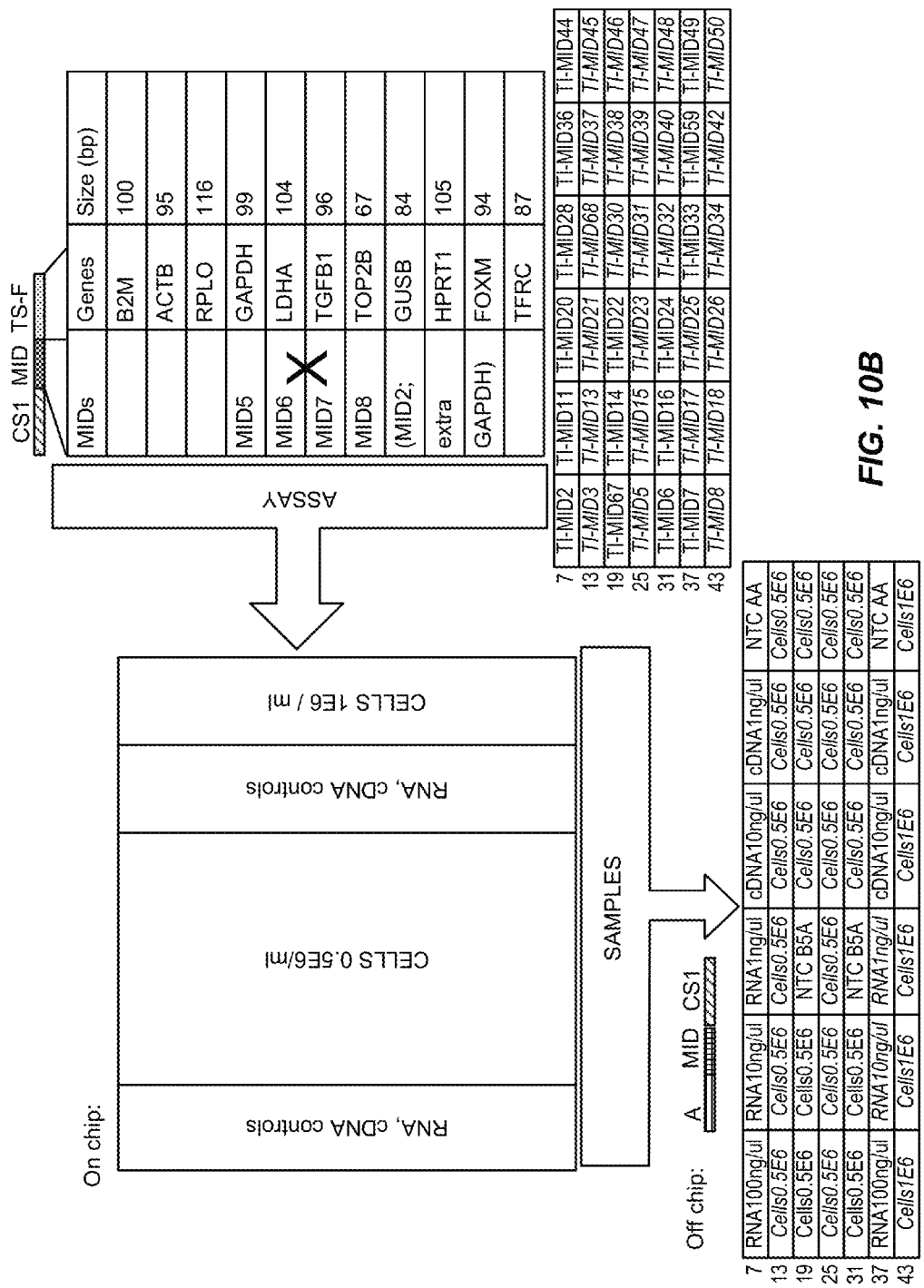
Figure 11:
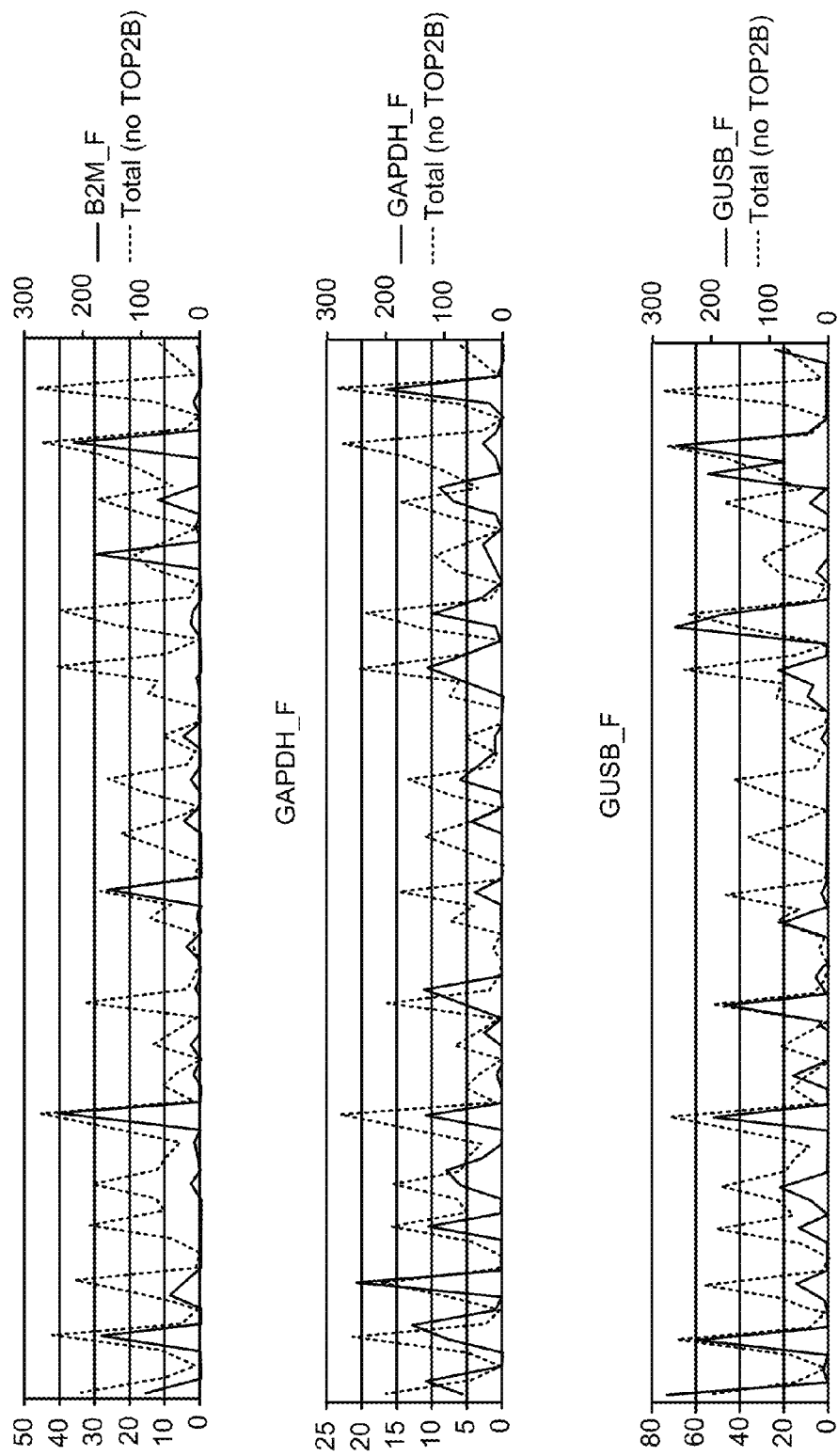
FIG. 11: A comparison of the results obtained upon sequencing gene-specific amplicons from single cells (Example 1), expressed as number of reads for each gene-specific amplicon (red), as compared to that for total RNA. As is apparent from this figure, the representation of these RNAs is different when measured in individual cells, as compared to that observed in the total RNA.

To facilitate sequencing of gene-specific amplicons generated in the MA006 chip, a barcoding method was employed to distinguish amplicons from different chambers (e.g., cells). More specifically, a four-primer, combinatorial barcoding method was employed to put a combination of two barcodes on either end of each amplicon. This method is shown schematically in FIG. 9. Inner primers include target-specific portions ("TS-F" in the forward primer and "TS-R" in the reverse primer), a barcode nucleotide sequence ("bc2"), and different nucleotide tags. Outer primers include tag-specific portions ("CS1" and "C52"), a different barcode nucleotide sequence ("bc1"), and primer binding sites for sequencing primers ("A" and "B"). FIG. 10A-B illustrates how 4-primer barcoding can be carried out on a chip, such as the MA006. Amplification is carried out on-chip with inner primers, where each row of chambers has the same pair of inner primers with the same barcode. Reaction products from each column of chambers can be harvested as a pool and each pool subjected to amplification using a different pair of outer primers. This amplification produces amplicons having barcode combinations at either end of the amplicon that uniquely identify the chamber (by row and column) in which the initial amplification was carried out. The reaction products were sequenced and the number of reads of each sequence for each reaction chamber was determined. This determination was carried out for RAMOS cells and for spleen RNA. FIG. 11 shows a comparison of the results obtained, expressed as number of reads for each gene-specific amplicon (red), as compared to that for total RNA. As is apparent from this figure, the representation of these RNAs is different when measured in individual cells, as compared to that observed in the total RNA.

Example 2

Size-Based Microfluidic Single-Particle Capture

Figure 12A:
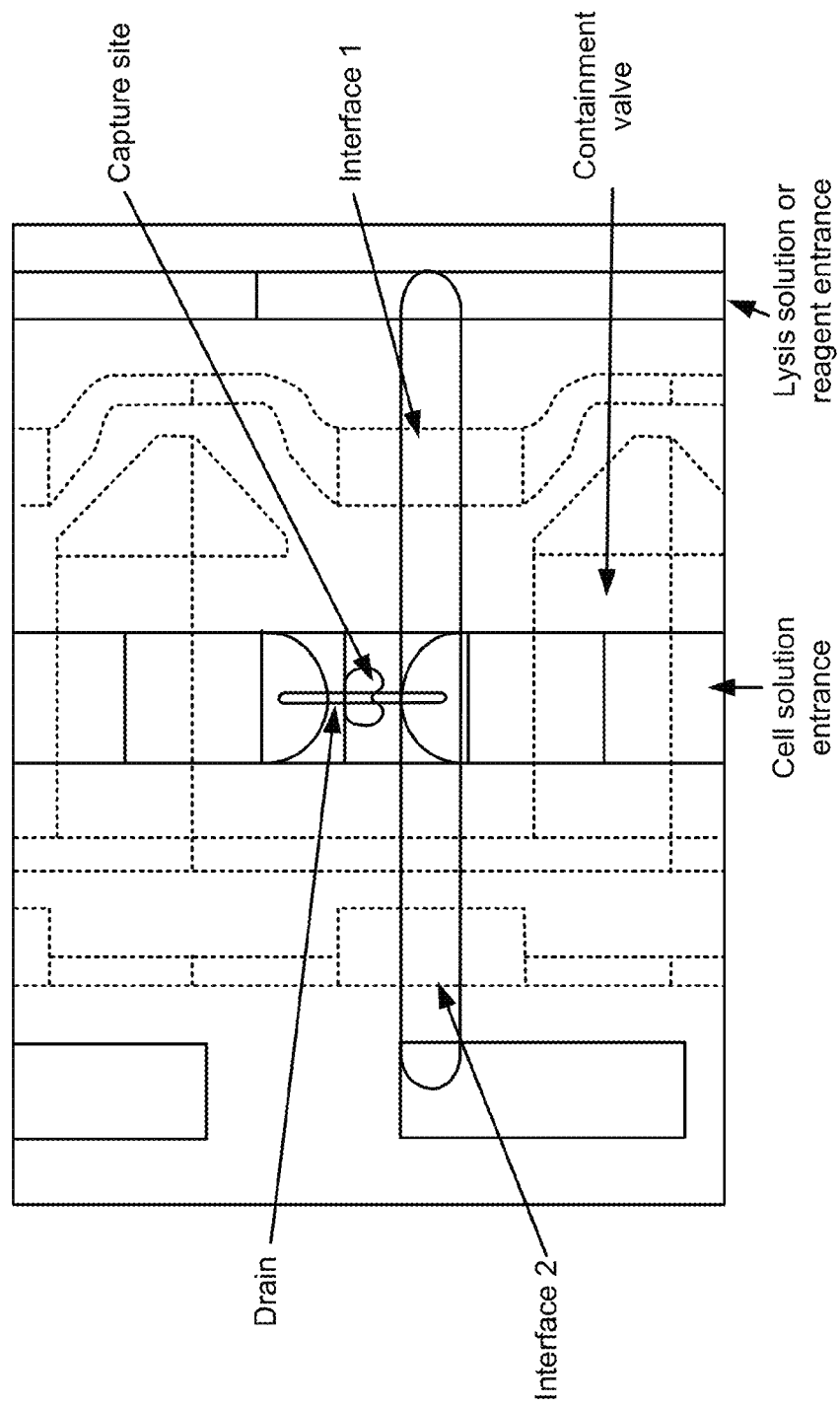
FIG. 12A-B: A capture site with a capture feature and drain. (A) A site without baffles to focus flow. (B) A site with baffles.
Figure 12B:
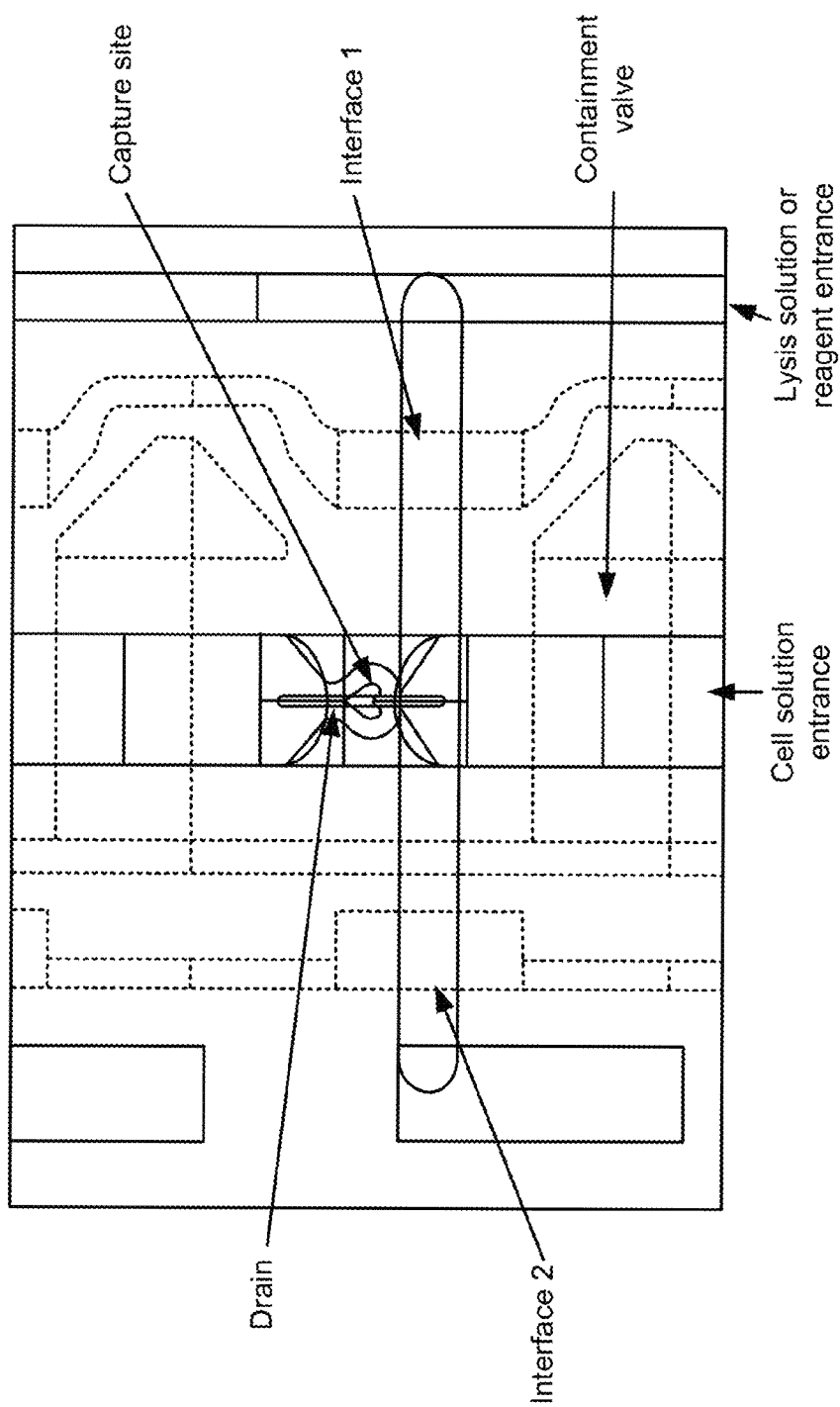
Figure 13:
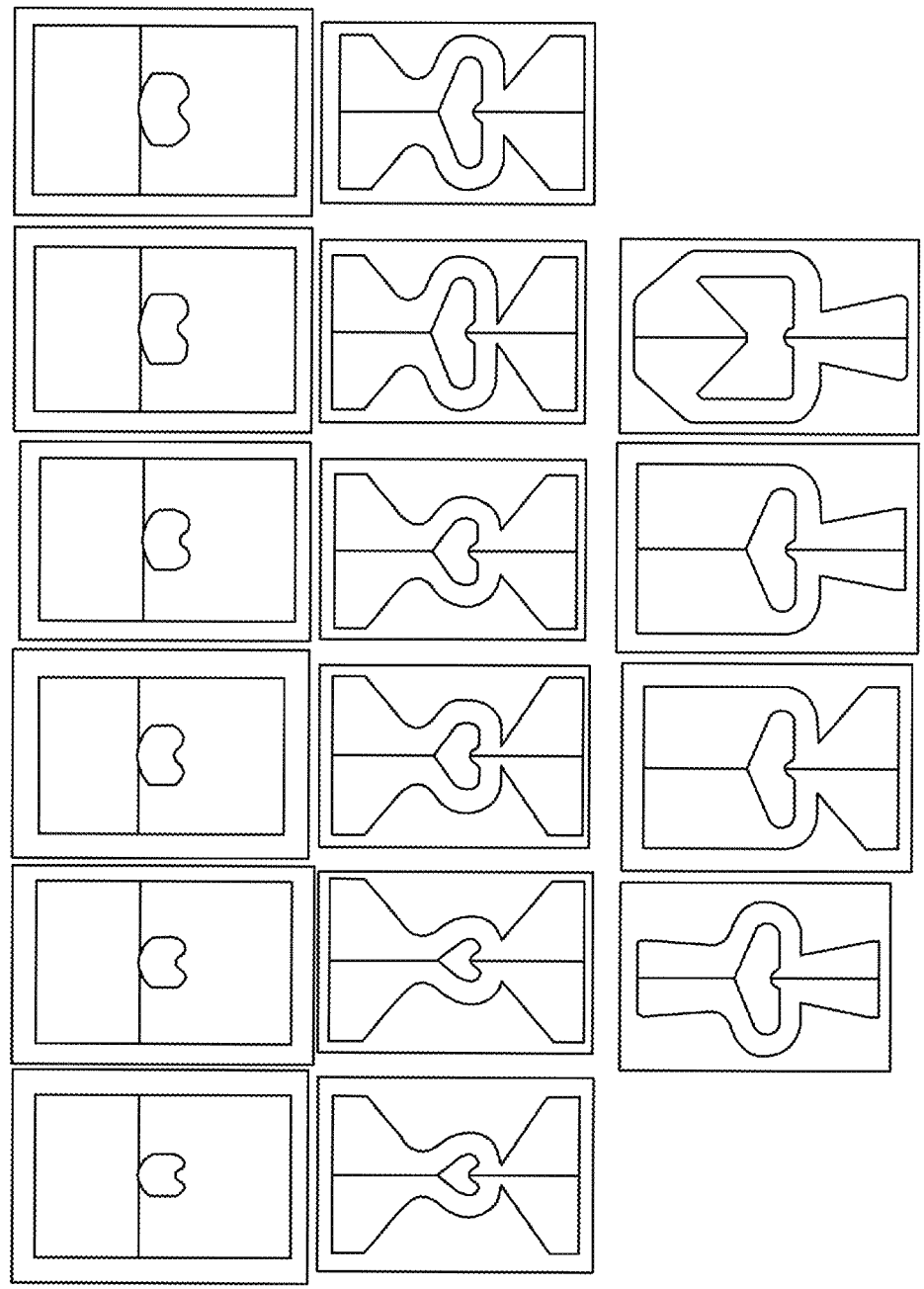
FIG. 13: Additional capture site designs are shown in FIG. 13.

One approach to discretely capturing single cells from suspension as they flow through a microfluidic device is to define a microfluidic geometry that guides flow of a suspension of particles (such as cells or beads) over a capture site in a manner that the capture site catches a single particle, efficiently captures single particles (e.g., the probability of the capture of a particle passing near a capture site is high), and/or guides the remaining suspension around the capture site. The proposed geometries can be size-based, i.e., the capture site is just large enough to contain one particle (and no more), but still permit the flow of particle-free suspension through the site at reasonably low fluidic impedance, such that an empty capture site would guide the flow of particles toward it rather than around it. This goal can be accomplished by the use of a drain. Additional proposed geometries can also focus the flow of particles in a manner that increases the likelihood of particles coming in close enough proximity to the capture site for high probability of successful capture. Variations on these geometries have focused on controlling the flow resistance of the fluidics surrounding the capture site and drain, including the drain itself, as well as varying the aperture of focusing geometry in attempts to position the flow of particles close to the capture site. FIG. 12A-B illustrates a capture site with a capture feature and drain. Panel A shows a site without baffles to focus flow, whereas panel B shows a site with baffles. Additional capture site designs are shown in FIG. 13.

Example 3

Surface Marker-Based Capture of Particles

Single-cell studies within microfluidic architectures require the isolation of individual cells into individual reaction partitions (chambers, droplets, particles). Limiting dilution is one method for achieving this isolation. Cells are loaded at concentrations of less than one cell per partition on average, and distribute into those partitions in a pattern described by Poisson statistics. Another approach is to rely on mechanical traps to capture cells. These traps are designed to capture cells of a given size range (see Example 2). This results in a biased selection of cells from the population within that size range.

For some applications, an ideal capture method would use biological markers expressed on the surface of cells. Antibodies can be patterned in specific locations on a microfluidic array, although this approach may not be simple, depending on the structure of the microfluidic array.

This example describes a method for capture of single particles (e.g., cells) based on the initial capture of a single, affinity-reagent-coated bead in a specific location in a microfluidic device. The surface area presented by this bead at the opening of a capture site provides a defined surface of affinity reagent accessible for cell binding. The bead size and capture site can be chosen/designed such that once a single cell is bound to the bead, the rest of the accessible surface area of the bead is sterically blocked by the first-bound cell. Selection of an appropriate sized bead capture site also provides for capture of a broad range of cell sizes. As long as the cell is larger than the exposed capture area, and expresses the appropriate surface marker or binding partner for the affinity reagent, it should be possible to capture that cell.

Figure 14B:
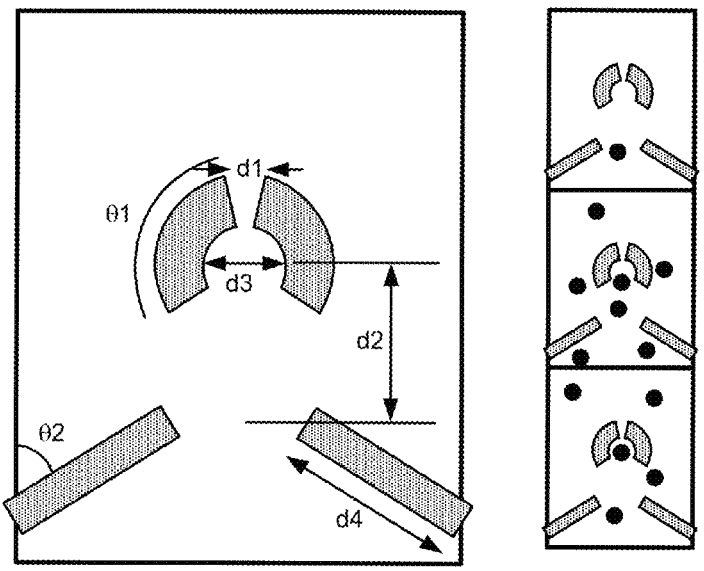
Figure 14C:
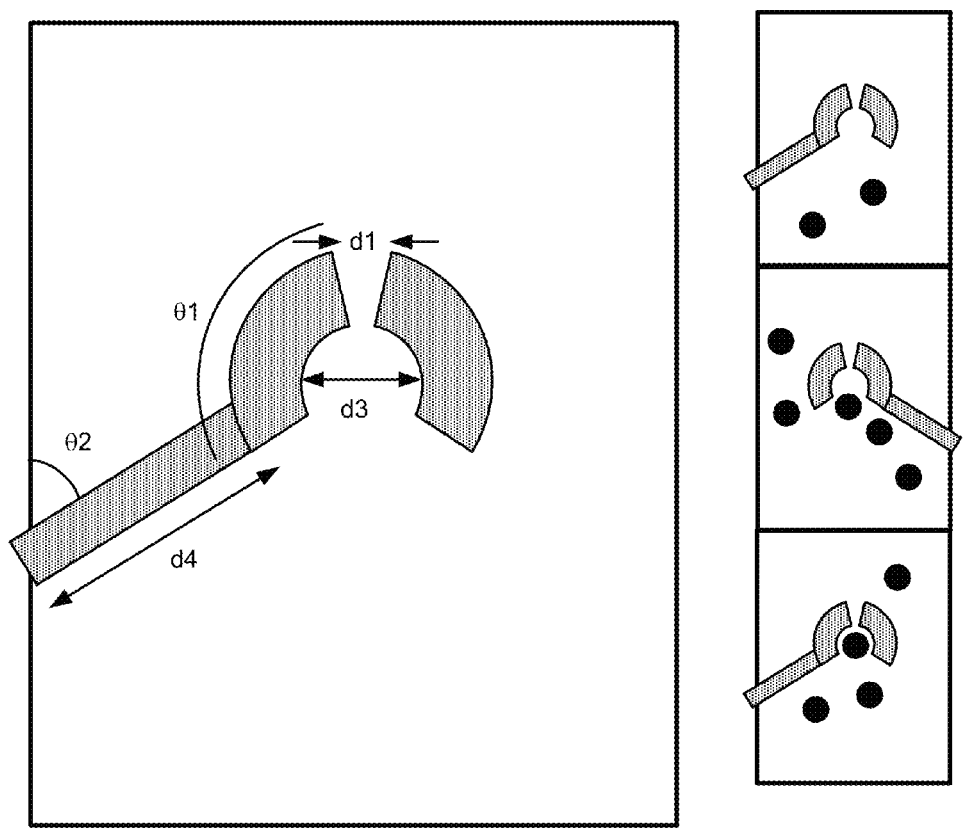

Capture architectures can be designed to maximize the probability that cells will come into contact with the surface markers. For example, baffles on one or more channel walls can be used to direct beads towards capture feature. See FIG. 14A for illustrative capture feature/baffle combinations. Performance of the capture feature can be adjusted by adjusting one or more variables, including angle of baffles, distance of baffles from capture site, length of baffles, size and shape of capture feature, size of drain in capture feature (if present). See FIGS. 14B and C illustrating the variables for, and performance of, capture feature/baffle combinations. In FIG. 14B, baffles on the channel wall are used to direct beads towards a capture feature. In FIG. 14C, the capture feature is coupled to a baffle on a channel wall; individual capture feature/baffle combinations can be located on alternate walls to focus flow towards the adjacent capture feature/baffle combination. These combinations can be located at sites that, in use, are separable (e.g., using valves) to form separate reaction chambers.

Figure 15B:
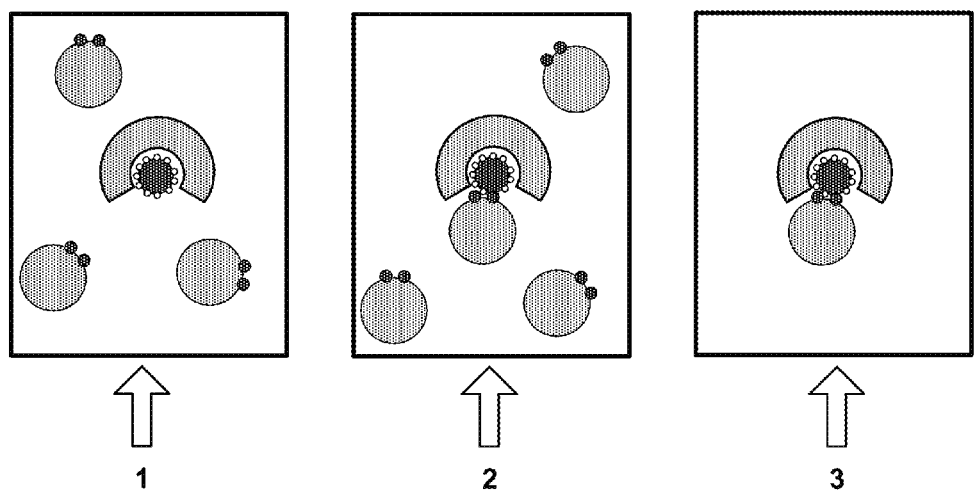

FIGS. 15A and B illustrate (in simplified form, lacking baffles) a strategy for using capture features to catch single, affinity-reagent-coated beads, which then display the affinity reagent (e.g., antibody) so as to capture single particles (e.g., cells). In FIG. 15A-1, flow is initiated in a channel containing capture features. In panel A-2, antibody-bound beads flow toward the capture features until a bead lodges in the capture feature, as shown in panel A-3. The channel is then washed to remove non-captured beads. Subsequently, as shown in FIG. 15B-1, cells bearing a cell-surface marker to which the antibody binds are flowed into the channel containing the captured beads. Panel B-2 illustrates how cells bearing the marker interact with and bind to antibodies displayed by the captured bead. The display area is sized so that a bound cell will inhibit other cells from interacting with the captured bead through steric occlusion, such that only one cell binds to each captured bead. The channel is then washed to remove non-bound cells, as shown in panel B-3, leaving one cell immobilized at each capture site.

Example 4

Microfluidic Device for Cell Capture ("CCap")

Figure 16A:
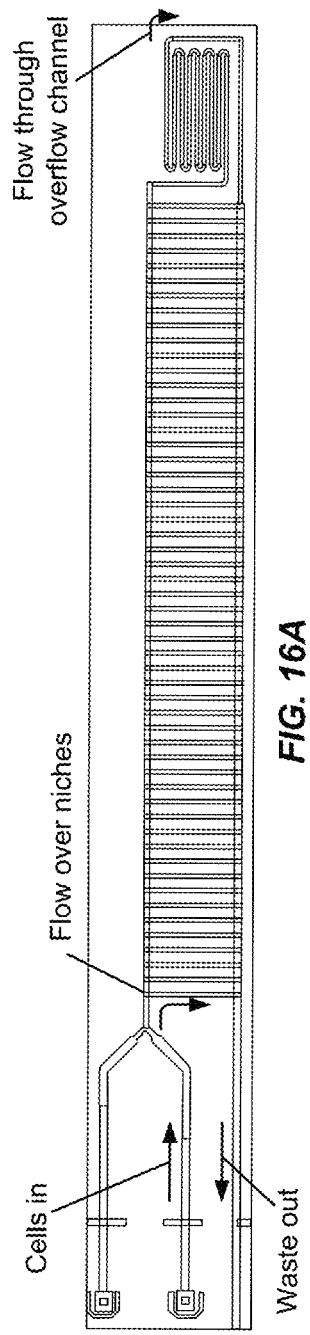
FIG. 16A-G: (A) A schematic of a microfluidic device designed to capture single cells at discrete locations (niches). Single cell capture allows analysis of biological events at the single cell level. (B) Flow is designed to be stronger over niches than through an overflow channel. Niches contain small gaps (~3 μm tall). When a cell enters a niche, it blocks the niche and prevents any more flow into the niche. Flow passes through to the next unoccupied niche, until it too is blocked by a cell. Every niche should capture one cell before cells pass through the overflow channel and out to waste. (C) Schematic of (A) shown with additional detail provided in (D)-(F). (D) A buffer inlet converges with a cell inlet so as to force cells to a side of a feeder channel that is closest to a series of transverse cell capture channels. (E) The resistance of the transverse cell capture channels is lower than that of a cell overflow channel to induce preferential flow of cells into niches versus into the cell overflow channel. (F) Each niche is large enough to capture just one cell. A cell in a niche raises the resistance of that particular circuit, and flow is directed to the circuits without cells. (G) An actual device of (A), with captured human umbilical vein endothelial cells (HUVEC) located in niches.
Figure 16B:
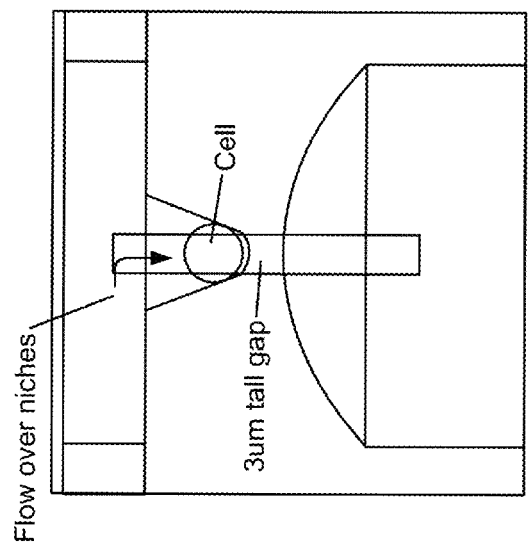
Figure 16C:
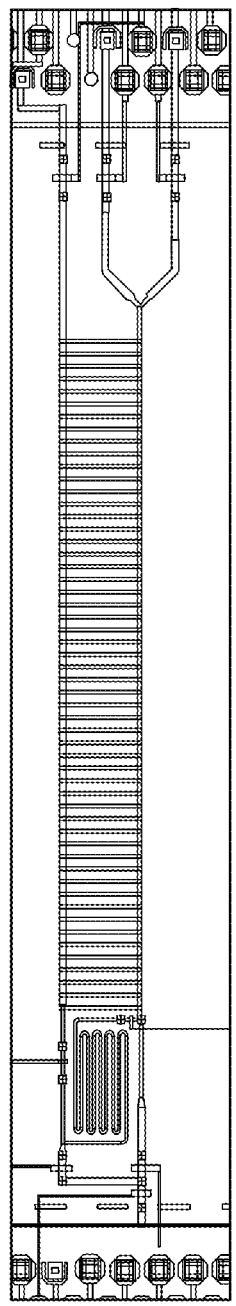
Figure 16D:
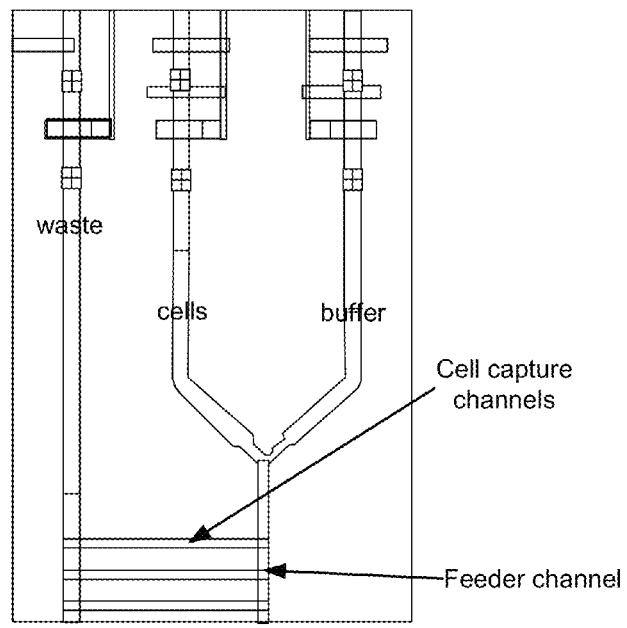
Figure 16E:
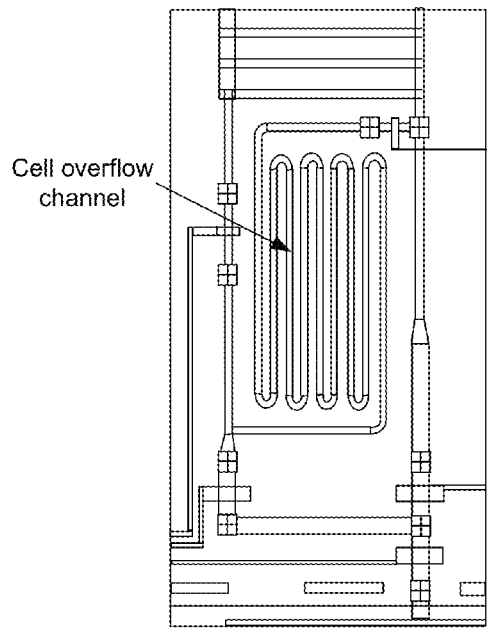
Figure 16F:
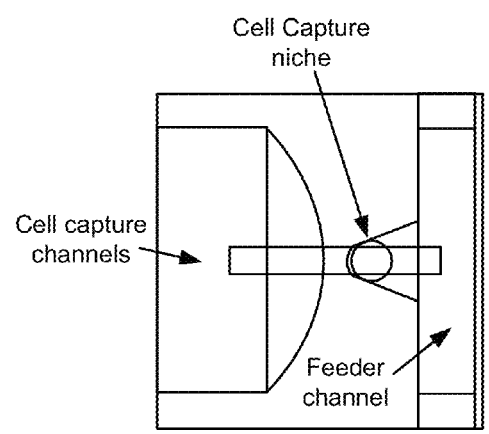
Figure 16G:
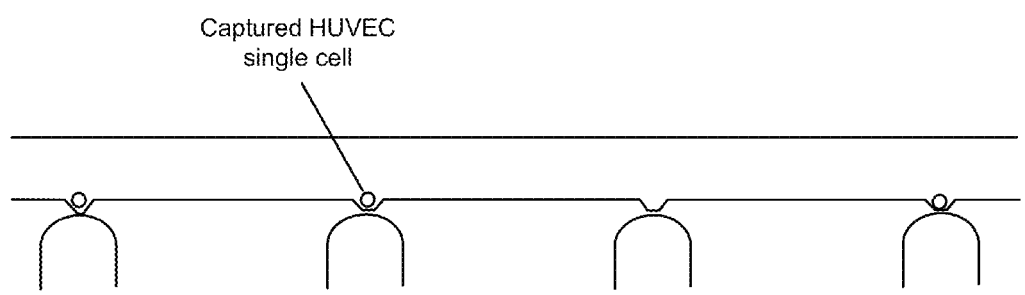

FIG. 16A shows a schematic of a microfluidic device designed to capture single cells at discrete locations (niches). Flow is designed to be stronger over niches than through an overflow channel. Niches contain small gaps (~3 µm tall). See FIG. 16B. When a cell enters niche, it blocks the niche and prevents any more flow into the niche. Flow passes through next unoccupied niche, until it too is blocked by a cell. In theory, every niche should capture one cell before cells pass through the overflow channel and out to waste. Referring to FIG. 16C-F for more detail, a buffer inlet converges with a cell inlet so as to force cells to a side of a feeder channel that is closest to a series of transverse cell capture channels. See FIG. 16D. The resistance of the transverse cell capture channels is lower than that of a cell overflow channel to induce preferential flow of cells into niches versus into the cell overflow channel. See FIG. 16E. As shown in FIG. 16F, each niche is large enough to capture just one cell. The niche gap is sufficiently small that cells are captured at the operational pressure/flow levels. If the latter are too high and/or the niche gaps are too large, cells may deform and be pushed through the niche gaps. The presence of a cell in a niche raises the resistance of that particular circuit, and flow is therefore directed to circuits without cell. FIG. 16G shows an actual device with captured human umbilical vein endothelial cells (HUVEC) located in niches.

What is claimed is:

1. A method of producing a data set comprising a plurality of parameters for single particles in a plurality of particles, wherein each of said single particles comprises one or more target nucleic acids, said method comprising:
    capturing particles of said plurality of particles in separate compartments of a microfluidic device, thereby producing a plurality of separate reaction volumes in the separate compartments of the microfluidic device such that at least 35% of said separate reaction volumes comprise only a single particle of said plurality of particles, the separate compartments being arranged as an array defined by rows and columns;
    determining which of said separate reaction volumes comprise only a single particle of said plurality of particles by microscopy and/or using a stain, dye, or label;
    performing a plurality of reactions in each of said separate reaction volumes, thereby producing a plurality of reaction products in each of said separate reaction volumes, wherein at least one reaction of the plurality of reactions in each of said separate reaction volumes comprises a nucleic acid amplification reaction that produces at least one amplicon in each of said separate reaction volumes, wherein the at least one amplicon in each of said separate reaction volumes is produced using amplification primers, wherein each of at least two of the amplification primers comprises a barcode nucleotide sequence, the at least one amplicon comprising a combination of the barcode nucleotide sequence from each of the at least two of the amplification primers, wherein the combination of the barcode nucleotide sequence from each of the at least two amplification primers in the at least one amplicon in each of said separate reaction volumes identifies the row and column of a compartment of the separate compartments of the microfluidic device and thereby identifies the source of the at least one amplicon;

recovering the reaction products, comprising the at least one amplicon from each of said separate reaction volumes by pooling the reaction products from each of the separate reaction compartments, thereby producing pooled reaction products;

obtaining analysis results by analyzing the pooled reaction products;

generating analysis results for the single particles in the plurality of particles by disregarding the analysis results from said separate reaction volumes that contain no particle of said plurality of particles or contain more than one single particle of said plurality of particles; and producing the data set comprising the plurality of parameters for the single particles in the plurality of particles by associating the analysis results for the single particles in the plurality of particles with each of said separate reaction volumes that comprise only a single particle of the plurality of particles.

2. The method of claim 1, wherein said at least 35% of said separate reaction volumes that comprise only a single particle of said plurality of particles is at least 50% of the total number of said separate reaction volumes.

3. The method of claim 1, wherein said at least 35% of said separate reaction volumes that comprise only a single particle of said plurality of particles is at least 65% of the total number of said separate reaction volumes.

4. The method of claim 1, wherein said at least 35% of said separate reaction volumes that comprise only a single particle of said plurality of particles is at least 85% of the total number of said separate reaction volumes.

5. The method of claim 1, wherein the particles are captured in said separate reaction volumes prior to adding one or more reagents for performing said plurality of reactions in each of said separate reaction volumes.

6. The method of claim 1, wherein the particles are cells.

7. The method of claim 1, wherein the particles are nucleic acids.

8. The method of claim 1, wherein fewer than 40,000 of said particles are employed in the method.

9. The method of claim 1, wherein fewer than 10,000 of said particles are employed in the method.

10. The method of claim 1, wherein the number of said particles distributed in said separate reaction volumes is greater than 100.

11. The method of claim 1, wherein a limiting dilution of said particles is carried out before said capturing particles of said plurality of particles in separate compartments of the microfluidic device.

12. The method of claim 11, wherein said limiting dilution of said particles is carried out by:

preparing a series of dilutions of a suspension of said plurality of particles;

distributing the particles from each dilution of said series of dilutions into the separate compartments of a microfluidic device;

determining which of said separate compartments comprise only a single particle of said plurality of particles; and selecting the dilution that produces the highest number of said separate compartments that comprise only a single particle of said plurality of particles for use in said capturing single particles of said plurality of particles in separate compartments of the microfluidic device.

13. The method of claim 12, wherein the number of particles in each of said separate compartments is determined by brightfield microscopy or by fluorescence microscopy when the particles are labeled with a fluorescent dye or label.

14. The method of claim 12, wherein a stain, dye, or label is employed for determining which of said separate compartments comprise only a single particle of said plurality of particles.

15. The method of claim 14, wherein the particles are cells, and the stain, dye, or label is a membrane-permeant stain, dye, or label.

16. The method of claim 14, wherein the particles are cells, and said determining which of said separate compartments comprise only a single particle of said plurality of particles is by using a cell membrane-permeant nucleic acid dye.

17. The method of claim 14, wherein the particles are cells, and the stain, dye, or label is a cell-surface stain, dye, or label.

18. The method of claim 14, wherein the particles are cells, and said determining which of said separate compartments comprise only a single particle of said plurality of particles is by using a labeled antibody specific for a cell-surface marker.

19. The method of claim 1, wherein said capturing particles of said plurality of particles in separate compartments of the microfluidic device comprises mechanically capturing the particles of said plurality of particles at a plurality of capture sites in the separate compartments of the microfluidic device.

20. The method of claim 19, wherein each of said plurality of capture sites comprises:

a capture feature with a size holding only one single particle of said plurality of particles;

and a drain feature, wherein, when the capture feature is not occupied by the single particle, the drain feature permits a flow of fluid to pass through the capture site of said plurality of capture sites.

21. The method of claim 19, wherein the microfluidic device comprises a focusing feature to focus said plurality of particles to each of said plurality of capture sites.

22. The method of claim 19, wherein said capturing particles of said plurality of particles in separate compartments of the microfluidic device comprises passing a solution comprising said plurality of particles through the separate compartments of the microfluidic device.

23. The method of claim 1, wherein said capturing particles of said plurality of particles in separate compartments of the microfluidic device further comprises affinity-based capturing of said plurality of particles and employs a binding partner that binds a particle of said plurality of particles.

24. The method of claim 23, wherein the binding partner is affixed to a discrete region of the separate compartments of the microfluidic device, wherein the discrete region permits binding of only one particle of said plurality of particles.

25. The method of claim 23, wherein said affinity-based capturing of said plurality of particles comprises:
capturing supports comprising the binding partner at a plurality of capture sites in the separate compartments of the microfluidic device and producing immobilized supports at each of said plurality of capture sites, wherein the binding partner on each of the immobilized supports binds only one particle of said plurality of particles; and
binding one of said plurality of particles to the binding partner on each of the immobilized supports.

26. The method of claim 25, wherein the support is captured by mechanical capture.

27. The method of claim 25, wherein each of said plurality of capture sites comprises:
a capture feature with a size holding only one of the supports; and
a drain feature, wherein, when the capture feature is not occupied by the only one support, the drain feature permits a flow of fluid to pass through the capture site of said plurality of capture sites.

28. The method of claim 25, wherein the microfluidic device comprises a focusing feature to focus the supports and/or said plurality of particles to each of said plurality of capture sites.

29. The method of claim 1, wherein the one or more target nucleic acids comprise DNA or RNA and the reactions comprise one or more reactions selected from amplification of the DNA, digestion of the DNA with a nuclease, ligation of the DNA, ligation of an adaptor sequence onto the DNA, transposase-mediated incorporation of a transposon into the DNA, sequencing of the DNA, reverse transcription of the RNA, amplification of the RNA, and digestion of the RNA with an RNase.

30. The method of claim 1, wherein the particles comprise cells and the nucleic acid amplification reaction is whole genome amplification or whole transcriptome amplification.

31. The method of claim 1, wherein the amplification primers comprise a pair of inner primers and a pair of outer primers, wherein:
the inner primers comprise:
a forward, inner primer comprising a first nucleotide tag sequence, a first barcode nucleotide sequence, and a target-specific portion; and
a reverse, inner primer comprising a target-specific portion, the first barcode nucleotide sequence, and a second nucleotide tag sequence; and
the outer primers comprise:
a forward, outer primer comprising a second barcode nucleotide sequence and a first nucleotide tag-specific portion; and
a reverse, outer primer comprising a second nucleotide tag-specific portion and the second barcode nucleotide sequence;
wherein the outer primers are in excess of the inner primers; and
wherein an amplicon of the at least one amplicon comprises, from 5' to 3', the second barcode nucleotide sequence, the first nucleotide tag sequence, the first barcode nucleotide sequence, a target nucleotide sequence from the one or more target nucleic acids, the first barcode nucleotide sequence, the second nucleotide tag sequence, and the second barcode nucleotide sequence.

32. The method of claim 1, wherein the amplification primers comprise a pair of inner primers, a pair of stuffer primers, and a pair of outer primers, wherein:
the inner primers comprise:
a forward, inner primer comprising a first nucleotide tag sequence and a target-specific portion; and
a reverse, inner primer comprising a target-specific portion and a second nucleotide tag sequence;
the stuffer primers comprise:
a forward, stuffer primer comprising a third nucleotide tag sequence, a first barcode nucleotide sequence, and a first nucleotide tag-specific portion; and
a reverse, stuffer primer comprising a second nucleotide tag-specific portion, the first barcode nucleotide sequence, a fourth nucleotide tag sequence; and
the outer primers comprise:
a forward, outer primer comprising a second barcode nucleotide sequence and a third nucleotide tag-specific portion; and
a reverse, outer primer comprising a fourth nucleotide tag-specific portion and the second barcode nucleotide sequence;
wherein the outer primers are in excess of the stuffer primers, which are in excess of the inner primers; and
wherein the amplicon of the at least one amplicon comprises, from 5' to 3', the second barcode nucleotide sequence, the third nucleotide tag sequence, the first barcode nucleotide sequence, the first nucleotide tag sequence, a target nucleotide sequence from the one or more target nucleic acids, the second nucleotide tag sequence, the first barcode nucleotide sequence, the fourth nucleotide tag sequence, and the second barcode nucleotide sequence.

33. The method of claim 31, wherein the outer primers additionally comprise first and second DNA sequencing primer binding sites, and wherein an amplicon of the at least one amplicon comprises, from 5' to 3', the first DNA sequencing primer binding site, the second barcode nucleotide sequence, the first nucleotide tag sequence, the first barcode nucleotide sequence, the target nucleotide sequence from the one or more target nucleic acids, the first barcode nucleotide sequence, the second nucleotide tag sequence, the second barcode nucleotide sequence, and the second DNA sequencing primer binding site.

34. The method of claim 33, the method further comprises sequencing the at least one amplicon.

35. The method of claim 1, the method additionally comprises disrupting said particles prior to performing the nucleic acid amplification, when the particles are cells.

36. The method of claim 35, wherein said particles comprise cells, and the cells are disrupted by lysis prior to performing the nucleic acid amplification.

37. The method of claim 1, wherein the particles are treated with an agent that elicits a biological response prior to performing the plurality of reactions when the particles are cells.

38. The method of claim 1, wherein the method further comprises determining the presence or amount of said one or more target nucleic acids.

39. The method of claim 1, wherein the method further comprises determining the copy numbers of one or more DNA molecules in each of said particles when the one or more target nucleic acids are the one or more DNA molecules.

40. The method of claim 1, wherein the method further comprises determining the genotypes at one or more loci in genomic DNA in each of said particles when the one or more target nucleic acids are a part of the genomic DNA.

41. The method of claim 1, wherein the method further comprises determining a haplotype for a plurality of loci in genomic DNA in each of said particles when the one or more target nucleic acids are a part of the genomic DNA.

42. The method of claim 1, wherein the method further comprises determining the expression levels of one or more RNA molecules in each of said particles when the one or more target nucleic acids are the one or more RNA molecules.

43. The method of claim 1, wherein the method further comprises determining the nucleotide sequences of one or more RNA molecules in each of said particles when the one or more target nucleic acids are the one or more RNA molecules.

44. The method of claim 1, wherein the method further comprises determining the expression levels of one or more proteins in each of said particles when the particles are cells.

45. The method of claim 1, wherein said recovering the reaction products, comprising the at least one amplicon, from each of said separate reaction volumes comprises pooling the reaction products from each of the separate reaction compartments in a row or in a column.

46. The method of claim 1, wherein said recovering the reaction products, comprising the at least one amplicon, from each of said separate reaction volumes comprises pooling the reaction products from each of the separate reaction compartments in the microfluidic device.

* * * * *